(12) United States Patent
Armstrong et al.

(10) Patent No.: US 9,175,006 B2
(45) Date of Patent: Nov. 3, 2015

(54) COMPOSITIONS AND METHODS FOR CYCLOFRUCTANS AS SEPARATION AGENTS

(75) Inventors: Daniel W. Armstrong, Arlington, TX (US); Ping Sun, Arlington, TX (US); Zachary S. Breitbach, Arlington, TX (US); Chunlei Wang, Plainsboro, NJ (US)

(73) Assignee: Board of Regents, The University of Texas System, Austin, TX (US)

( * ) Notice: Subject to any disclaimer, the term of this patent is extended or adjusted under 35 U.S.C. 154(b) by 780 days.

(21) Appl. No.: 12/817,597

(22) Filed: Jun. 17, 2010

(65) Prior Publication Data

US 2011/0024292 A1 Feb. 3, 2011

Related U.S. Application Data

(60) Provisional application No. 61/187,868, filed on Jun. 17, 2009.

(51) Int. Cl.
*C07D 493/22* (2006.01)
*C08B 37/00* (2006.01)
*C08L 5/00* (2006.01)
*C09D 105/00* (2006.01)

(52) U.S. Cl.
CPC .............. *C07D 493/22* (2013.01); *C08B 37/00* (2013.01); *C08B 37/0054* (2013.01); *C08L 5/00* (2013.01); *C09D 105/00* (2013.01)

(58) Field of Classification Search
CPC .. C07D 493/22; C08B 37/00; C08B 37/0054; C09D 105/00; C08L 5/00
USPC ................... 210/635, 656, 659, 198.2, 502.1; 502/404; 536/53, 55.1, 116, 120
See application file for complete search history.

(56) References Cited

U.S. PATENT DOCUMENTS 3,472,835 A * 10/1969 Buckler et al. ................... 536/46
4,426,292 A * 1/1984 Wernick et al. ............... 210/635
4,539,399 A * 9/1985 Armstrong ..................... 536/103
4,781,858 A * 11/1988 Mizukami et al. ............. 516/100

(Continued)

FOREIGN PATENT DOCUMENTS

EP 1054020 11/2000
EP 1533327 5/2005

(Continued)

OTHER PUBLICATIONS

Atsumi, Masato et al., "Capped cyclofructan. Preparation and structure determination of 6A,6C-diO-(biphenyl-4,4'-disulfonyl)cycloinulohexaose", Tetrahedron Letters 1994, 35(31): 5661-4 (Abstract only).

(Continued)

*Primary Examiner* — Ernest G Therkorn
(74) *Attorney, Agent, or Firm* — Parks Wood LLC; Collen A. Beard, Esq.

(57) ABSTRACT

The present invention relates to derivatized cyclofructan compounds, compositions comprising derivatized cyclofructan compounds, and methods of using compositions comprising derivatized cyclofructan compounds for chromatographic separations of chemical species, including enantiomers. Said compositions may comprise a solid support and/or polymers comprising derivatized cyclofructan compounds.

19 Claims, 14 Drawing Sheets

(56) References Cited

U.S. PATENT DOCUMENTS

| | | | |
|---|---|---|---|
| 5,154,738 | A | 10/1992 | Armstrong |
| 5,626,757 | A | 5/1997 | Armstrong |
| 5,639,824 | A * | 6/1997 | Okamoto ............... 525/54.2 |
| 5,736,259 | A * | 4/1998 | Oda et al. .............. 428/532 |
| 6,217,769 | B1 * | 4/2001 | Okamoto et al. ........ 210/635 |
| 6,277,782 | B1 * | 8/2001 | Moller et al. ........... 502/402 |
| 6,342,592 | B1 * | 1/2002 | Duval et al. ............ 536/22.1 |
| 6,346,616 | B1 * | 2/2002 | Duval ..................... 536/123.1 |
| 6,358,418 | B1 * | 3/2002 | Oda et al. ................ 210/635 |
| 6,379,552 | B1 * | 4/2002 | Kitagawa et al. ........ 210/656 |
| 7,576,034 | B2 * | 8/2009 | Duval et al. ............. 502/402 |
| 7,597,804 | B2 * | 10/2009 | Duval et al. ............ 210/198.2 |
| 2003/0192829 | A1 * | 10/2003 | Ohnishi et al. .......... 210/656 |
| 2005/0048648 | A1 | 3/2005 | Fang et al. |
| 2006/0216328 | A1 | 9/2006 | Kis et al. |
| 2007/0049662 | A1 | 3/2007 | Han et al. |

FOREIGN PATENT DOCUMENTS

| | | |
|---|---|---|
| GB | 2282147 | 3/1995 |
| JP | 4237496 | 8/1992 |
| JP | 6043573 | 2/1994 |
| JP | 6071903 | 3/1994 |
| JP | 6121927 | 5/1994 |
| JP | 6124002 | 5/1994 |
| JP | 6157992 | 6/1994 |
| JP | 6250347 | 9/1994 |
| JP | 6298807 | 10/1994 |
| JP | 7023703 | 1/1995 |
| JP | 7064249 | 3/1995 |
| JP | 8127580 | 5/1996 |
| JP | 8140690 | 6/1996 |
| JP | 8165301 | 6/1996 |
| JP | 9048876 | 2/1997 |
| JP | 2004242623 | 9/2004 |
| JP | 2004337132 | 12/2004 |
| JP | 2004337133 | 12/2004 |
| JP | 2005179195 | 7/2005 |
| JP | 2006067894 | 3/2006 |
| JP | 2006067895 | 3/2006 |
| JP | 2006067896 | 3/2006 |
| JP | 2008069094 | 3/2008 |
| WO | WO-03077952 | 9/2003 |

OTHER PUBLICATIONS

Fujita, Kahee et al., "6-O-Sulfonates of cycloinulohexaose (cyclofructan-6)", Tetrahedron Letters 1994, 35(14): 2197-200 (Abstract only).

Hwa-Young, Kim et al., "Purification and characterization of cycloinulooligosaccharide fructanotransferase from Bacillus macerans (CFC1.", Journal of Microbiology and Biotechnology 1998, 8(3): 251-257 (Abstract only).

Immel, S. et al., "Molecular modeling of saccharides, part 16. The molecular geometries of cyclofructins.", Proceedings of the International Symposium on Cyclodextrins, 9th, Santiago de Comostela, Spain 1998, 57-62 (Abstract only).

Immel, Stefan et al., "Molecular modeling of Saccharides. Part 10. Studies on ketoses. Part 12. The electrostatic and lipophilic potential profies of α-cyclofructin: computation, visualization, and conclusions", Leibigs Annalen 1996, (1), 39-44 (Abstract only).

Immel, Stefan et al., "Molecular modeling of Saccharides. Part 19. Cyclofructins with six to ten β-(1→2)-linked fructofuranose units: geometries, electrostatic profiles, lipophilicity patterns, and potential for inclusion complexation.", Carbohydrate Research 1998, 313(2): 91-105 (Abstract only).

Jeon, Sung-Jong et al., "Cloning and characterization of cycloinulooligosaccharide fructanotranserase (CFTase) from Baccillus polymyxa MGL21", Journal of Microbiology and Biotechnology 2002, 12(6): 921-928 (Abstract only).

Jiang, C et al., "Synthesis and examination of sulfated cyclofructans as a novel class of chiral selectors for CE", Electrophoresis (Abstract only) Nov. 2009, 30(22):3897-909.

Kamata, Akira et al., "Production of cyclofructan from chicory", Bio Industry 1992, 9(11), 654-9 (Abstract only).

Kawamura, M. et al., "Effects of various saccharides on cycloinulo-oligosaccharide fructanotransferase reaction: production of β -inulotriosyl-α-D-mannopyranoside and 1-O- β -inulotriosyl-α -L-sorboypyranose", Carbohydrate Research 2000 , 323(1-4): 49-56 (Abstract only).

Kawamura, Mishio et al., "Enzymic formation of a cycloinulo-oligosaccharide from inulin by an extracellular enzyme of Bacillus circulans OKUMZ 31B", Carbohydrate Research 1989, 192: 83-90 (Abstract only).

Kawamura, Mishio et al., "Synthesis of methyl 6-O- β-inulotriosyl-α-D-glucopyranoside by Intermolecular transglycosidation reaction of cycloinulo-oligosaccharide fructanotransferase.", Carbohydrate Research 1997, 297(2): 187-190 (Abstract only).

Kida, Toshiyuki "Amphiphilic Cycloinulohexaose: Preparation, Surface-Active Properties, and Complexing Abilities toward Various Metal Chlorides", Bull. Chem. Soc. Jpn. 1998, 71: 1201-1205.

Kushibe, Sachiko et al., "Production of cyclofructan by Bacillus circulans MCI-2554", Research and Development Review—Mitsubishi Kasei Corporation 1994, 8(1): 44-9 (Abstract only).

Kushibe, Sachiko et al., "Production of cyclofructan from inulin by Bacillus circulans MCI-2554", Bioscience, Biotechnology, and Biochemistry 1994, 58(6): 1136-8 (Abstract only).

Kushibe, Sachiko et al., "Production of novel branched cyclofructans by Bacillus subtilis MCI-2834", Bioscience, Biotechnology, and Biochemistry 1996, 60(10): 1677-1680 (Abstract only).

Lichtenthaler, Frieder W. et al., "Computer simulation of chemical and biological properties of sucrose, the cyclodextrins and amylose", International Sugar Journal 1995, 97(1153): 13-22 (Abstract only).

Lim, Chae-Kwon et al., "Production of Cyclofructan by Cycloinulooligosaccharide Fructanotransferase Expressed in Saccharomyces cerevisiae", Korean Society for Microbiology and Biotechnology 2004, 32(1): 60-66 (Abstract only).

Ozaki, Mazuhiko et al., "Cryoprotective effects of cycloinulohexaose on freezing and freeze-drying of liposomes.", Chemical and Pharmaceutical Bulletin 1996, 44(11): 2116-2120 (Abstract only).

Ozaki, K. et al., "Effect of cycloinulohexaose with additives on the freeze-drying of liposome", International Journal of Pharmaceutics 1998, 160: 219-227.

Reijenga, Jetse C. et al., "Use of cyclofructan as a potential complexing agent in capillary electrophoresis", Journal of Chromatography A 1999, 838: 111-119.

Sawada, Masami et al., "The crystal structure of cycloinulohexaose produced from inulin by cycloinulo-oligosaccharide fructanotransferase", Carbohydrate Research 1991, 217: 7-17 (Abstract only).

Sawada, Masami et al., "Chiral Recognition in Host-Guest Complexation Determined by the Enantiomer-Labeled Guest Method Using Fast Atom Bombardment Mass Spectrometry", J. Am. Chem. Soc. 1995, 117: 7726-7736.

Sawada, Masami et al., "Measurement of chiral amino acid discrimination by cyclic oligosaccharides: a direct FAB mass spectrometric approach", Chem. Commun. 1998, 1453-1454.

Sawada, Masami et al., "Measurement of Chiral Recognition Properties of Crown Ethers Using Matrix Assisted Laser Desorption Ionization Mass Spectrometry", J. Mass Spectrom. Soc. Jpn. 2000, vol. 48, No. 2, 141-144.

Sawada, Masami et al. "Crystal structure of cycloinulohexaose", Chemistry Letters, (11): 2011-14 (Abstract only), 1990.

Sawada, Masami et al. "Chiral recognition in molecular complexion for the crown ether-amino ester system. A facile FAB mass spectrometric approach", J. Chem. Soc., Chem Commun. 1994, 2497-2498.

Sun, P. et al., "Development of new HPLC chiral stationary phases based on native and derivatized cyclofructans", Anal Chem Dec. 15, 2009, 81(24):10215-26.

Sun, Ping et al., "Effective enantiomeric separations of racemic primary amines by the isopropyl carbamate-cyclofructan6 (IP-CF6) chiral stationary phase", Department of Chemistry and Biochemistry, University of Texas at Arlington.

(56) References Cited

OTHER PUBLICATIONS

Takai, Yoshio et al., "Binding Characteristics of a New Host Family of Cyclic Oligosaccharides from Inulin: Permethylated Cycloinulohexoase and Cycloinuloheptaose", Journal of Organic Chemistry 1994, 59(11): 2967-75 (Abstract only).

Takai, Yoshio et al., "A permethylated cyclic fructo-oligosaccharide host that can bind cations in solution", J. Chem. Soc., Chem. Commun. 1993, 53-54 (Abstract only).

Uchiyama, Takao et al., "Complexing of cycloinulo-oligosaccharides with metal ions", Carbohydrate Research 1993, 241: 254-8 (Abstract only).

Uchiyama, T. et al., "Cycloinulo-oligosaccharides; structure and enzymic synthesis", Studies in Plant Science 1993, 3: 143-8 (Abstract only).

Yoshie, Naoko et al., "Complexation of cycloinulohexaose with some metal ions", Chemistry Letters 1993, 2: 353-6 (Abstract only).

Zhang, Y. et al., "The use of cyclofructans as novel chiral selectors for gas chromatography", Analyst. May 26, 2010, 135(5): 1076-83 (Abstract only).

* cited by examiner

COMPOSITIONS AND METHODS FOR CYCLOFRUCTANS AS SEPARATION AGENTS

CROSS REFERENCE TO RELATED APPLICATIONS

This application claims priority to provisional application No. 61/187,868, filed Jun. 17, 2009, the entire disclosure of which is incorporated by reference.

STATEMENT REGARDING FEDERALLY SPONSORED RESEARCH

None.

FIELD OF INVENTION

The present invention relates to the field of chromatography, especially chiral chromatography.

BACKGROUND

Enantiomeric liquid chromatography (LC) separations have attracted great attention in the past few decades. Currently, over a hundred chiral stationary phases (CSPs) have been reported, and these CSPs are made by coating or bonding the chiral selectors to supports, usually silica gel supports. Interestingly, only a few types/classes of CSPs dominate the field of enantiomeric separations. Polysaccharide-based CSPs, macrocyclic antibiotic CSPs, and π complex CSPs are examples of dominant classes. And within each class of CSP there often are one or two dominate entities. Thus, despite the introduction of many chiral selectors/CSPs, only a few are used for the majority of separations. It has been said that in order for any new CSP to make a substantial impact, it must fulfill one or more of the following requirements: (a) broader applicability than existing CSPs, (b) superior separation properties for specific enantiomers (e.g., better selectivity, higher efficiency, more beneficial solvent compatibilities, shorter separation times, lower cost, enhanced ability to use supercritical fluid chromatography, etc.), or (c) fill an important separation niche where no other CSPs are operative.

Cyclofructans (CFs) are one of a relatively small group of macrocyclic oligosaccharides. Cyclodextrins are perhaps the best known member of this class of molecules. However, CFs are quite different in both their structure and behavior. CFs are cycloinulo-oligosaccharides consisting of six or more β-(2→1)-linked D-fructofuranose units. Each fructofuranose unit contains four stereogenic centers and three hydroxyl groups. A common shorthand nomenclature for these compounds is CF6, CF7, CF8, etc., where CFn denotes a cyclofructan having n fructose moieties (i.e., 6, 7, 8, etc.) in the cyclic oligomer.

Cyclofructans were first reported by Kawamura and Uchiyama in 1989. They can be produced via fermentation of inulin by at least two different strains of *Bacillus circulans*. The gene that produces the cycloinulo-oligosaccharide fructanotransferase enzyme (CF Tase) has been isolated, and its sequence determined and incorporated into the common yeast, *Saccharomyces cerevisiae*. Hence, the facile production of CFs is possible. The basic structure of CFs is shown in FIG. 1. From the x-ray crystal structure of CF6 it is known that the smaller CFs have no hydrophobic cavities as do cyclodextrins. Consequently, hydrophobic inclusion complexation, which plays an important role in the association of organic molecules with cyclodextrins, does not seem to be relevant for cyclofructans.

Instead, the pentose moieties (fructoses) of CFs form a propeller-like circumference around a crown ether core unit. For example, the crystal structure of CF6 reveals that six fructofuranose rings are arranged in a spiral or propeller fashion around the 18-crown-6 core, oriented either up or down toward the mean plane of the crown ether. Six three-position hydroxyl groups alternate to point toward or away from the molecular center, and the three oxygen atoms pointing inside are very close to each other (~3 Å). It is clear that there is considerable internal hydrogen bonding in the cyclofructan molecule. As a result, access to the 18-crown-6 core on one side of the macrocycle is blocked by the hydrogen bonded hydroxyl groups. The other side of CF6 appears to be more hydrophobic, resulting from the methylene groups of —O—C—$CH_2$—O— around the central indentation. A computational lipophilicity pattern of CF6 also confirms that CF6 shows a clear "front/back" regionalization of hydrophilic and hydrophobic surfaces. Both the crystal structure and computational modeling studies demonstrate that CF6 appears to have considerable additional internal hydrogen bonding. The fact that three 3-OH groups completely cover one side of the 18-crown-6 ring and the core crown oxygens are almost folded inside the molecule makes $CF_6$ very different from other 18-crown-6 based chiral selectors. Table 1 gives relevant physico-chemical data for CF6, CF7 and CF8.

TABLE 1

Physico-chemical properties of cyclofructans 6-8.

| Macrocycle | M.W. | Melting Point (° C.) | $[\alpha]_D^{20}$ (°) in $H_2O$ | Cavity I.D. (Å) | Macrocycle O.D. (Å) | Macrocycle Height (Å) |
|---|---|---|---|---|---|---|
| CF6 | 972.84 | 210-219[a] (231-233) | −64.6 | 2.3 | 14.6 | 8.7-9.4 |
| CF7 | 1134.98 | 215-222 | N/A | 4.1 | 15.9 | 8.5-8.9 |
| CF8 | 1297.12 | N/A | N/A | 4.7 | 16.1 | 8.5-9.2 |

[a]Melts and decomposes in this range.

Cyclofructans have been used in a variety of applications, mostly as an additive in consumer products or as a means to associate metal ions in solution. Many applications of CFs as additives in consumer products are similar to those of cyclodextrins. For example, CFs have been used as paper coatings, moderators of food and drink bitterness and astringency, browning preventive agents, emulsion polymerization agents, ink formulation agents, agents for suppressing smells, parts of drug delivery systems, lubricants, and so on. In addition, CFs have been shown to have cryoprotective effects and to be useful as complexing agents for some ions. However, to our knowledge CFs or their analogues have never been used as a broadly useful CSP for the separation of enantiomers by chromatography. Not intending to be bound by theory, it is possible that un-derivatized (or "native") CFs cannot be used as CSPs for gas-liquid chromatography (GLC) due to their high melting points and their inability to solubilize in other liquid GLC stationary phases. For the above-mentioned structural reasons, it is also possible that native CF6 and other CFs have limited capabilities to form either hydrophobic inclusion complexes and/or crown ether inclusion complexes.

SUMMARY OF INVENTION

The present invention relates to compounds of formula I, compositions comprising compounds of formula I, and methods of using compositions comprising compounds of formula I for chromatographic separations of chemical species, where formula I is as follows:

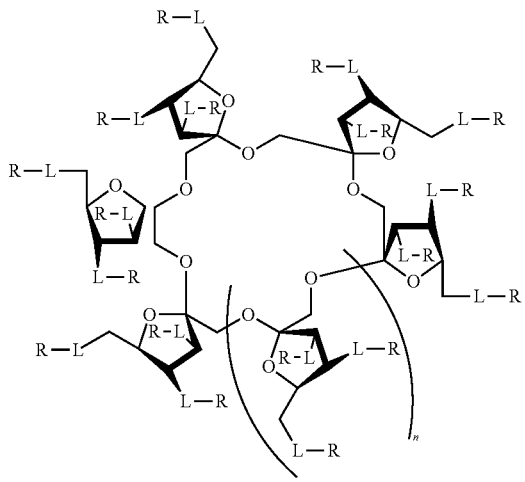

I wherein n, L and R are as herein described.

In one aspect, the present invention provides a composition comprising a solid support and a cyclofructan residue covalently linked to said solid support. In another aspect, the present invention provides a composition comprising a solid support and a derivatized cyclofructan residue of formula I, wherein n, L and R are as described herein and wherein one to five R groups are covalent bonds to the solid support.

In still another aspect, the present invention provides a composition comprising a solid support; and at least one polymer, wherein said polymer comprises at least one residue of an un-derivatized cyclofructan or derivatized cyclofructan of formula I, wherein n, L and R are as described herein and wherein zero to five R groups are covalent bonds to the solid support.

DETAILED DESCRIPTION OF THE INVENTION

Definitions

Figure 1:
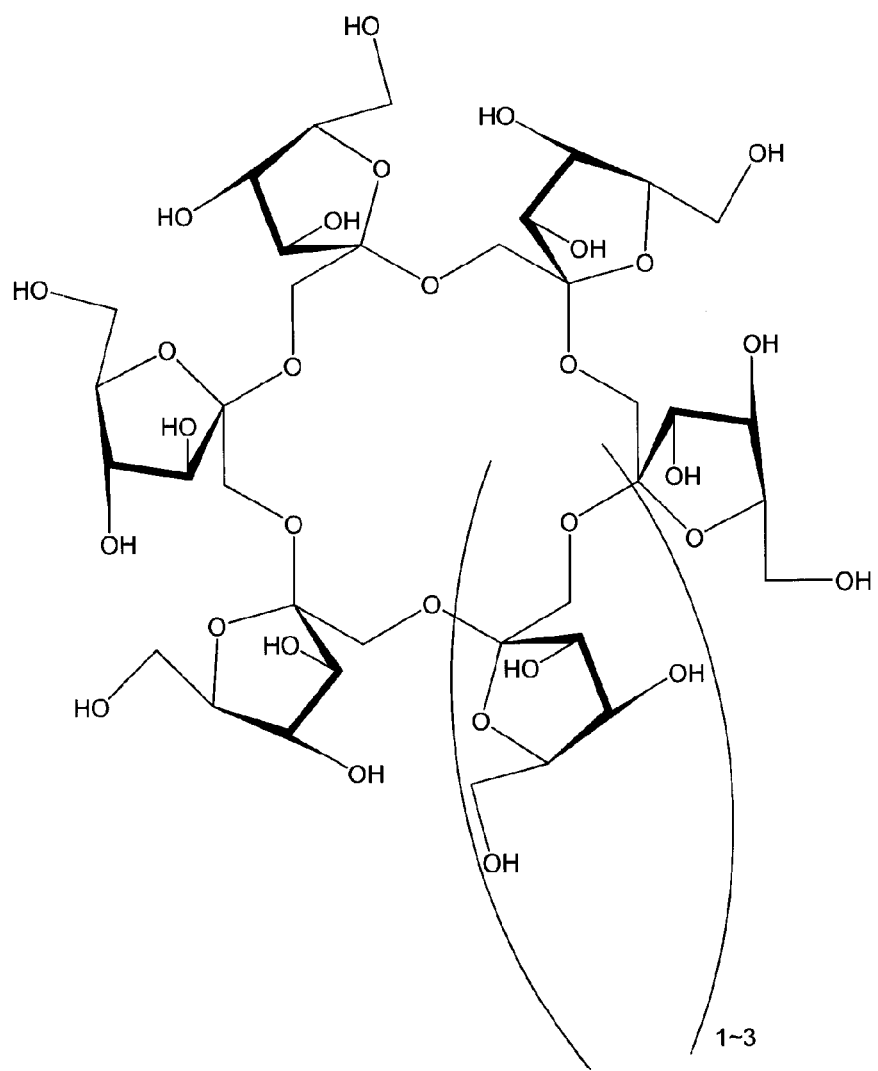
FIG. 1 is a depiction of the basic structure of a cyclofructan.

The following definitions are meant to clarify, but not limit, the terms defined. If a particular term used herein is not specifically defined, such term should not be considered indefinite. Rather, terms are used within their accepted meanings.

"Cyclofructan," as used herein, refers to a cycloinulo-oligosaccharide consisting of six or more β-(2→1)-linked D-fructofuranose units.

"Derivatized cyclofructan" or "functionalized cyclofructan," as used herein, refers to a cyclofructan in which one or more hydroxyl groups have been replaced with other functional groups. Typically, about 2 to 18 hydroxyl groups are replaced with other functional groups in a derivatized or functionalized CF6 of the present invention. Typically, about 2 to 21 hydroxyl groups are replaced with other functional groups in a derivatized or functionalized CF7 of the present invention. Typically, about 2 to 24 hydroxyl groups are replaced with other functional groups in a derivatized or functionalized CF8 of the present invention. "Low" derivatization refers to the replacement of about 2 to about 7 hydroxyl groups with other functional groups. Similarly, "un-derivatized cyclofructan" or "native cyclofructan" refers to a cyclofructan in which none of the hydroxyl groups have been replaced with a different functional group.

"Alkyl," as used herein, refers to an aliphatic hydrocarbon chain of 1 to about 20 carbon atoms, preferably 1 to about 10 carbon atoms, more preferably, 1 to about 6 carbon atoms, and even more preferably, 1 to about 4 carbon atoms and includes straight and branched chains such as methyl, ethyl, n-propyl, isopropyl, n-butyl, isobutyl, sec-butyl, t-butyl, n-pentyl, isopentyl, neo-pentyl, n-hexyl, and isohexyl.

"Lower alkyl" refers to an alkyl having 1 to about 4 carbon atoms, where "alkyl" is as defined herein.

"Alkylenyl," as used herein, refers to a divalent alkyl group, where "alkyl" is as defined herein.

"Arylenyl," as used herein, refers to a divalent aryl group, where "aryl" is as defined herein.

"Aryl," as used herein, refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, phenanthrenyl, and 3,5-dimethylphenyl. Aryl may be optionally substituted with one or more $R^1$, as defined herein.

"Heteroaryl," as used herein, refers to an optionally substituted, mono-, di-, tri-, or other multicyclic aromatic ring system, including heterocyclic rings, that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyriyl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. Heteroaryl may be optionally substituted with one or more $R^1$, as defined herein.

"Heterocyclic ring," as used herein, refers to a stable 5- to 7-membered monocyclic or bicyclic or 7- to 10-membered bicyclic heterocyclic ring that is saturated, partially unsaturated or unsaturated (aromatic), and which contains carbon atoms and from 1 to 4 heteroatoms independently selected from the group consisting of N, O and S and including any bicyclic group in which any of the above defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. If specifically noted, a nitrogen atom in the heterocycle may optionally be quaternized. It is preferred that when the total number of S and O atoms in the heterocycle exceeds one, then these heteroatoms are not adjacent to one another. It is preferred that the total number of S and O atoms in the heterocycle is not more than one. Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4H-carbazolyl, alpha-, beta-, or gamma-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylpyrimidinyl, phenanthridinyl, phenanthrolinyl, phenoxazinyl, phenazinyl, phenothiazinyl, phenoxathiinyl, phenoxazinyl, phthalazinyl, piperazinyl, piperidinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and Spiro compounds containing, for example, the above heterocycles.

"Cycloalkyl," as used herein, refers to an optionally substituted, alkyl group having one or more rings in their structures having from 3 to about 20 carbon atoms (and all combinations and subcombinations of ranges and specific numbers of carbon atoms therein), with from 3 to about 10 carbon atoms being preferred. Multi-ring structures may be bridged or fused ring structures. Groups include, but are not limited to, cyclopropyl, cyclobutyl, cyclopentyl, cyclohexyl, cyclooctyl, 2-[4-isopropyl-1-methyl-7-oxa-bicyclo[2.2.1] heptanyl], 2-[1,2,3,4-tetrahydro-naphthalenyl], and adamantyl. Cycloalkyl may be optionally substituted with one or more $R^1$, as defined herein.

"Halo" or "halogen," as used herein, refers to chloro, bromo, fluoro, and iodo, or chlorine, bromine, fluorine, and iodine.

"Saccharide residue," as used herein, refers to a monosaccharide, disaccharide, oligosaccharide, or polysaccharide, or to a compound comprising a monosaccharide, disaccharide, oligosaccharide, or polysaccharide, wherein one or more hydroxyl groups of the saccharide residue may optionally be replaced with a different functional group.

Compounds

Embodiments of the present invention comprise derivatized cyclofructans, compositions, and methods of use thereof. The present invention may be embodied in a variety of ways.

Some embodiments of the present invention comprise a compound of formula I:

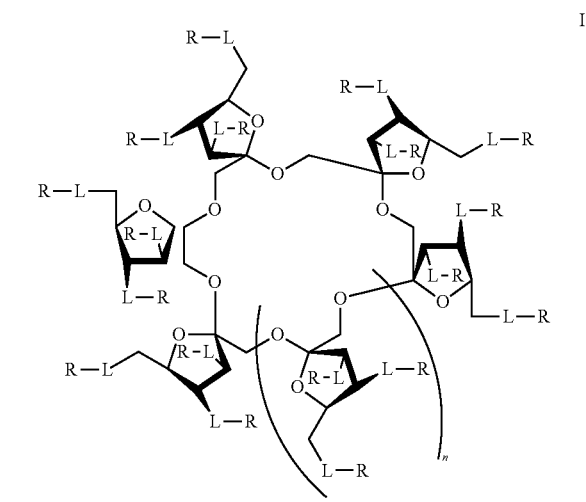

wherein:
n is 1-3;
each L is, independently,

O,
CR$_2$,
NR$^2$,
O—C(=O),
O—C(=O)—NR$^2$,
NC(=O)—NR$^2$, or

each R is, independently,
H,
(C$_1$-C$_{20}$)alkyl optionally substituted with 1-3 R$^1$,
(C$_3$-C$_{20}$)cycloalkyl optionally substituted with 1-3 R$^1$,
(C$_5$-C$_{50}$)aryl optionally substituted with 1-3 R$^1$, heteroaryl optionally substituted with 1-3 R$^1$,
(C$_1$-C$_{20}$)alkoxy(C$_1$-C$_{20}$)alkyl,
H$^2$C=CH— (when L is O—C(=O)),
H$^2$C=C(CH$_3$)— (when L is O—C(=O)),
alkylenyl-N=C=O;
arylenyl-N=C=O;
—SO$_2$R$^5$ (when L is O),
—SO$_3$ (when L is O),
(C$_5$-C$_{50}$)aryl(C$_1$-C$_{20}$)alkyl optionally substituted with 1-3 R$^1$, or saccharide residue lacking a hydroxyl group (when L is O);
R$^1$ is, independently, (C$_1$-C$_{10}$)alkyl optionally substituted with 1-3 R$^6$, halo, hydroxy, —NR$^3$R$^4$, —COOR$^2$, —COR$^2$, nitro, trihaloalkyl, or —Si(OR$^2$)$_3$;
R$^2$ is, independently, H or (C$_1$-C$_{10}$)alkyl;
R$^3$ is, independently, H or (C$_1$-C$_{10}$)alkyl;
R$^4$ is, independently, H or (C$_1$-C$_{10}$)alkyl;
R$^5$ is, independently, (C$_1$-C$_{20}$)alkyl optionally substituted with 1-3 R$^1$, (C$_5$-C$_{50}$)aryl optionally substituted with 1-3 R$^1$, or heteroaryl optionally substituted with 1-3 R$^1$;
R$^6$ is, independently, halo, hydroxy, —NR$^3$R$^4$, —COOR$^2$, —COR$^2$, nitro, trihaloalkyl, or —Si(OR$^2$)$_3$; and
provided that all of said R groups are not simultaneously H or methyl.

In some embodiments of the present invention, one or more L groups is O. In that case, O is a divalent moiety and is connected to the CF and the R group with single bonds. In other embodiments of the present invention, one or more L groups is CR$_2$. In that case, CR$_2$ is a divalent moiety and is connected to the CF via a C—C single bond between the C atom of the L group and a C atom in the CF. The L group is connected to the R group via a C—R single bond between the C atom of the L group and an atom in the R group. In some embodiments, one or more L groups is NR$^2$. In that case, NR$^2$ is a divalent moiety and is connected to the CF via an N—C single bond between the N atom of the L group and a C atom in the CF. The L group is connected to the R group via an N—R single bond between the N atom of the L group and an atom in the R group. In other embodiments of the present invention, one or more L groups is O—C(=O). In that case, O—C(=O) is a divalent moiety and is connected to the CF via a C—O single bond between the first O atom of the L group and a C atom in the CF. Said first O atom of the L group is in turn bonded to the carbonyl carbon of the L group through a C—O single bond. The L group is bonded to the R group via a C—R single bond between the carbonyl carbon of the L group and an atom in the R group. In still other embodiments of the present invention, one or more L groups is O—C(=O)—NR$^2$. In that case, O—C(=O)—NR$^2$ is a divalent moiety and is connected to the CF via a C—O single bond between the first O atom of the L group and a C atom in the CF. Said first O atom of the L group is in turn bonded to the carbonyl carbon of the L group through a C—O single bond. The carbonyl carbon of the L group is in turn bonded to the N of the L group via a C—N single bond. The L group is bonded to the R group via a N—R single bond between the N atom of the L group and an atom in the R group. In some embodiments of the present invention, one or more L groups is NC(=O)—NR$^2$. In that case, NC(=O)—NR$^2$ is a divalent moiety and is connected to the CF via a C—N double bond between the first N atom of the L group and a C atom in the CF. Said first N atom of the L group is in turn bonded to the carbonyl carbon of the L group through a C—N single bond. The carbonyl carbon of the L group is in turn bonded to the second N of the L group via a C—N single bond. The L group is bonded to the R group via a N—R single bond between the second N atom of the L group and an atom in the R group. In other embodiments of the present invention, one or more L groups is the cycloaddition product of a 1,3-dipolar cycloaddition reaction between an azide and an alkyne (click chemistry). In that case, the cycloaddition product is a divalent moiety and can be connected to the CF and the R group in either of two ways. First, the CF can be connected to the L group via a C—N single bond between a C atom in the CF and the N atom in the cylcoaddition product depicted above as having two single bonds (one N—N single bond and one C—N single bond). The L group would then be connected to the R group through a C—R single bond between an atom of the R group and the C atom in the cycloaddition product in a β position relative to the N atom of the cycloaddition product bonded to the CF. This is the connectivity that would result from a putative reaction between an azide-functionalized CF and an alkyne-containing R group. The second possible connectivity of this L group is the reverse, resulting from a putative reaction between an alkyne-functionalized CF and an azide-containing R group.

In some embodiments of the present invention, an L group and a portion of an R group in formula I may together comprise all or part of a functional group serving to link the cyclofructan backbone to another moiety. In some embodiments of the present invention, an L group and a portion of an R group in formula I may together form all or part of a carbamate, ester, ether, alkylenyl, secondary or tertiary amine, or 1,3-dipolar cycloaddition product ("click chemistry") linkage between the CF and another moiety. In some embodiments of the present invention, no -LR group in formula I is —OH or —O-methyl. In other embodiments of the present invention, no -LR group in formula I is —OH or —O-methyl, and not all -LR groups are the same. In other embodiments of the present invention, no -LR group in formula I is —OH or —O-methyl, and all -LR groups are the same. In still other embodiments of the present invention, at least one but not all -LR groups in formula I is —OH or —O-methyl.

In some embodiments, a compound of formula I is synthesized by any means not inconsistent with the objectives of the present invention. In some embodiments of the present invention, a compound of formula I may be synthesized from native CF$_n$ using a reaction scheme and one or more reagents capable of forming a carbamate, ester, ether, alkylenyl, secondary or tertiary amine, or 1,3-dipolar cycloaddition product ("click chemistry") linkage as described herein.

Compositions

Some embodiments of the present invention comprise compositions comprising derivatized or un-derivatized cyclofructans.

Figure 2:
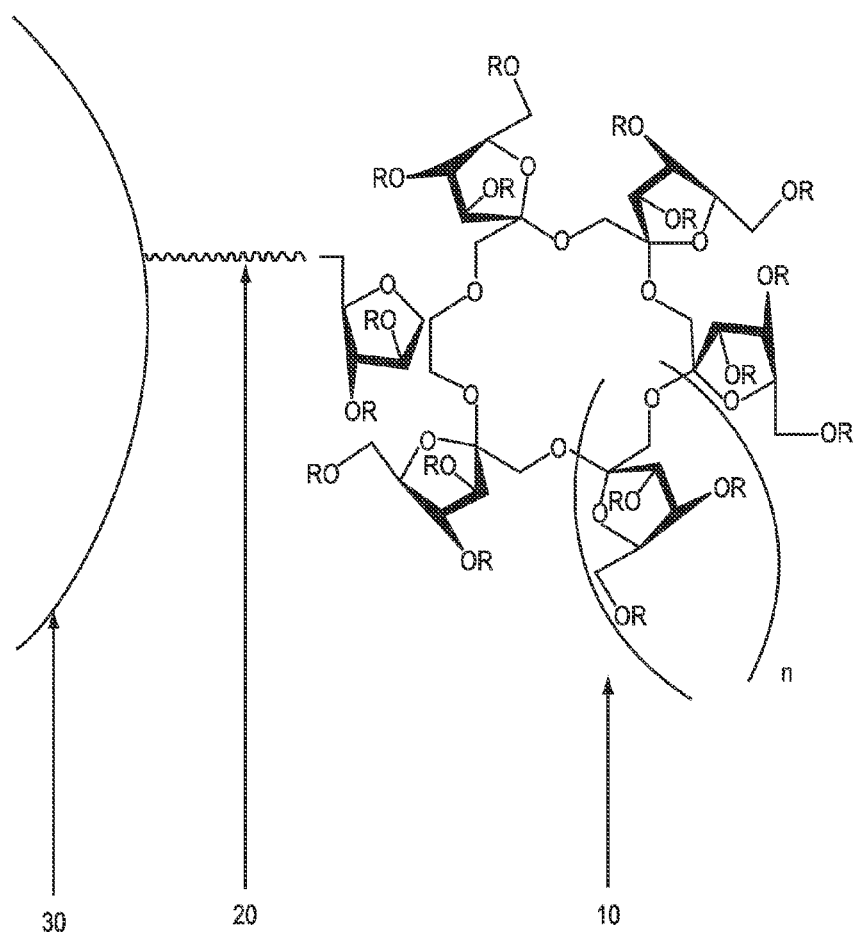
FIG. 2 is a depiction of a composition comprising a solid support and a derivatized cyclofructan residue of the present invention.

In some embodiments of the present invention, a composition comprises a solid support and a cyclofructan residue associated with said solid support. Said cyclofructan residue may be associated with said solid support by any means not inconsistent with the objectives of the present invention. In some embodiments of the present invention, a composition comprises a solid support and a cyclofructan residue covalently linked to said solid support. In other embodiments of the present invention comprising solid supports, cyclofructans can be directly absorbed to a solid support. Referring to FIG. 2, in some embodiments, a cyclofructan (component 10) can be directly covalently attached to a solid support (component 30) through linker (component 20). In still other embodiments, cyclofructans can be absorbed or covalently attached to a polymer or oligomer which can then be absorbed, coated, or attached to a support. In some embodiments of the present invention, a composition comprises a solid support and a cyclofructan residue covalently linked to said solid support, wherein said cyclofructan residue is lacking sulfate functionality.

In embodiments of the present invention comprising compositions comprising a solid support and a cyclofructan residue associated with said solid support, the cyclofructan residue can comprise any cyclofructan residue not inconsistent with the objectives of the invention. In some embodiments of the present invention, the cyclofructan is a native cyclofructan. In other embodiments, the cyclofructan is a derivatized cyclofructan. In still other embodiments of the present invention, a composition comprises a solid support and a derivatized cyclofructan residue of formula I:

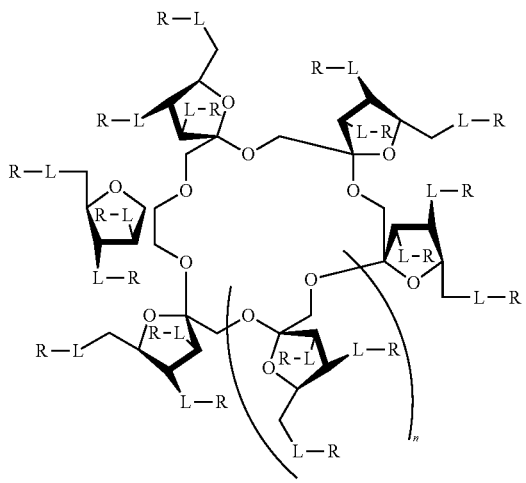

I wherein:
n is 1-3;
each L is, independently,
  O,
  $CR_2$,
  $NR^2$,
  O—C(═O),
  O—C(═O)—$NR^2$,
  NC(═O)—$NR^2$, or

each R is, independently,
  H,
  $(C_1-C_{20})$alkyl optionally substituted with 1-3 $R^1$,
  $(C_3-C_{20})$cycloalkyl optionally substituted with 1-3 $R^1$,
  $(C_5-C_{50})$aryl optionally substituted with 1-3 $R^1$, heteroaryl optionally substituted with 1-3 $R^1$, $(C_1-C_{20})$alkoxy$(C_1-C_{20})$alkyl,
$H^2C$═CH— (when L is O—C(═O)),
$H^2C$═C($CH_3$)— (when L is O—C(═O)),
alkylenyl-N═C═O;
arylenyl-N═C═O;
—$SO_2R^5$ (when L is O),
—$SO_3$ (when L is O),
$(C_5-C_{50})$aryl$(C_1-C_{20})$alkyl optionally substituted with 1-3 $R^1$, or saccharide residue lacking a hydroxyl group (when L is O), or comprises a covalent bond to said solid support;

$R^1$ is, independently, $(C_1-C_{10})$alkyl optionally substituted with 1-3 $R^6$, halo, hydroxy, —$NR^3R^4$, —$COOR^2$, —$COR^2$, nitro, trihaloalkyl, or —$Si(OR^2)_3$;

$R^2$ is, independently, H or $(C_1-C_{10})$alkyl;
$R^3$ is, independently, H or $(C_1-C_{10})$alkyl;
$R^4$ is, independently, H or $(C_1-C_{10})$alkyl;
$R^5$ is, independently, $(C_1-C_{20})$alkyl optionally substituted with 1-3 $R^1$, $(C_5-C_{50})$aryl optionally substituted with 1-3 $R^1$, or heteroaryl optionally substituted with 1-3 $R^1$;
$R^6$ is, independently, halo, hydroxy, —$NR^3R^4$, —$COOR^2$, —$COR^2$, nitro, trihaloalkyl, or —$Si(OR^2)_3$;
wherein one to five R groups comprise covalent bonds to the solid support.

In some embodiments of the present invention comprising a cyclofructan of formula I, one or more L groups in formula I is O. In that case, O is a divalent moiety and is connected to the CF and the R group as described herein. In other embodiments of the present invention, one or more L groups is $CR_2$. In that case, $CR_2$ is a divalent moiety and is connected to the CF and the R group as described herein. In some embodiments, one or more L groups is $NR^2$. In that case, $NR^2$ is a divalent moiety and is connected to the CF and the R group as described herein. In other embodiments of the present invention, one or more L groups is O—C(═O). In that case, O—C(═O) is a divalent moiety and is connected to the CF and the R group as described herein. In still other embodiments of the present invention, one or more L groups is O—C(═O)—$NR^2$. In that case, O—C(═O)—$NR^2$ is a divalent moiety and is connected to the CF and the R group as described herein. In some embodiments of the present invention, one or more L groups is NC(═O)—$NR^2$. In that case, NC(═O)—$NR^2$ is a divalent moiety and is connected to the CF and the R group as described herein. In other embodiments of the present invention, one or more L groups is the cycloaddition product of a 1,3-dipolar cycloaddition reaction between an azide and an alkyne (click chemistry). In that case, the cycloaddition product is a divalent moiety and can be connected to the CF and the R group as described herein.

In some embodiments of the present invention comprising a cyclofructan of formula I, n is 1. In other embodiments, n is 2. In still other embodiments, n is 3.

In some embodiments of the present invention comprising a cyclofructan of formula I, at least one L is O. In other embodiments, at least one L is O—C(═O). In still other embodiments, at least one L is O—C(═O)—$NR^2$. In some embodiments, at least one L is NC(═O)—$NR^2$. In some embodiments of the present invention comprising a cyclofructan of formula I, each R is, independently, H, methyl, ethyl, n-propyl, isopropyl, n-butyl, t-butyl, cyclohexyl, phenyl, tolyl, trichlorophenyl, chlorophenyl, bromophenyl, iodophenyl, hydroxyethyl, hydroxypropyl, dichlorophenyl, benzyl, chlorotolyl, naphthylethyl, nitrophenyl, dinitrophenyl, trinitrophenyl, trifluoromethyl, dinitro, 3,5-dimethylphenyl, or adamantyl. In other embodiments, each R is, independently, isopropyl, tert-butyl, xylyl, dichlorophenyl, 3,5-dimethylphenyl, or naphthylethyl.

In some embodiments of the present invention comprising a cyclofructan of formula I, each $R^1$ is, independently, hydroxypropyl, hydroxyethyl, methyl, trichloromethyl, trifluoromethyl, chloro, bromo, or iodo.

In embodiments of the present invention comprising compositions comprising a solid support and a cyclofructan residue associated with said solid support, the solid support can be any solid support not inconsistent with the objectives of the present invention. In some embodiments of the present invention, a composition comprises a solid support and a derivatized cyclofructan residue of formula I, wherein said solid support is a silica gel support.

In some embodiments of the present invention, a composition comprises a solid support and at least one polymer, wherein said polymer comprises at least one residue of a derivatized cyclofructan of formula I:

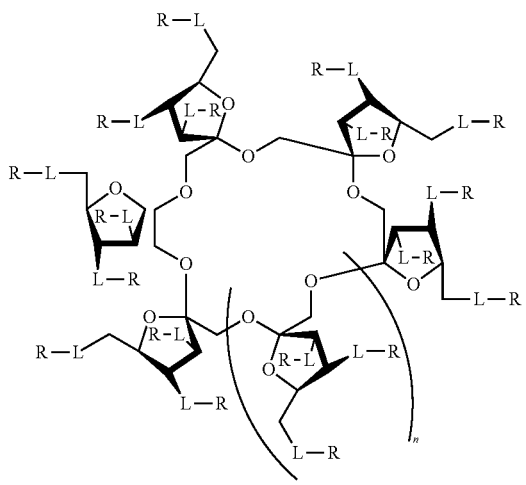

wherein:
each n is, independently, 1-3;
each L is, independently,
  O,
  $CR^2$,
  $NR^2$,
  O—C(=O),
  O—C(=O)—$NR^2$,
  NC(=O)—$NR^2$, or

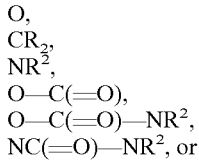

each R is, independently,
  Y,
  Z,
  H,
  $(C_1$-$C_{20})$alkyl optionally substituted with 1-3 $R^1$,
  $(C_3$-$C_{20})$cycloalkyl optionally substituted with 1-3 $R^1$,
  $(C_5$-$C_{50})$aryl optionally substituted with 1-3 $R^1$,
  heteroaryl optionally substituted with 1-3 $R^1$,
  $(C_1$-$C_{20})$alkoxy$(C_1$-$C_{20})$alkyl,
  $H_2C$=CH— (when L is O—C(=O)),
  $H_2C$=C(CH_3)— (when L is O—C(=O)),
  alkylenyl-N=C=O;
  arylenyl-N=C=O;
  —$SO_2R^5$ (when L is O),
  —$SO_3$ (when L is O),
  $(C_5$-$C_{50})$aryl$(C_1$-$C_{20})$alkyl optionally substituted with 1-3 $R^1$, or saccharide residue lacking a hydroxyl group (when L is O),
$R^1$ is, independently, $(C_1$-$C_{10})$alkyl optionally substituted with 1-3 $R^6$, halo, hydroxy, —$NR^3R^4$, —$COOR^2$, —$COR^2$, nitro, trihaloalkyl, or —$Si(OR^2)_3$;
$R^2$ is, independently, H or $(C_1$-$C_{10})$alkyl;
$R^3$ is, independently, H or $(C_1$-$C_{10})$alkyl;
$R^4$ is, independently, H or $(C_1$-$C_{10})$alkyl;
$R^5$ is, independently, $(C_1$-$C_{20})$alkyl optionally substituted with 1-3 $R^1$, $(C_5$-$C_{50})$aryl optionally substituted with 1-3 $R^1$, or heteroaryl optionally substituted with 1-3 $R^1$;
$R^6$ is, independently, halo, hydroxy, —$NR^3R^4$, —$COOR^2$, —$COR^2$, nitro, trihaloalkyl, or —$Si(OR^2)_3$; and
Y comprises a covalent bond to a different monomer residue; and
Z comprises a covalent bond to said solid support; and
wherein zero to five R groups comprise covalent bonds to the solid support.

In embodiments of the present invention comprising a composition comprising a solid support and at least one polymer, wherein said polymer comprises at least one residue of a derivatized cyclofructan of formula I, said solid support can be any solid support not inconsistent with the objectives of the present invention, as described herein.

In embodiments of the present invention comprising a composition comprising a solid support and at least one polymer, wherein said polymer comprises at least one residue of a derivatized cyclofructan of formula I, said at least one residue of a derivatized cyclofructan can be any residue of a derivatized cyclofructan not inconsistent with the objectives of the present invention, as described herein.

In embodiments of the present invention comprising a composition comprising a solid support and at least one polymer, wherein said polymer comprises at least one residue of a derivatized cyclofructan of formula I, said polymer can be any polymer not inconsistent with the objectives of the present invention. In some embodiments of the present invention comprising a composition comprising a solid support and at least one polymer, wherein said polymer comprises at least one residue of a derivatized cyclofructan of formula I, said polymer forms a coating on said solid support. In other embodiments of the present invention comprising a composition comprising a solid support and at least one polymer, wherein said polymer comprises at least one residue of a derivatized cyclofructan of formula I, said polymer is covalently bonded to said solid support. In still other embodiments of the present invention comprising a composition comprising a solid support and at least one polymer, wherein said polymer comprises at least one residue of a derivatized cyclofructan of formula I, said residue of a derivatized cyclofructan of formula I forms a pendant group on said polymer. In some embodiments of the present invention comprising a composition comprising a solid support and at least one polymer, wherein said polymer comprises at least one residue of a derivatized cyclofructan of formula I, said residue of a derivatized cyclofructan of formula I forms a portion of the backbone of said polymer.

In general, cyclofructan-containing polymers of the present invention can be classified into two categories: (1) polymers having CF units as the skeleton and (2) polymers having CFs as pendant groups. Embodiments of the present invention comprising polymers having CF units as the skeleton can be made by polymerizing CFs using any means not inconsistent with the objectives of the present invention. In some embodiments, CFs can be polymerized with hexamethylene diisocyanate in dried N,N'-dimethylformide (DMF) or epichlorohydrin in basic conditions to afford polymers having CF units as the skeleton. A CF-containing polymer prepared in this way can be coated onto a solid support or covalently bonded to it as described herein (e.g., via carbmate linkages). Embodiments of the present invention comprising polymers having CF units as the skeleton can also be made by preparing acrylate-functionalized CFs (e.g., methacrylate-CFs) to serve as CF-containing monomers and then copolymerizing them with other monomers (e.g., acrylamide, acrylic acid, N-vinylpyrrolidone) to afford polymers having CF units as the skeleton. A CF-containing polymer prepared in this way can be coated or bonded onto a solid support as described herein. Embodiments of the present invention comprising polymers having CF units as the skeleton can also be made by anchoring one CF-containing monomer to a solid support and then copolymerizing with other monomers on the surface of the solid support.

Embodiments of the present invention comprising polymers having CF units as pendant groups can be made by preparing a CF derivatized with an appropriate functional group (e.g., p-tosyl) and then reacting the appropriately derivatized CF with a polymer (e.g., poly(allylamine), poly(ethyleneimine), poly(vinylamine), or poly(vinylimidazole)) to afford polymers having CF units as pendant groups. A CF-containing polymer prepared in this way can be coated or bonded onto a solid support as described herein. Embodiments of the present invention comprising polymers having CF units as pendant groups can also be made by first coating an appropriate polymer onto a solid support as described herein and then reacting the appropriate derivatized CF with the polymer-coated or -bonded solid support as described herein.

Methods

Some embodiments of the present invention comprise methods of chromatographic separation, including chiral chromatographic separation.

In some embodiments of the present invention, a method of chromatographic separation comprises providing, as a first stationary phase, a composition to separate chemical species in a mixture, wherein the composition comprises a solid support and a derivatized cyclofructan residue of formula I:

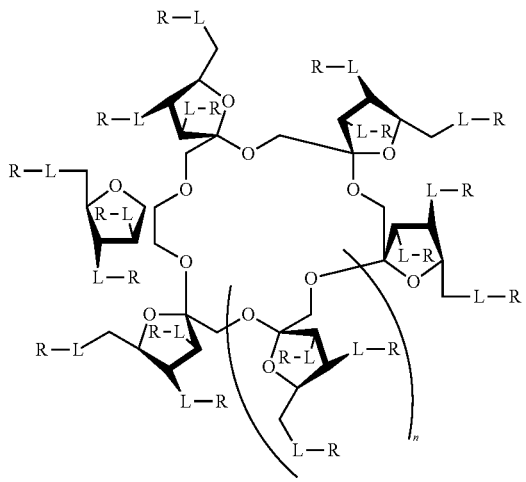

wherein:
n is 1-3;
each L is, independently,
 O,
 $CR_2$,
 $NR^2$,
 O—C(=O),
 O—C(=O)—$NR^2$,
 NC(=O)—$NR^2$, or

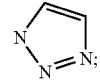

each R is, independently,
 H,
 $(C_1-C_{20})$alkyl optionally substituted with 1-3 $R^1$,
 $(C_3-C_{20})$cycloalkyl optionally substituted with 1-3 $R^1$,
 $(C_5-C_{50})$aryl optionally substituted with 1-3 $R^1$, heteroaryl optionally substituted with 1-3 $R^1$,
 $(C_1-C_{20})$alkoxy$(C_1-C_{20})$alkyl,
 $H_2C=CH—$ (when L is O—C(=O)),
 $H_2C=C(CH_3)—$ (when L is O—C(=O)),
 alkylenyl-N=C=O;
 arylenyl-N=C=O;
 —$SO_2R^5$ (when L is O),
 —$SO_3$ (when L is O),
 $(C_5-C_{50})$aryl$(C_1-C_{20})$alkyl optionally substituted with 1-3 $R^1$, or saccharide residue lacking a hydroxyl group (when L is O), or comprises a covalent bond to said solid support;
$R^1$ is, independently, $(C_1-C_{10})$alkyl optionally substituted with 1-3 $R^6$, halo, hydroxy, —$NR^3R^4$, —$COOR^2$, —$COR^2$, nitro, trihaloalkyl, or —$Si(OR^2)_3$;
$R^2$ is, independently, H or $(C_1-C_{10})$alkyl;
$R^3$ is, independently, H or $(C_1-C_{10})$alkyl;
$R^4$ is, independently, H or $(C_1-C_{10})$alkyl;
$R^5$ is, independently, $(C_1-C_{20})$alkyl optionally substituted with 1-3 $R^1$, $(C_5-C_{50})$aryl optionally substituted with 1-3 $R^1$, or heteroaryl optionally substituted with 1-3 $R^1$;
$R^6$ is, independently, halo, hydroxy, —$NR^3R^4$, —$COOR^2$, —$COR^2$, nitro, trihaloalkyl, or —$Si(OR^2)_3$; and
wherein one to five R groups comprise covalent bonds to the solid support.

In some embodiments of the present invention comprising a cyclofructan of formula I, one or more L groups in formula I is O. In that case, O is a divalent moiety and is connected to the CF and the R group as described herein. In other embodiments of the present invention, one or more L groups is $CR_2$. In that case, $CR_2$ is a divalent moiety and is connected to the CF and the R group as described herein. In some embodiments, one or more L groups is $NR^2$. In that case, $NR^2$ is a divalent moiety and is connected to the CF and the R group as described herein. In other embodiments of the present invention, one or more L groups is O—C(=O). In that case, O—C(=O) is a divalent moiety and is connected to the CF and the R group as described herein. In still other embodiments of the present invention, one or more L groups is O—C(=O)—$NR^2$. In that case, O—C(=O)—$NR^2$ is a divalent moiety and is connected to the CF and the R group as described herein. In some embodiments of the present invention, one or more L groups is NC(=O)—$NR^2$. In that case, NC(=O)—$NR^2$ is a divalent moiety and is connected to the CF and the R group as described herein. In other embodiments of the present invention, one or more L groups is the cycloaddition product of a 1,3-dipolar cycloaddition reaction between an azide and an alkyne (click chemistry). In that case, the cycloaddition product is a divalent moiety and can be connected to the CF and the R group as described herein.

In some embodiments of the present invention, a method of chromatographic separation comprises providing, as a first stationary phase, a composition to separate chemical species in a mixture, wherein the composition comprises a solid support and at least one polymer, wherein said polymer comprises at least one residue of a derivatized cyclofructan of formula I:

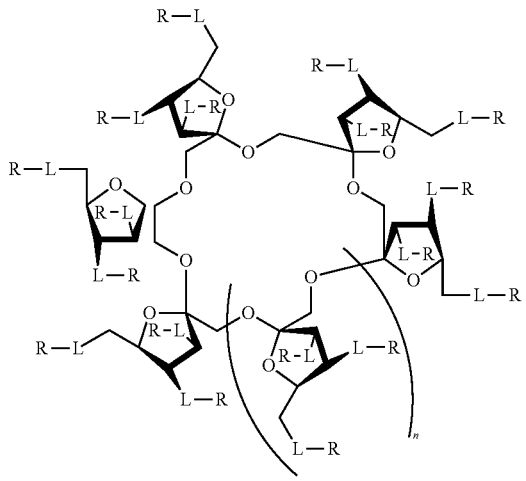

wherein:
each n is, independently, 1-3;
each L is, independently,
O,
$CR_2$,
$NR^2$,
O—C(=O),
O—C(=O)—$NR^2$,
NC(=O)—$NR^2$, or

each R is, independently,
Y,
Z,
H,
$(C_1-C_{20})$alkyl optionally substituted with 1-3 $R^1$,
$(C_3-C_{20})$cycloalkyl optionally substituted with 1-3 $R^1$,
$(C_5-C_{50})$aryl optionally substituted with 1-3 $R^1$,
heteroaryl optionally substituted with 1-3 $R^1$,
$(C_1-C_{20})$alkoxy$(C_1-C_{20})$alkyl,
$H^2C$=CH— (when L is O—C(=O)),
$H^2C$=C($CH_3$)— (when L is O—C(=O)),
alkylenyl-N=C=O;
arylenyl-N=C=O;
—$SO_2R^5$ (when L is O),
—$SO_3$ (when L is O),
$(C_5-C_{50})$aryl$(C_1-C_{20})$alkyl optionally substituted with 1-3 $R^1$, or saccharide residue lacking a hydroxyl group (when L is O),
$R^1$ is, independently, $(C_1-C_{10})$alkyl optionally substituted with 1-3 $R^6$, halo, hydroxy, —$NR^3R^4$, —$COOR^2$, —$COR^2$, nitro, trihaloalkyl, or —Si$(OR^2)_3$;
$R^2$ is, independently, H or $(C_1-C_{10})$alkyl;
$R^3$ is, independently, H or $(C_1-C_{10})$alkyl;
$R^4$ is, independently, H or $(C_1-C_{10})$alkyl;
$R^5$ is, independently, $(C_1-C_{20})$alkyl optionally substituted with 1-3 $R^1$, $(C_5-C_{50})$aryl optionally substituted with 1-3 $R^1$, or heteroaryl optionally substituted with 1-3 $R^1$;
$R^6$ is, independently, halo, hydroxy, —$NR^3R^4$, —$COOR^2$, —$COR^2$, nitro, trihaloalkyl, or —Si$(OR^2)_3$; and
Y comprises a covalent bond to a different monomer residue; and
Z comprises a covalent bond to said solid support; and
wherein zero to five R groups comprise covalent bonds to the solid support.

In embodiments of the present invention comprising methods of chromatographic separation, said chromatographic separation is carried out by any method not inconsistent with the objectives of the present invention. In some embodiments of the present invention comprising methods of chromatographic separation, said chromatographic separation is carried out by high pressure liquid chromatography. In other embodiments of the present invention comprising methods of chromatographic separation, said chromatographic separation is carried out by gas liquid chromatography. In still other embodiments of the present invention comprising methods of chromatographic separation, said chromatographic separation is carried out by capillary chromatography. In some embodiments of the present invention comprising methods of chromatographic separation, said chromatographic separation is carried out by packed column gas chromatography. In other embodiments of the present invention comprising methods of chromatographic separation, said chromatographic separation is carried out by supercritical fluid chromatography. In still other embodiments of the present invention comprising methods of chromatographic separation, said chromatographic separation is carried out by capillary electrochromatography.

In some embodiments of the present invention comprising methods of chromatographic separation, the method further comprises providing a mobile phase comprising at least one organic solvent or supercritical fluid. In some embodiments of the present invention comprising methods of chromatographic separation further comprising providing a mobile phase comprising at least one organic solvent or supercritical fluid, said organic solvent is a polar organic solvent.

In preferred embodiments of the present invention comprising methods of chromatographic separation, said chromatographic separation is chiral separation to separate a racemic mixture or other mixture of stereoisomers.

In embodiments of the present invention comprising methods of chromatographic separation comprising providing, as a first stationary phase, a composition comprising a derivatized cyclofructan residue of formula I, any derivatized cyclofructan residue not inconsistent with the objectives of the present invention may be used. In some embodiments of the present invention comprising methods of chromatographic separation comprising providing, as a first stationary phase, a composition comprising a derivatized cyclofructan residue of formula I, at least one of said L in formula I is O—C(=O)—$NR^2$, at least one of said R in formula I is isopropyl, and at least one of said R is a covalent bond to said solid support. In other embodiments of the present invention comprising methods of chromatographic separation comprising providing, as a first stationary phase, a composition comprising a derivatized cyclofructan residue of formula I, at least one of said L in formula I is O—C(=O)—$NR^2$, at least one of said R in formula I is naphthylethyl, and at least one of said R is a covalent bond to said solid support. In still other embodiments of the present invention comprising methods of chromatographic separation comprising providing, as a first stationary phase, a composition comprising a derivatized cyclofructan residue of formula I, at least one of said L in formula I is O—C(=O)—NR², at least one of said R in formula I is 3,5-dimethylphenyl, and at least one of said R is a covalent bond to said solid support.

Stationary phases comprising derivatized or un-derivatized cyclofructans of the present invention can be prepared in a variety of ways. In some embodiments of the present invention, a chiral stationary phase is prepared by chemically bonding a native cyclofructan to silica as described herein and then optionally derivatizing the native cyclofructan as described herein. In other embodiments of the present invention, a chiral stationary phase is prepared by first partially derivatizing a cyclofructan as described herein and then bonding said partially-derivatized cyclofructan to silica as described herein. In some embodiments of the present invention, after a partially derivatized cyclofructan is bonded to a solid support, it is further derivatized to achieve complete derivatization. In other embodiments of the present invention, after a partially derivatized cyclofructan is bonded to a solid support, it is functionalized with a different moiety in order to provide a heterogeneously derivatized cyclofructan.

Embodiments of the present invention comprising methods of chromatographic separation comprising providing, as a first stationary phase, a composition comprising a derivatized cyclofructan residue of formula I, can be useful for the separation of a wide array of analytes, including acids, bases, amino acid derivatives, primary amines, secondary amines, tertiary amines, and others. Some embodiments of the present invention are especially useful for the separation of a wide range of primary amines. Moreover, CF6-based CSPs of the present invention exhibit excellent stability toward common organic solvents, with no detrimental changes in column performance observed after more than 1000 injections. Further, CF6-based CSPs of the present invention can serve as stationary phases for both analytical and preparative scale chromatography.

Not wishing to be bound by theory, it is believed that cyclofructans can be functionalized in accordance with the principles of the present invention so as to provide two different types of chiral selectors which separate enantiomers and other chemical species via two different mechanisms. For example, it is believed that, in some embodiments of the present invention, CF6 that is minimally functionalized with smaller aliphatic moieties has a relaxed structure that exposes its crown ether core and additional hydroxyl groups. Not wishing to be bound by theory, it is believed that this structure allows for interactions with and separation of chiral primary amines in organic solvents, which was not previously possible. In other embodiments of the present invention, CF6 that is more highly derivatized with aromatic moieties has a sterically crowded structure that hinders access to its molecular core but provides ample other interaction sites about its periphery. Again not wishing to be bound by theory, it is believed that these sites provide chiral recognition for a broad range of compounds, in some embodiments.

Further, some embodiments of the present invention comprise a method of capillary electrophoresis comprising providing an electrolyte comprising a composition of formula I to separate chemical species in a mixture.

EXAMPLES

Some exemplary embodiments of the present invention will now be illustrated in the following specific, non-limiting examples. It should be noted that some of the following examples refer to a specific CF starting material or reagent, such as CF6. However, in those instances, CF7 or CF8 could be substituted for CF6 without altering or violating the principles of the present invention. Abbreviations used in the Examples are as follows:

AA=acetic acid
ACN=acetonitrile
CF=cyclofructan
DMF=dimethylformamide
DMSO=dimethylsulfoxide
EDTA=ethylenediaminetetraacetic acid
ESI-MS=electrospray ionization-mass spectrometry
IP=isopropyl
IP—CFn=isopropyl-carbamate-functionalized CFn
MW=molecular weight
RN=(R)-naphthylethyl
RN—CFn=(R)-naphthylethyl-carbamate-functionalized CFn
TEA=triethylamine
TFA=trifluoroacetic acid
THF=tetrahydrofuran Example 1

Synthesis of derivatized cyclofructan residue 4,6-di-O-pentyl-3-trifluoroacetyl CF6

A mixture of CF6 (1.00 g) and anhydrous DMSO (~15 mL) was cooled in an ice bath. Finely ground NaOH (2.03 g) and 1-bromopentane (6.05 g) were added to this mixture and allowed to react for 48 h. After this time, dichloromethane (~60 mL) and water (~60 mL) were added to the mixture. The resulting organic phase was collected twice and washed several times with water. Removal of dichloromethane by rotary evaporation followed by drying in a vacuum oven overnight yielded a yellowish viscous liquid. ESI-MS confirmed that the CF had been pentylated, with an average degree of substitution of 11-12. To produce the trifluoracetyl derivative, the 4,6-di-O-pentyl CF product was treated with a large excess of trifluoroacetic anhydride in dichloromethane. The final product was a liquid.

Example 2

Synthesis of derivatized cyclofructan residue 3,4,6-tri-O-methyl CF6

A dimethyl sulfinyl carbanion solution was prepared by stirring anhydrous DMSO (~5 mL) and NaH (0.864 g) for 30 min at room temperature. Then CF6 (0.600 g) was added to the mixture, and stirring continued at room temperature for 4 h. After that time, the reaction mixture was cooled in an ice bath, and methyl iodide (8.1 mL) was added. The mixture was then stirred at room temperature overnight. Next, the reaction was quenched by the addition of dichloromethane (~50 mL). The collected organic phase was washed with water. Removal of dichloromethane by rotary evaporation followed by drying in a vacuum oven overnight yielded a slightly off-white solid. ESI-MS was used to confirm the product: (m/z) 1247 $(M+Na)^+$.

Example 3

Synthesis of Derivatized Cyclofructan Residue Propylsulfonate CF6 ($CF6-CH_2CH_2CH_2SO_3^-$)

To a solution of CF6 (1 equivalent) in anhydrous DMF, excess NaH (10 equivalents) was added. The resulting mixture was stirred at room temperature for 12 h. Next, 1,3- propane sultone (10 equivalents) was added, followed by stirring at room temperature for 12 h. Excess NaH was then removed by the addition of methanol, yielding the derivatized cyclofructan residue propylsulfonate CF6 (CF6-$CH_2CH_2CH_2SO_3^-$).

Example 4

Synthesis of a Derivatized Cyclofructan Residue with a Carbamate Linker

This Example shows that in some embodiments of the present invention a cyclofructan can be derivatized with a carbamate linker.

In a 100 mL 3-neck flask, 1 g CF6 was dried at 110° C. in an oven for 5 h. Then, 30 mL anhydrous pyridine was added to dissolve the CF6. To the CF6 solution, 0.6 mL 4-methylphenyl isocyanate in 10 mL pyridine was added dropwise under a dry nitrogen atmosphere. Then the mixture was refluxed for 4 h. Once the solution was cooled to room temperature, it was ready for binding to silica according to the procedures described herein.

Example 5

Synthesis of a Derivatized Cyclofructan Residue with an Ester Linker

This Example shows that in some embodiments of the present invention a cyclofructan can be derivatized with an ester linker.

In a 100 mL 3-neck flask, 1 g CF6 was dried at 110° C. in an oven for 5 hours. Then, 30 mL anhydrous pyridine was added to dissolve the CF6. To the CF6 solution, 0.6 mL p-toluoyl chloride in 10 mL pyridine was added dropwise under a dry nitrogen atmosphere. Then the mixture was refluxed for 4 h. Once the solution was cooled to room temperature, it was ready for binding to silica according to the procedures described herein.

Example 6

Synthesis of a Derivatized Cyclofructan Residue with an Ether Linker

This Example shows that in some embodiments of the present invention a cyclofructan can be derivatized with an ether linker.

In a 100 mL flask, 1 g CF6 was dried at 110° C. in an oven for 5 hours. Then, 30 mL anhydrous DMF was added to dissolve the CF6 by stirring under an argon atmosphere. Next, 0.2 g NaH was added into the solution, and the temperature was raised slowly to 70° C. and kept there for 30 min. Under argon protection, 1 g 1-chloro-2,4-dinitrobenzene was added, and the mixture was heated at 100° C. for 5 h. The resulting salt was removed by filtration, and DMF was removed by rotary evaporation. The product was washed with 3×100 mL diethyl ether, and the brown solid product was filtered and dried. The derivatized CF6 was then ready to be bonded to silica according to the procedures described herein.

In addition to Examples 1-6, numerous other derivatized cyclofructan residues were prepared. Table 2 lists some examples of derivatized cyclofructan residues of the present invention.

TABLE 2

Some derivatized cyclofructan residues of the present invention.

| Derivative type | R = |
|---|---|
| Cyclofructan carbamate 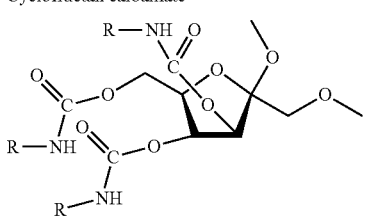 | —$CH_3$ 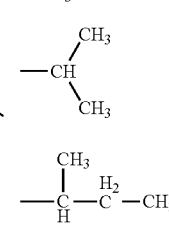 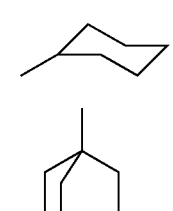 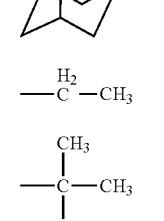 |

TABLE 2-continued
Some derivatized cyclofructan residues of the present invention.
| Derivative type | R = |
|---|---|
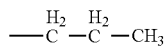
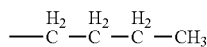
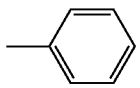
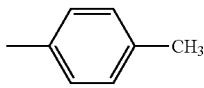
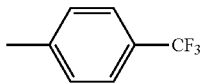
X = Cl, Br, or I
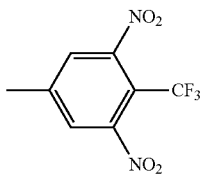 [SMILES: Cc1cc([N+](=O)[O-])c(C(F)(F)F)c([N+](=O)[O-])c1]
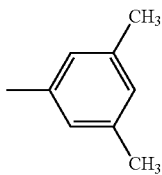
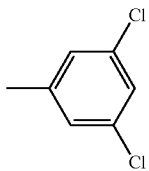
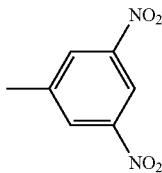
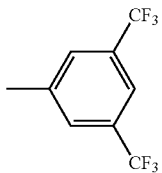

TABLE 2-continued
Some derivatized cyclofructan residues of the present invention.
| Derivative type | R = |
|---|---|
| | 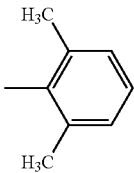 |
| | 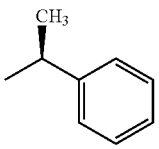 |
| | 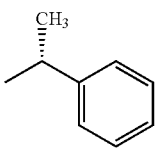 |
| | 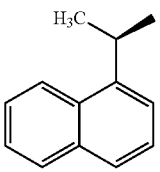 |
| | 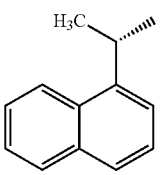 |
| | 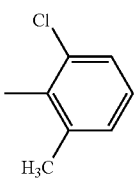 |
| | 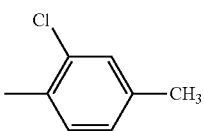 |
| | 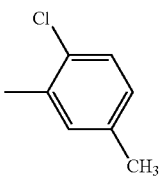 |
| | 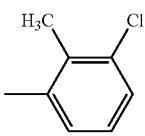 |

TABLE 2-continued
Some derivatized cyclofructan residues of the present invention.
| Derivative type | R = |
|---|---|
| | 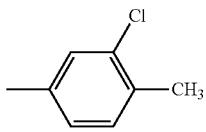 |
| | 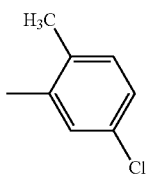 |
| Cyclofructan ester 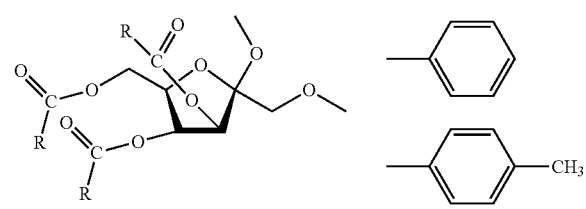 | —CH₃ |
| | 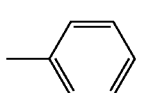 |
| | 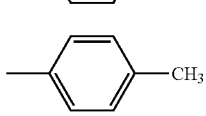 |
| |  |
| | 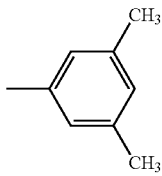 |
| | 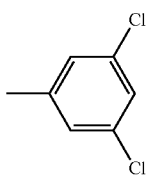 |
| Cyclofructan ether 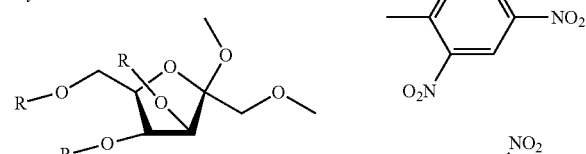 | 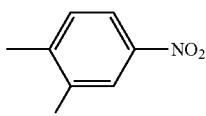 |
| | 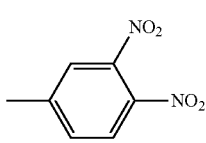 |
| | 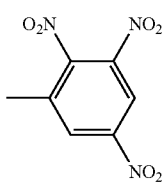 |

TABLE 2-continued

Some derivatized cyclofructan residues of the present invention.

| Derivative type | R = |
|---|---|
| | 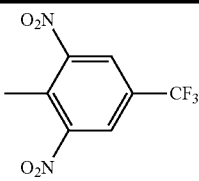 |
| | 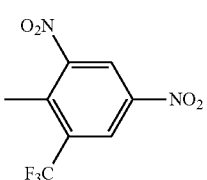 |
| | 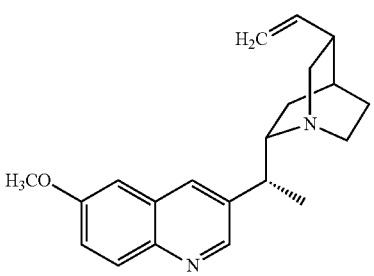 |

Example 7

Preparation of a Silica-Bonded Cyclofructan Residue Through an Ether Linkage

The procedures for chemically bonding un-derivatized (or "native") cyclofructans are essentially the same as those for bonding various derivatized cyclofructans. For the sake of illustration purposes only, the preparation of a silica-bonded un-derivatized cyclofructan residue is presented here as an example. A person of ordinary skill in the art will understand, however, that a similar procedure would allow the preparation of a silica-bonded derivatized cyclofructan residue.

In a 250 mL 3-neck flask, 3 g silica gel (Kromasil, 5 μm spherical diameter, 100-1000 Å pore diameter) was dried at 110° C. for 3 h. Anhydrous toluene (150 mL) was added, and any remaining water was removed using a Dean-Stark trap. The resulting mixture was cooled to <40° C., and 1.3 mL 3-glycidoxypropyltrimethoxysilane was added. The mixture was heated at 100° C. for 5 h. The mixture was then cooled and filtered. The solid product was washed with 20 mL toluene, acetonitrile, methanol, and acetone. The resulting epoxy-functionalized silica was dried in a vacuum oven overnight.

Separately, 1 g CF6 was dried at 110° C. for 5 hours and then dissolved in 30 mL anhydrous DMF in a 100 mL round flask by stirring. Then 0.2 g NaH was added to the solution under a dry argon atmosphere and stirred for 10 min. Unreacted NaH was removed by vacuum filtration. Next, 3.3 g dry epoxy-functionalized silica was added to the filtrate in a 100 mL round flask. Then the mixture was heated at 140° C. for 3 h. The mixture was then cooled and filtered. The solid product was washed with 20 mL DMF, acetonitrile, methanol, and acetone. The resulting silica-bonded CF residue was then dried in a vacuum oven overnight, yielding 3.5 g product.

Example 8

Preparation of a Silica-Bonded Cyclofructan Residue Through a Carbamate Linkage Using Diisocyanate Cyclofructans can be bonded to silica gel through a carbamate linkage in at least two ways. This Example describes one method, while Example 9 describes another method. Further, it should be noted that this Examples uses 1,6-diisocyanatohexane. But other diisocyanates, with different distances between the two isocyanate groups, could also be used, such as 4,4'-methylenediphenyl diisocyanate and 1,4-phenylene diisocyanate. In addition, the procedures for chemically bonding un-derivatized (or "native") cyclofructans are essentially the same as those for bonding various derivatized cyclofructans. For the sake of illustration purposes only, the preparation of a silica-bonded un-derivatized cyclofructan residue is presented here as an example. A person of ordinary skill in the art will understand, however, that a similar procedure would allow the preparation of a silica-bonded derivatized cyclofructan residue.

In a 250 mL 3-neck flask, 3 g silica gel (Kromasil, 5 μm spherical diameter, 100-1000 Å pore diameter) was dried at 110° C. for 3 h. Anhydrous toluene (150 mL) was added, and any remaining water was removed using a Dean-Stark trap. The resulting mixture was cooled to <40° C., and 1 mL 3-aminopropyltriethoxysilane was added dropwise. The mixture was refluxed for 4 h. The mixture was then cooled and filtered. The solid product was washed with acetonitrile, methanol, and acetone. The solid product was then dried under vacuum overnight, yielding 3.3 g amino-functionalized silica.

In a 250 mL flask, 180 mL anhydrous toluene was added to dry 3.3 g amino-functionalized silica, and residual water was removed using a Dean-Stark trap. The mixture was cooled to room temperature, and 2 mL 1,6-diisocyanatohexane was added to the dry amino-silica toluene slurry, which was kept in an ice bath. Then the mixture was heated at 70° C. for 4 h. The mixture was then cooled and vacuum filtered. The solid product was washed with 20 mL anhydrous toluene twice. Then 1 g dried CF6 dissolved in 20 mL pyridine was added, and the mixture was heated at 70° C. for 15 h. The mixture was then cooled and filtered. The solid product was washed with pyridine, acetonitrile, methanol, and acetone and dried under vacuum overnight. 3.7 g of product was obtained.

Example 9

Preparation of a Silica-Bonded Cyclofructan Residue Through a Carbamate Linkage Using Isocyanate Silane Cyclofructans can be bonded to silica gel through a carbamate linkage in at least two ways. This Example describes one method, while Example 8 describes another method. Further, the procedures for chemically bonding un-derivatized (or "native") cyclofructans are essentially the same as those for bonding various derivatized cyclofructans. For the sake of illustration purposes only, the preparation of a silica-bonded un-derivatized cyclofructan residue is presented here as an example. A person of ordinary skill in the art will understand, however, that a similar procedure would allow the preparation of a silica-bonded derivatized cyclofructan residue.

In a 100 mL 3-neck round flask, 1 g CF6 was dried at 110° C. for 5 hours. Then 40 mL anhydrous pyridine was added with stirring. Next, 0.7 mL 3-(triethoxysilyl)propyl isocyanate was added to the solution dropwise under a dry argon atmosphere. The mixture was then heated at 90° C. for 5 h. In a 250 mL 3-neck flask, 3 g silica gel (Kromasil, 5 µm spherical diameter, 100-1000 Å pore diameter) was dried at 110° C. for 3 h. Anhydrous toluene (150 mL) was added, and any remaining water was removed using a Dean-Stark trap. After both mixtures were cooled to room temperature, the cyclofructan mixture was added to the silica-toluene slurry and heated at 105° C. overnight. The final mixture was then cooled and filtered. The solid product was washed with acetonitrile, methanol, and acetone. After drying in a vacuum oven overnight, 3.4 g of product was obtained.

Example 10

Preparation of a Silica-Bonded Cyclofructan Residue Through the Reaction of an Aldehyde Functional Group with a Hydroxyl Functional Group Silica was functionalized with an epoxy group according to the procedure described in Example 6. To 3.5 g epoxy-functionalized silica, 100 mL 0.01 M HCl aqueous solution was added. The resulting mixture was heated at 90° C. for 3 h. The mixture was then cooled and filtered. The solid product was washed with water, methanol and acetone and then dried in a vacuum oven overnight. 3.5 g diol-functionalized silica was obtained. 100 mL 60 mM sodium periodate in water/methanol (4:1) was added to the diol-functionalized silica and stirred for 12 h at room temperature. The resulting aldehyde-functionalized silica was filtered, washed, and dried. Then, 1 g CF6, 3.5 g aldehyde-functionalized silica, and 100 mL toluene with HCl bubbled into it were mixed and refluxed overnight. The mixture was then cooled and filtered. The solid product was washed and dried. Then, 50 mL 20 mM sodium cyanoborohydride ($NaCNBH_3$) in phosphate buffer (pH=3) was added to the solid product and stirred for 5 h at room temperature, in order to reduce the remaining aldehyde moieties. Then the solid product was filtered and washed with water, methanol, acetonitrile, and acetone.

Example 11

Preparation of a Silica-Bonded Cyclofructan Residue Through a 1,3-dipolar Cycloaddition Reaction (Click Chemistry)

This Example shows that 1,3-dipolar cycloaddition reactions of azides and alkynes can be used to attach un-derivatized and derivatized cyclofructans to silica gel. In some embodiments of the present invention, the silica gel can be modified with azide functional groups, while the cyclofructan is derivatized with alkynes before the click reaction. In other embodiments, the silica gel can be modified with alkynes, while the cyclofructan is derivatized with azide functional groups. In this Example, for illustration purposes only, alkyne-functionalized silica gel reacts with azide-modified cyclofructan to afford the covalently bonded cyclofructan stationary phase.

Two grams of CF6 and 2 g NaOH are suspended in 200 mL water. 4.2 g p-toluenesulfonyl chloride in 10 mL acetonitrile is added dropwise to the CF6 solution. After 2 h reaction at room temperature with magnetic stirring, the precipitate is removed by filtration, and the filtrate is kept in the refrigerator overnight. The resulting precipitate is recovered by filtration and vacuum dried to afford 2.5 g product (mono-6-deoxy-6-(p-tolylsulfonyl)-CF6) The product (2 g) is then suspended in 6 mL dry N,N'-dimethylformamide and heated to 65° C. Then, 0.15 g potassium iodide and 1.0 g sodium azide are added, and the reaction mixture is stirred at 65° C. for 24 h. The mixture is then cooled to room temperature and treated with Amberlite MB-3 resin to remove salts. Acetone is added to produce a white precipitate, which is recovered by filtration and vacuum dried overnight to afford 1.4 g product (mono-6-deoxy-6-azido-CF6).

Ten grams of 3-isocyanatopropyltriethoxysilane is dissolved in 100 mL anhydrous DMF, 3 g propargylamine is added to the solution, and the reaction mixture is heated to 80° C. for 12 h with magnetic stirring. Then, 10 g pre-dried silica gel (4 h in 110° C. oven) is added to the reaction mixture after it cools to room temperature. The suspension is stirred for 16 h at 95° C. to afford the alkyne-modified silica gel. The product is filtered and washed with DMF, methanol, and acetone before it is vacuum dried overnight.

Next, 1.5 g mono-6-deoxy-6-azido-CF6, 0.1 g sodium ascorbate, 0.025 g copper sulfate, and 3.0 g alkyne-modified silica gel are suspended in 120 mL 50% (v/v) aqueous methanol solution and stirred for 72 h at room temperature. The resulting product is filtered and washed with methanol, water, 10% EDTA, water, methanol, and acetone successively, and then vacuum dried to afford the covalently attached cyclofructan.

Example 12

Preparation of a Silica-Bonded Cyclofructan Residue Through Mixed Derivatives on Cyclofructan First, 1 g dried CF6 was dissolved in 30 mL anhydrous pyridine. Then, 2 g 10-undecenoyl chloride was added with stirring. The mixture was refluxed for 2 h. Then 1.6 g 3,5-dimethylphenyl isocyanate was added under a dry argon atmosphere. Then the mixture was refluxed for 2 h. After the mixture was cooled to room temperature, solvent was removed by rotary evaporation. The solid product was washed with chloroform and ethanol. The resulting derivatized cyclofructan was then dissolved in acetone and bonded on 3.5 g allysilica gel. After evaporating the solvent, 0.1 g AIBN (α,α'-azobisisobutyronitrile) was added, and the solid material was allowed to react for 2 h at 100° C. Then the solid was suspended in chloroform and heated to reflux for 2 h. After the reaction mixture cooled to room temperature, the solid silica was filtered and washed with chloroform and acetone.

Example 13

Derivatization of a Silica-Bonded Cyclofructan with Carbamate Linker

This Example, as well as Examples 14 and 15, shows that in some embodiments of the present invention, a cyclofructan can be first bonded to silica and then later derivatized to form a silica-bonded derivatized cyclofructan. In this Example, the cyclofructan features a carbamate linker.

3.5 g CF6-bonded silica (prepared as described herein) was dried overnight under vacuum. The material was placed in a 3-neck 250 mL flask, and 150 mL anhydrous pyridine was added to the flask. Residual water was removed using a Dean-Stark trap. Then, 1.3 mL 4-methylphenyl isocyanate was added. The resulting mixture was refluxed for 4 h. When the mixture was cooled to room temperature, it was filtered. The solid product was washed with pyridine, acetonitrile, water, methanol and acetone, and dried under vacuum overnight, yielding 3.8 g product.

Example 14

Synthesis of a Silica-Bonded Derivatized Cyclofructan with Ester Linker

This Example, as well as Examples 13 and 15, shows that in some embodiments of the present invention, a cyclofructan can be first bonded to silica and then later derivatized to form a silica-bonded derivatized cyclofructan. In this Example, the cyclofructan features an ester linker.

3.5 g CF6-bonded silica (prepared as described herein) was dried overnight under vacuum. The material was placed in a 3-neck 250 mL flask, and 150 mL anhydrous pyridine was added to the flask. Residual water was removed using a Dean-Stark trap. Then, 0.8 mL p-toluoyl chloride was added. The resulting mixture was refluxed for 4 h. When the mixture was cooled to room temperature, it was filtered. The solid product was washed with pyridine, acetonitrile, water, methanol, and acetone, and dried under vacuum overnight, yielding 3.8 g product.

Example 15

Synthesis of a Silica-Bonded Derivatized Cyclofructan with Ether Linker

This Example, as well as Examples 13 and 14, shows that in some embodiments of the present invention, a cyclofructan can be first bonded to silica and then later derivatized to form a silica-bonded derivatized cyclofructan. In this Example, the cyclofructan features an ether linker.

3.5 g CF6-bonded silica (prepared as described herein) was dried overnight under vacuum. The material was placed in a 3-neck 250 mL flask and 40 mL anhydrous DMF was added. Also, 0.1 g NaH was added with stirring under argon protection. After stirring for 30 min at room temperature, 4-chloro-3,5-dinitrobenzotrifluoride (0.27 g) was added. The mixture was heated at 100° C. for 5 h. The mixture was cooled to room temperature and filtered. The solid product was washed with DMF, acetonitrile, water, methanol, and acetone, and dried under vacuum overnight, yielding 3.7 g brown product.

Example 16

Synthesis of Completely Derivatized-Cyclofructan Stationary Phases

In a 100 mL 3-neck flask, 1 g CF6 was dried at 110° C. in an oven for 5 hours. Then, 30 mL anhydrous pyridine was added to dissolve the CF6. Next, 1.0 mL 3,5-dimethylphenyl isocyanate in 10 mL pyridine was added to the cyclofructan solution dropwise under dry nitrogen protection. Then the mixture was refluxed for 4 h. When the solution was cooled to room temperature, 0.7 mL 3-(triethoxysilyl)propyl isocyanate dissolved in 10 mL pyridine was added to the solution dropwise under dry argon protection. Then the mixture was heated at 90° C. for 5 h.

At the same time, in a 250 mL 3-neck flask, 3 g silica gel (Kromasil, 5 μm spherical diameter, 100-1000 Å pore diameter) was dried at 110° C. for 3 h. Anhydrous toluene (150 mL) was added, and any remaining water was removed using a Dean-Stark trap.

Then the two mixtures were cooled to room temperature, and the cyclofructan mixture was poured into the silica-toluene slurry and heated at 105° C. overnight. The resulting mixture was then cooled and filtered. The solid product was washed with acetonitrile, methanol, and acetone, and dried in a vacuum oven overnight, yielding 3.5 g product. The product was then placed in a 3-neck 250 mL flask, to which 150 mL anhydrous pyridine was added. Residual water was removed using a Dean-Stark trap. Then, 1.8 mL 3,5-dimethylphenyl isocyanate was added. The mixture was refluxed for 4 h. When the solution was cooled to room temperature, it was filtered. The solid product was washed with pyridine, acetonitrile, water, methanol, and acetone, and dried under vacuum overnight, yielding 3.8 g product.

Example 17

Synthesis of a Cyclofructan Analogue with Two Different Derivatizing Groups

This Example describes the procedures for derivatizing CF6 with dinitrophenyl and dimethylphenyl groups. In a 100 mL flask, 1 g CF6 was dried at 110° C. oven for 5 hours. Then the CF6 was dissolved by 30 mL anhydrous DMF with stirring under argon protection. Next, 0.2 g NaH was added into the solution, and the temperature was raised slowly to 70° C. and kept there for 30 min. Under argon protection, 1 g 1-chloro-2,4-dinitrobenzene was added, and the mixture was heated at 100° C. for 5 h. The salt was removed by filtration and DMF was removed by rotary evaporation. Then the resulting solid product was washed with 3×100 mL diethyl ether. The resulting brown solid was filtered and dried. Then, 1.3 g product was dissolved in 30 mL pyridine. Then 0.7 mL 3-(triethoxysilyl)propyl isocyanate dissolved in 10 mL pyridine was added to the solution dropwise under dry argon protection. The mixture was heated at 90° C. for 5 h.

At the same time, in a 250 mL 3-neck flask, 3 g silica gel (Kromasil, 5 μm spherical diameter, 100-1000 Å pore diameter) was dried at 110° C. for 3 h. Anhydrous toluene (150 mL) was added, and any remaining water was removed using a Dean-Stark trap. The two mixtures were cooled to room temperature, and the cyclofructan reaction mixture was added to the silica-toluene slurry and heated at 105° C. overnight. The final mixture was cooled and filtered. The solid product was washed with acetonitrile, methanol, and acetone, and dried in a vacuum oven overnight, yielding 3.6 g product. Then solid product was then placed in a 3-neck 250 mL flask, to which 150 mL anhydrous pyridine was added. Residual water was removed using a Dean-Stark trap. Then, 1.8 ml 3,5-dimethylphenyl isocyanate was added. The mixture was refluxed for 4 h. When the solution was cooled to room temperature, it was filtered and washed with pyridine, acetonitrile, water, methanol and acetone. After drying under vacuum overnight, 3.9 g product was obtained.

Example 18

Synthesis of a Polymeric Cyclofructan Through Carbamate Linkers and Preparation of a Polymeric CSP Incorporating the Polymeric Cyclofructan This Example, as well as Examples 19-24, describes the synthesis of a polymeric CF and the preparation of a CSP incorporating the polymeric CF. Although some of Examples 18-24 describe the preparation of native CF polymers and CSPs containing such polymeric CFs, derivatized CF polymers and CSPs can be prepared similarly, substituting native CFs with derivatized CFs.

Hexamethylene diisocyanate (1-12 equivalents) and CF6 (1 equivalent) are dissolved in dried DMF, giving a CF:crosslinker molar ratio ranging from 1:12 to 1:1, and heated at 80° C. for 24-28 h. The resulting polymer is precipitated in a large amount of methanol, separated by filtering, and dried in vacuo at 50° C. for 24 h. The dried polymeric CF is coated on a 3-aminopropyltriethoxylsilyl functionalized macroporous silica gel, yielding a polymeric CSP incorporating the polymeric CF.

Example 19

Synthesis of a Polymeric Cyclofructan Through Ether Linkers and Preparation of a Polymeric CSP Incorporating the Polymeric Cyclofructan Native CF6 (1 equivalent) is stirred in a concentrated sodium hydroxide solution for 4 h. The solution is then heated to 30° C., and the epichlorohydrin crosslinker (1-12 equivalents) is added rapidly. The reaction is kept at 30° C. for 5 h and then stopped by addition of acetone. Acetone is subsequently removed via decantation. The solution is then neutralized with hydrochloric acid and diafiltered under pressure. The remaining solvent was evaporated, and the remaining solid triturated with acetone. The polymer is separated by filtration and dried in vacuo at 50° C. for 24 h. The CF polymer (MW ~25,000 g/mol) is then coated on a 3-aminopropyltriethoxylsilyl functionalized macroporous silica gel, yielding a polymeric CSP incorporating the polymeric CF.

Example 20

Synthesis of a Polymeric Methacrylate-Functionalized Cyclofructan and Preparation of a Polymeric CSP Incorporating the Polymeric Methacrylate-Functionalized Cyclofructan Methacrylate-functionalized CF6 (CF6-MA; 1 equivalent) and 1-vinyl-2-pyrrolidinone (VP; 1-12 equivalents) are dissolved into deionized water, and the resulting solution is maintained at 80° C. The initiator potassium persulfate ($K_2S_2O_8$) is then added, and the resulting mixture is stirred for 24 h. The lower molecular weight CF6-MA polymers thus obtained are dialysed against water and then freeze-dried; the higher molecular weight CF6-MA polymer gels obtained are filtered, washed, and dried in vacuo at 50° C. for 24 h. The purified and dried higher molecular weight CF6-MA polymer is then coated or bonded onto unfunctionalized silica gel, yielding a polymeric CSP incorporating the polymeric CF6-MA.

Example 21

Preparation of a Polymeric CSP Incorporating a Norbornene-Functionalized Cyclofructan Silica gel and norborn-2-ene-5-yltrichlorosilane are heated in toluene to afford a surface-bound copolymerizable norborn-2-ene group. The initiator $Cl_2Ru(=CHPh)(PCy_3)_2$, where Cy=cyclohexyl, is then added, reacting with surface-bound norborn-2-ene groups. Finally, norbornene-substituted CF6 is added to the heterogenized initiator and becomes grafted onto the silica gel surface, yielding a polymeric CSP incorporating CF6.

Example 22

Synthesis of a polymeric 3-chloro-2-hydroxypropyl-functionalized cyclofructan and preparation of a polymeric CSP incorporating the polymeric 3-chloro-2-hydroxypropyl-functionalized cyclofructan Examples 22 and 23 together demonstrate two different methods for forming a CSP incorporating polymeric 3-chloro-2-hydroxypropyl-functionalized cyclofructan. In Example 22, a monomeric 3-chloro-2-hydroxypropyl-functionalized cyclofructan is first synthesized and then linked to a polyvinylimidazole, which is then used to prepare a CSP.

A 3-chloro-2-hydroxypropyl CF6 derivative is prepared by reacting CF6 with epichlorohydrin in acidic medium in the presence of zinc tetrafluoroborate ($Zn(BF_4)_2$) at 80° C. for several hours. The product is covalently linked to polyvinylimidazole (MW=8000) by heating under reflux with water for several hours. The resulting polymer is coated or bonded onto unfunctionalized silica gel.

Example 23

Preparation of a polymeric CSP incorporating 3-chloro-2-hydroxypropyl-functionalized cyclofructan Examples 22 and 23 together demonstrate two different methods for forming a CSP incorporating polymeric 3-chloro-2-hydroxypropyl-functionalized cyclofructan. In Example 23, a monomeric 3-chloro-2-hydroxypropyl-functionalized cyclofructan is linked to a polyvinylimidazole previously coated or bonded onto a silica, so that addition of the derivatized CF constitutes the final step in the preparation of the CSP.

Polyvinylimidazole (PVI; MW=8000) is first coated or bonded onto unfunctionalized silica gel. The resulting PVI-coated or -bonded silica support is suspended in 0.1 M, pH 7.4 phosphate buffer and heated. A 3-chloro-2-hydroxypropylfunctionalized CF6 is then added, and the mixture is heated to and maintained at 100° C. for 48 h. The final product is filtered and washed with water and ethanol, and then dried in vacuo at 50° C. for 24 h.

Example 24

Preparation of a Polymeric CSP Incorporating 6-O-(p-tosyl)-functionalized Cyclofructan This Example demonstrates a method for forming a CSP similar to the method described in Example 23, but using a different functionalized-CF derivative and a different polymer.

Poly(ethyleneimine) (PEI) is coated or bonded onto unfunctionalized silica gel. The resulting PEI-coated or -bonded silica support is suspended in a methanol/dimethylacetamide 2/1 (v/v) mixture solvent. A 6-O-(p-tosyl)-functionalized CF6 is then added, and the mixture is heated to and maintained at 50° C. for 48 h. The final product is filtered and washed with methanol and acetone, and then dried in vacuo at 50° C. for 24 h.

Example 25

Preparation of a Gas Chromatography Column Incorporating a Polymeric CSP Incorporating 3,4,6-tri-O-(methyl)-functionalized Cyclofructan This Example demonstrates a static coating method for forming a chromatography column incorporating a CSP of the present invention.

Derivatized CF residue 3,4,6-tri-O-methyl CF6 is prepared as described herein. It is determined that a mixture of 14% cyanopropylphenyl and 86% methyl polysioloxane could dissolve a sufficient amount of the derivatized CF residue. Next, 2.5 mg 3,4,6-tri-O-methyl CF6 and 22.5 mg methyl polysiloxane are dissolved in 10 mL dichloromethane along with cyanopropylphenyl to produce a coating solution that is used to fill an untreated fused silica capillary (10 m×250 µm). Once the capillary is filled, one end is sealed tightly, and the other end is connected to a vacuum pump. The capillary is then placed in a water bath (40° C.), and vacuum is applied so that the solvent is removed, leaving a uniform film of the stationary phase (3,4,6-tri-O-methyl CF6/14% cyanopropylphenyl/86% methyl polysiloxane) on the wall of the capillary. After the coating is finished, the column is conditioned in a gas chromatograph under helium flow and elevated temperatures, forming a chromatography column incorporating a polymeric CSP incorporating 3,4,6-tri-O-(methyl)-functionalized cyclofructan.

Example 26

Liquid Chromatographic Separation of Chiral Analytes in Different Modes Using a Column Bonded with a CSP Including (R)-1-isopropylnaphthalene-functionalized CF6

Figure 3:
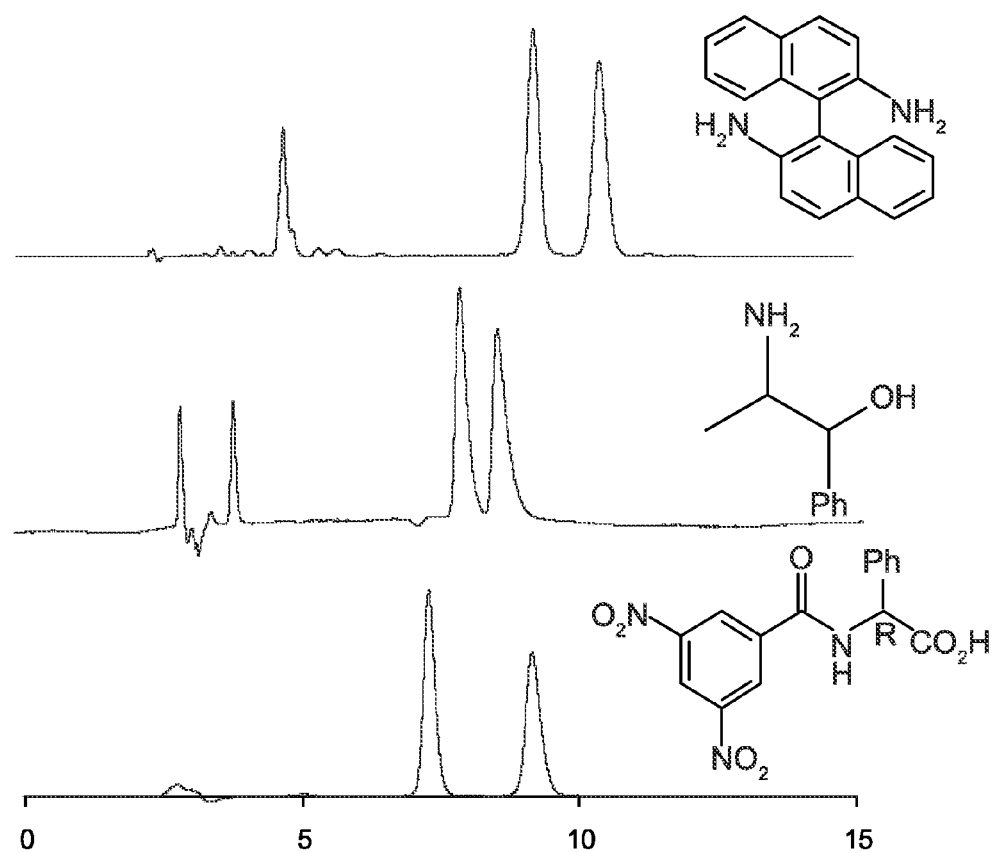
FIG. 3 is a liquid chromatogram showing the results of using a column bonded with a CSP including a functionalized cyclofructan of the present invention to separate chiral analytes in the normal phase mode (top curve), polar organic mode (middle curve), and reversed phase mode (bottom curve).

This Example demonstrates the efficacy of a derivatized CF for achieving chiral separations using liquid chromatography. As shown in FIG. 3, a column bonded with a CSP including (R)-1-isopropylnaphthalene-functionalized CF6 is effective for separating chiral analytes in the normal phase mode (top curve), the polar organic mode (middle curve), and reversed phase mode (bottom curve). The mobile phase in the normal phase mode was 70% heptane/30% ethanol. The mobile phase in polar organic mode was 60% acetonitrile/40% methanol/0.3% acetic acid/0.2% triethylamine.

Example 27

Supercritical Fluid Chromatographic (SFC) Separation of Enantiomeric 1,2-diphenylepoxide Using a Column Bonded with a CSP Including (R)-1-isopropylnaphthalene-functionalized CF6

Figure 4:
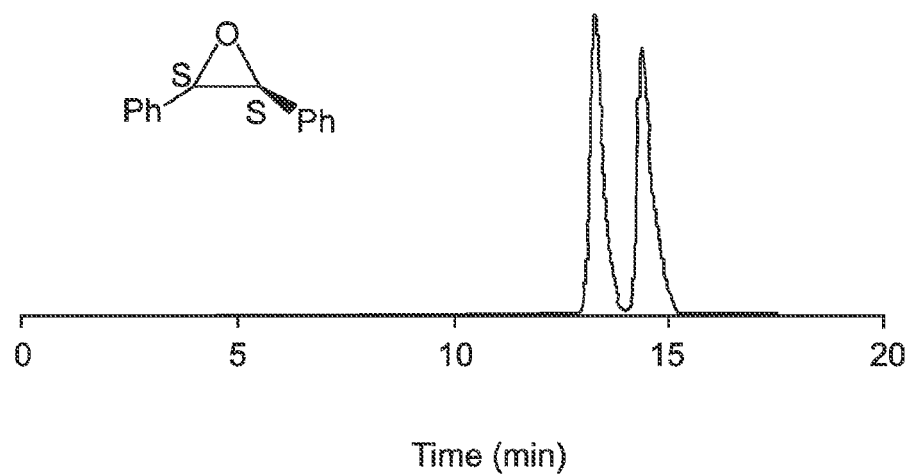
FIG. 4 is a supercritical fluid chromatogram showing the results of using a column bonded with a CSP including a functionalized cyclofructan of the present invention to separate chiral analytes.

This Example demonstrates the efficacy of a derivatized CF for achieving chiral separations using supercritical fluid chromatography. As shown in FIG. 4, a column bonded with a CSP including (R)-1-isopropylnaphthalene-functionalized CF6 is effective for separating enantiomeric 1,2-diphenylepoxide into the (S,S) and (R,R) enantiomers. The mobile phase was 95% carbon dioxide and 5% methanol.

Example 28

Hydrophilic Interaction Liquid Chromatographic (HILIC) Separation of Salicylic Acid Related Compounds Using a Column Bonded with a CSP Including Propylsulfonate-Functionalized CF6.

Figure 5:
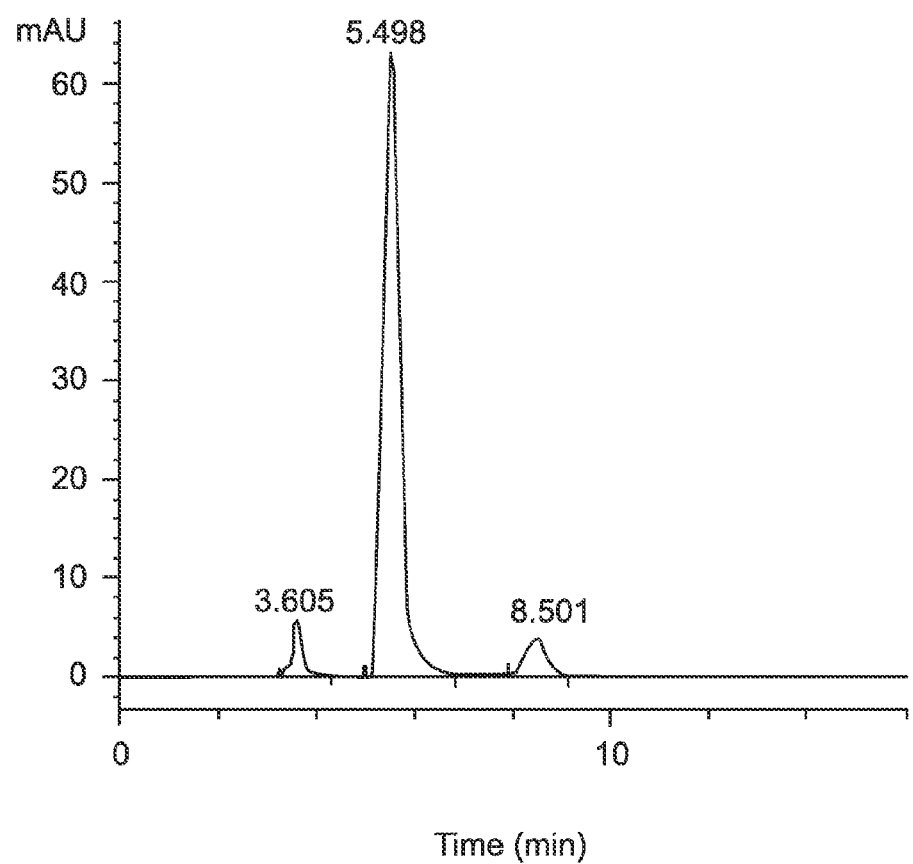
FIG. 5 is a hydrophilic interaction liquid chromatogram showing the results of using a column bonded with a CSP including a functionalized cyclofructan of the present invention to separate salicylic acid, 4-aminosalicylic acid, and acetylsalicylic acid.

This Example demonstrates the efficacy of a derivatized CF for achieving separation of several salicyclic acid related compounds using hydrophilic interaction liquid chromatographic (HILIC). As shown in FIG. 5, a column bonded with a CSP including propylsulfonate-functionalized CF6 is effective for separating salicylic acid, 4-aminosalicylic acid, and acetylsalicylic acid. The mobile phase was 93% acetonitrile and 7% ammonium acetate buffer (pH=4.2).

Example 29

Liquid chromatographic separation of enantiomeric sulfone in polar organic mode using a column bonded with a CSP including propylsulfonate-functionalized CF6.

Figure 6:
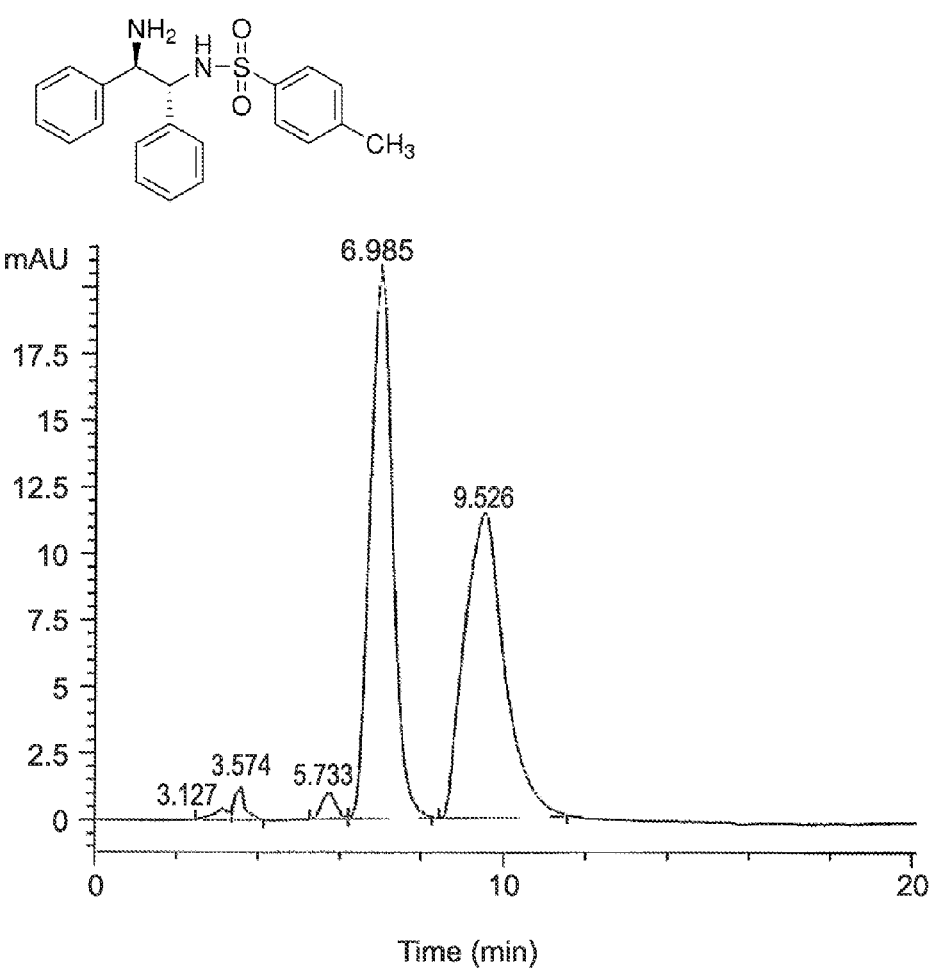
FIG. 6 is a liquid chromatogram showing the results of using a column bonded with a CSP including a functionalized cyclofructan of the present invention to separate chiral analytes.

This Example demonstrates the efficacy of a derivatized CF for achieving enantiomeric separation of a sulfone in polar organic mode. As shown in FIG. 6, a column bonded with a CSP including propylsulfonate-functionalized CF6 is effective for separating the enantiomers of a sulfone. The mobile phase was 90% methanol, 10% acetonitrile, and 0.1% acetic acid.

Example 30

Liquid Chromatographic Separation of Enantiomeric Primary Amines Using a Column Bonded With a CSP Including Native, Isopropyl-Functionalized, and RN—CF6

Figure 7A:
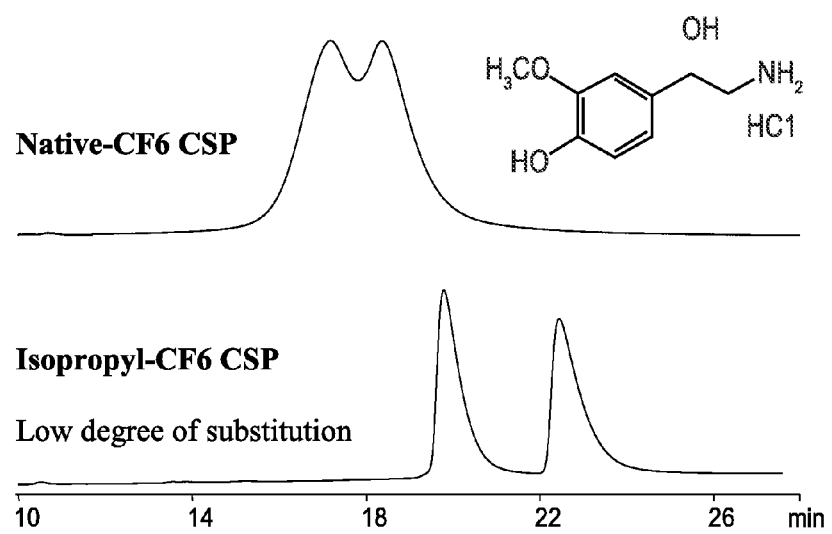
FIG. 7A is a series of liquid chromatograms showing the results of using a column bonded with a CSP including a functionalized cyclofructan of the present invention to separate chiral analytes.
Figure 7B:
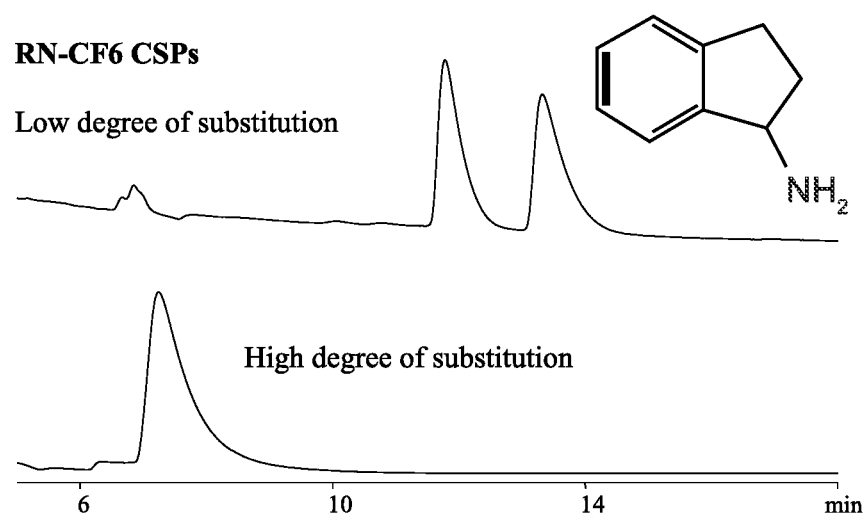
FIG. 7B is a series of liquid chromatograms showing the results of using a column bonded with a CSP including a functionalized cyclofructan of the present invention to separate chiral analytes.

This Example demonstrates the improved efficacy of a functionalized CF6 even only partially substituted with isopropyl groups compared to a native CF6, as shown in FIG. 7A. However, this Example also shows that further increases in the substitution degree on the CF6 molecule results in significantly worse capabilities for separating primary amines, as shown in FIG. 7B. Analytes and mobile phases were as follows: FIG. 7A: normetanephrine hydrochloride, 75% ACN/25% MeOH/0.3% AA/0.2% TEA (top curve), 60% ACN/40% MeOH/0.3% AA/0.2% TEA (bottom curve); FIG. 7B: 1-aminoindan, 60% ACN/40% MeOH/0.3% AA/0.2% TEA (top and bottom curves).

Example 31

Effect of Additives on the Liquid Chromatographic Separation of Enantiomers Using a Column Bonded with a CSP Including a Functionalized CF

This Example shows the effect of acid and basic additives on the separation of primary amines in polar organic mode. To evaluate the effects of acidic and basic additives in the polar organic mode on the separation of primary amines, different types and amounts of basic additives were investigated. The results are shown in Table 3. The highest enantioselectivity was obtained using the combination of triethylamine and acetic acid as additives. Also, the ratio of acidic/basic additives has been optimized and it was determined that addition of 0.3% acetic acid/0.2% triethylamine commonly results in the highest selectivity.

Figure 8:
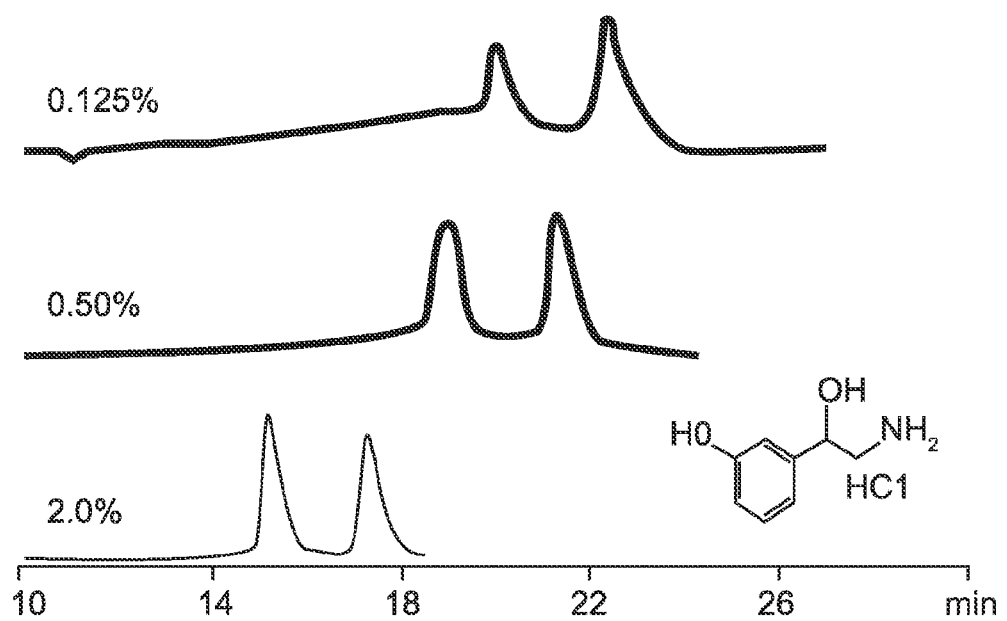
FIG. 8 is a series of liquid chromatograms showing the results of using a column bonded with a CSP including a functionalized cyclofructan of the present invention to separate chiral analytes, wherein the percentage of additives varies from 0.125 to 0.50 to 2.0.

The effect of the total concentration of AA and TEA also was investigated. When the concentration ratio was kept the same, the total concentration was varied as 0.125%, 0.5%, and 2.0%, respectively. As shown in FIG. 8, increasing the total concentration of additives gave rise to sharper and more symmetric peaks by decreasing peak fronting or tailing. This Example thus shows that enantiomeric separations can be improved by changing the total concentration of additives, especially when asymmetric peaks are observed.

TABLE 3

Effect of additive on the separation of (±) trans-1-amino-2-indanol (primary amine) in polar organic mode on an IP-CF6 column.

| | | $k_1$ | α | Rs |
|---|---|---|---|---|
| Change type of basic additive[a] | triethylamine | 2.85 | 1.31 | 4.0 |
| | trimethylamine | 3.36 | 1.29 | 5.3 |
| | ethanolamine | 1.97 | 1.14 | 2.6 |
| | butylamine | 2.36 | 1.16 | 2.3 |
| | diethylamine | 3.67 | 1.29 | 1.6 |
| Change additive amount ratio[b] | 0.30 AA/0.20 TEA | 2.85 | 1.31 | 4.0 |
| | 0.20 AA/0.30 TEA | 2.69 | 1.24 | 3.9 |
| | 0.25 AA/0.25 TEA | 3.24 | 1.27 | 4.4 |

[a]The mobile phase was composed of 60% acetonitrile/40% methanol/0.3% acetic acid (equals 52 mM)/14 mM basic additive.
[b]Volume percentage.

Example 32

Effect of Column Temperature on the Liquid Chromatographic Separation of Enantiomers Using a Column Bonded with a CSP Including a Functionalized CF

Figure 9A:
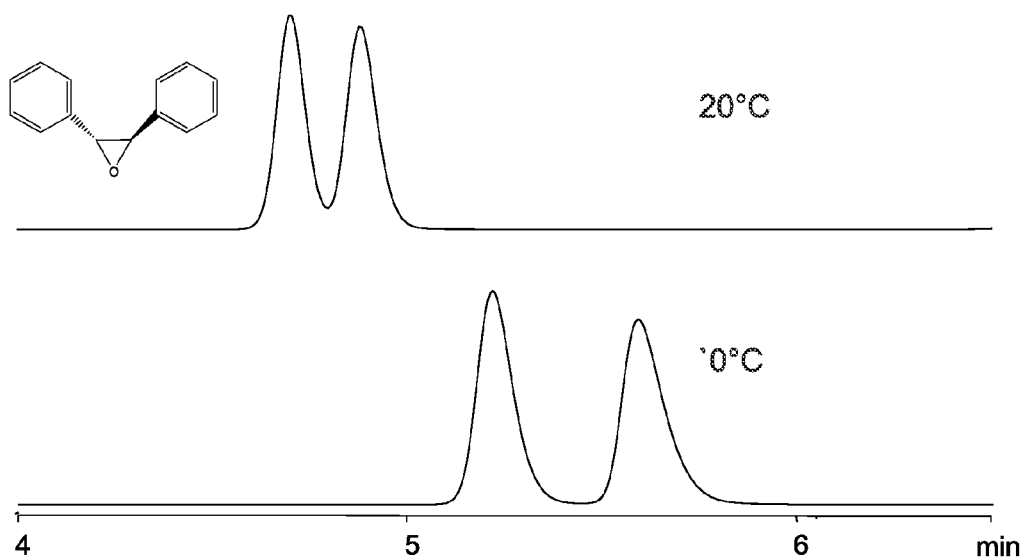
FIG. 9A is a series of liquid chromatograms showing the results of using a column bonded with a CSP including a functionalized cyclofructan of the present invention to separate chiral analytes.
Figure 9B:
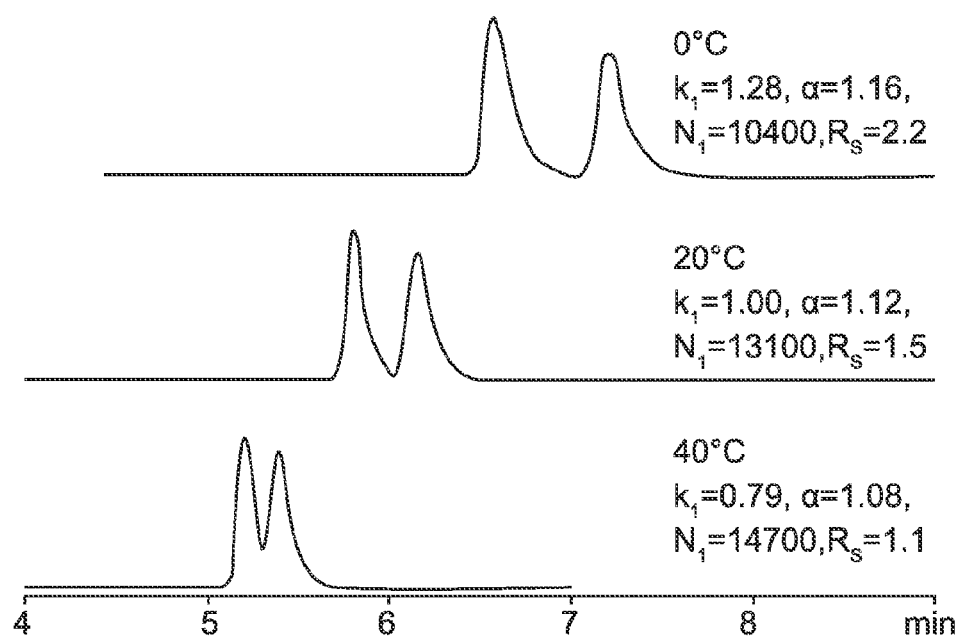
FIG. 9B is a series of liquid chromatograms showing the results of using a column bonded with a CSP including a functionalized cyclofructan of the present invention to separate enantiomers of tyrosinol hydrochloride.

This Example shows that at lower temperatures, in some embodiments of the present invention, enantioselectivity usually increased, at the expense of efficiency. FIGS. 9A and 9B illustrate that reducing the column temperature significantly improved enantioselectivity and resolution when a CSP including a functionalized CF was used to resolve enantiomeric epoxides and tyrosinol hydrochloride. This Example thus shows that enantiomeric separations can be improved by lowering the column temperature.

The analyte in FIG. 9A was trans-stilbene oxide. The derivatized CF was IP—$CF_6$. The mobile phase was 100% heptane. The chromatographic data were as follows: top curve: $k_1$=0.62, α=1.10, $R^s$=1.3; bottom curve: $k_1$=0.80, α=1.16, $R^s$=2.0. The analyte in FIG. 9B was tyrosinol hydrochloride. The derivatized CF was IP—CF6. The mobile phase was 70% methanol/30% acetonitrile/0.3% acetic acid/0.2% triethylamine. The chromatographic data were as follows: top curve: $k_1$=1.28, α=1.16, $R^s$=2.2; middle curve: $k_1$=1.00, α=1.12, $R^s$=1.5; bottom curve: $k_1$=0.79, α=1.08, $R^s$=1.1.

Example 33

Effect of Acetonitrile Concentration on the Liquid Chromatographic Separation of Enantiomers Using a Column Bonded with a CSP Including a Functionalized CF

Figure 10:
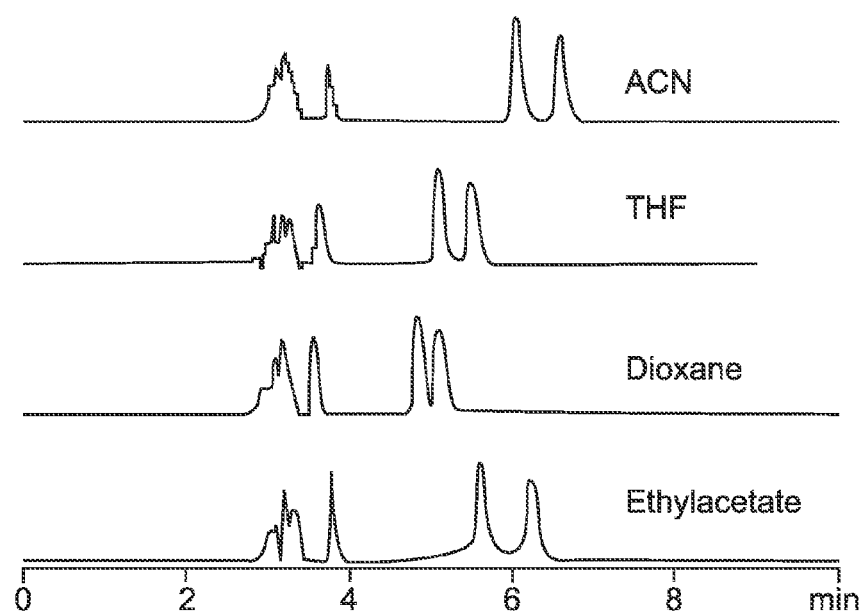
FIG. 10 is a series of liquid chromatograms showing the results of using a column bonded with a CSP including a functionalized cyclofructan of the present invention to separate enantiomers of 1-(2-naphthyl)ethylamine.

This Example shows that, in some embodiments of the present invention, acetonitrile can be used as a preferred component of the mobile phase in the liquid chromatographic separation of enantiomeric primary amines using a column bonded with a CSP including a functionalized CF. Acetonitrile, THF, dioxane, and ethyl acetate were tested as organic modifiers to the mobile phase. Chromatograms of 1-(2-naphthyl)ethylamine separated on an IP—CF6 stationary phase using 70% methanol/30% modifier/0.3% acetic acid/0.2% triethylamine are shown in FIG. 10. Among these four modifiers, the worst enantioselectivity and resolution were observed using dioxane, while the lowest efficiency and asymmetric peaks were obtained with ethyl acetate as the modifier. Generally, the use of acetonitrile as a modifier produced the best results.

Table 4 shows retention factors, selectivities, efficiencies, and resolutions with varying ACN concentration, with the acidic/basic additive concentrations held constant. Increasing the concentration of acetonitrile increased the retention considerably while decreasing selectivity slightly. The highest efficiency was observed with 20-40% acetonitrile. It was also noted that the peaks showed slight fronting when the percentage of acetonitrile was over 50%. The best resolution was obtained when using 50-60% acetonitrile, resulting from longer retention. This Example thus shows that enantiomeric separations can be improved by optimizing the amount of ACN used in the mobile phase, in some embodiments of the present invention.

TABLE 4

Effect of ACN percentage on enantiomeric separation of 1-(2-naphthyl)ethylamine in polar organic mode[b] by a CSP including IP-functionalized-CF6.

| ACN percentage (%) | $k_1$ | α | $n_1'$ | Rs |
|---|---|---|---|---|
| 0 | 0.40 | 1.22 | 13700 | 1.8 |
| 10 | 0.55 | 1.20 | 14600 | 2.0 |
| 20 | 0.76 | 1.18 | 15000 | 2.3 |
| 30 | 1.08 | 1.17 | 15300 | 2.6 |
| 40 | 1.52 | 1.17 | 15200 | 2.9 |
| 50 | 2.25 | 1.17 | 14300[a] | 3.2 |
| 60 | 3.46 | 1.17 | 12400[a] | 3.2 |
| 70 | 5.78 | 1.16 | 7600[a] | 2.9 |
| 80 | 10.99 | 1.14 | 2300[a] | 1.7 |
| 90 | 21.46 | 1.12 | 400[a] | 0.8 |
| 100 | No elution | | | |

[a]Peaks show fronting.
[b]The mobile phase is composed of acetonitrile/methanol/0.3% acetic acid/0.2% triethylamine.

Example 34

Liquid Chromatographic Separation of Chemical Species Using a Column Bonded with a CSP Including Dimethylphenyl-Carbamate-Functionalized-CF7

Figure 11:
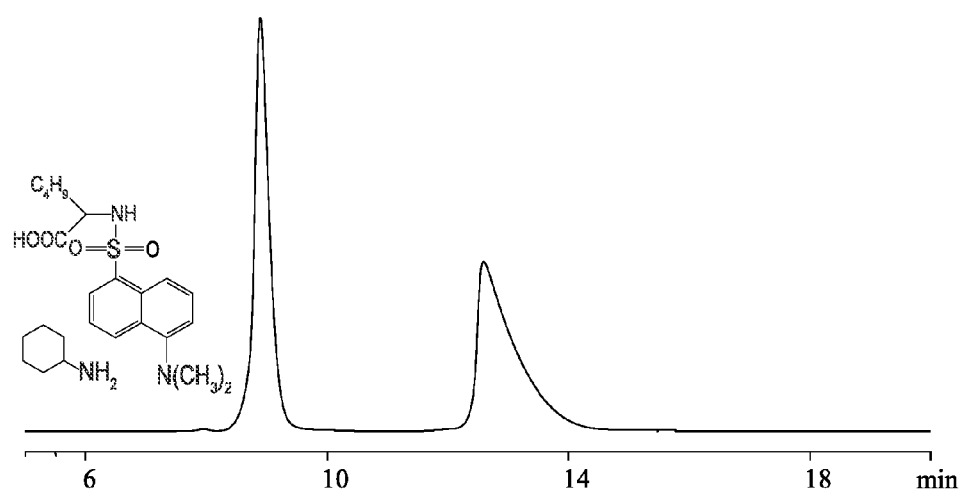
FIG. 11 is a liquid chromatogram showing the results of using a column bonded with a CSP including a functionalized cyclofructan of the present invention to separate chiral analytes.

This Example shows the utility of CF7-based derivatized CFs for use as chiral selectors. As shown in FIG. 11, a derivatized-CF7 CSP successfully separated enantiomers of dansyl-norleucine cyclohexylammonium salt. This analyte was only partially separated by all derivatized-CF6 columns tested. The mobile phase was 80% heptane/20% EtOH/0.1% TFA.

Example 35

High Loading Chromatography Using a CSP Including a Derivatized CF

Figure 12:
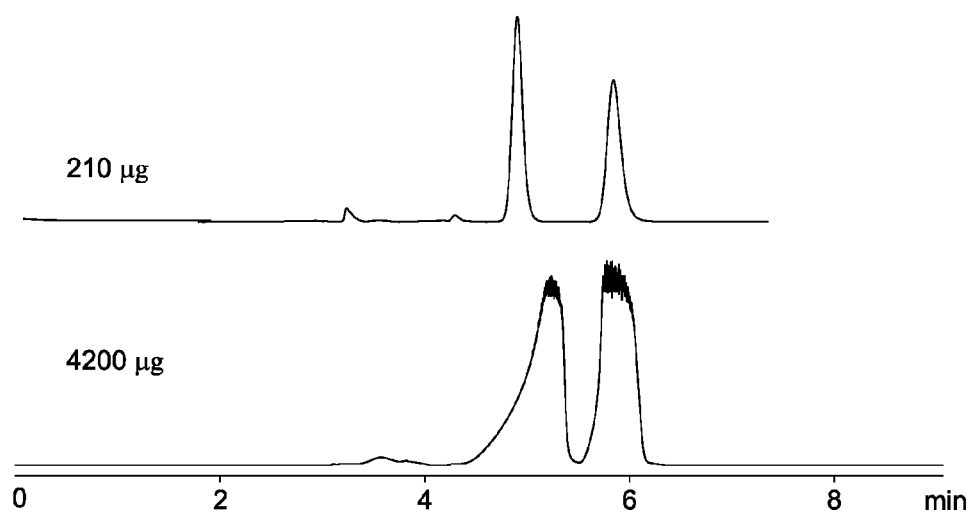
FIG. 12 is a series of liquid chromatograms showing the results of using a column bonded with a CSP including a functionalized cyclofructan of the present invention to preparatively separate enantiomers of N-(3,5-dinitrobenzoyl)-phenylglycine.

This Example shows that CSPs including derivatized CFs can be used as stationary phases for preparative-scale liquid chromatography, including HPLC. A loading test was performed by injecting N-(3,5-dinitrobenzoyl)-phenylglycine on a CSP including RN—CF6 in polar organic mode. As shown in FIG. 12, 4200 µg of the racemic analyte was baseline separated on an analytical column. It should be noted that the injection amount was limited by the solubility of the analyte in the mobile phase. The mobile phase was 85% ACN/15% MeOH/0.3% AA/0.2% TEA. Injection volumes were 5 µL (top curve) and 100 µL (bottom curve). UV detection was at 350 nm. It is clear from this Example that even higher amounts of analyte can be loaded on columns containing CSPs of the present invention while maintaining baseline resolution.

In addition to the foregoing, numerous other chromatographic separations using a column bonded with a CSP including a derivatized cyclofructan residue were carried out. Tables 5-9 list some additional examples of chromatographic separations using a column bonded with a CSP of the present invention. All examples of chromatographic separations using columns bonded with CSPs of the present invention were carried out using the following experimental conditions and procedures.

The high performance liquid chromatography (HPLC) column packing system was composed of an air driven fluid pump (HASKEL, DSTV-122), an air compressor, a pressure regulator, a low pressure gauge, two high-pressure gauges (10,000 and 6,000 psi), a slurry chamber, check valves, and tubings. The CSPs were slurry packed into a 25 cm×0.46 cm (inner diameter, I.D.) stainless steel column.

The HPLC system was an Agilent 1100 system (Agilent Technologies, Palo Alto, Calif.), which consisted of a diode array detector, an autosampler, a binary pump, a temperature-controlled column chamber, and Chemstation software. All chiral analytes were dissolved in ethanol, methanol, or other appropriate mobile phases, as indicated. For the LC analysis, the injection volume and flow rate were 5 µL and 1 mL/min, respectively. Separations were carried out at room temperature (~20° C.) if not specified otherwise. The wavelengths of UV detection were 195, 200, 210, and 254 nm. The mobile phase was degassed by ultrasonication under vacuum for 5 min. Each sample was analyzed in duplicate. Three operation modes (the normal phase mode, polar organic mode, and reversed phase mode) were tested, unless indicated otherwise. In the normal phase mode, heptane with ethanol or isopropanol was used as the mobile phase. In some cases, trifluoroacetic acid (TFA) was used as an additive, as indicated. The mobile phase of the polar organic mode was composed of acetonitrile/methanol and small amounts of acetic acid and triethylamine. Water/acetonitrile or acetonitrile/acetate buffer (20 mM, pH=4.1) was used as the mobile phase in the reversed-phase mode.

Two different supercritical fluid chromatographic instruments were used. One was a Berger SFC unit with an FCM1200 flow control module, a TCM 2100 thermal column module, a dual pump control module, and a column selection valve. The flow rate was 4 mL/min. The cosolvent was composed of methanol/ethanol/isopropanol=1:1:1 and 0.2% diethylamine (DEA). The gradient mobile phase composition was 5% cosolvent hold during 0-0.6 min, 5-60% during 0.6-4.3 min, 60% hold during 4.3-6.3 min, 60%-5% during 6.3-6.9 min, and 5% hold during 6.9-8.0 min. The other SFC system was a Jasco (MD, USA) system comprised of an autosampler unit (AS-2059-SF Plus), a dual pump module (PU-2086 Plus), a column thermostat module (CO-2060 Plus), a UV/Vis detector (UV-2075 Plus), and a back pressure regulator module (SCH-Vch-BP). Unless otherwise specified, the mobile phase was composed of $CO_2$/methanol (0.1% TFA or 0.1% diethylamine). The flow rate was 3 mL/min.

For the calculations of chromatographic data, the "dead time" $t_0$ was determined by the peak of the refractive index change due to the sample solvent or determined by injecting 1,3,5-tri-tent-butylbenzene in the normal phase mode.

TABLE 5

Examples of chromatic separations using columns bonded with CSPs of the present invention.

| No. | Compound name | CSP* | $k_1'$ | α | Rs | Mobile phase |
|---|---|---|---|---|---|---|
| Class A: chiral bases | | | | | | |
| A1 | 1-Aminoindan | CF6—RN | 3.21 | 1.17 | 2.1 | 60ACN/40MEOH/0.3AA/0.2TEA |
| | | CF6—DMP | 6.52 | 1.15 | 1.7 | 75ACN/25MEOH/0.3AA/0.2TEA |
| | | CF6—TB | 3.55 | 1.13 | 2.1 | 60ACN/40MEOH/0.3AA/0.2TEA |
| A2 | 1,2,3,4-Tetrahydro-1-naphthylamine | CF6—RN | 2.03 | 1.18 | 1.9 | 60ACN/40MEOH/0.3AA/0.2TEA |
| | | CF6—DMP | 4.26 | 1.18 | 1.6 | 75ACN/25MEOH/0.3AA/0.2TEA |
| | | CF6—TB | 2.31 | 1.12 | 1.6 | 60ACN/40MEOH/0.3AA/0.2TEA |
| A3 | 1-(2-naphthyl)-ethylamine | CF6—RN | 5.69 | 1.11 | 1.6 | 75ACN/25MEOH/0.3AA/0.2TEA |
| | | CF6—DMP | 4.26 | 1.15 | 1.6 | 75ACN/25MEOH/0.3AA/0.2TEA |
| | | CF6—TB | 2.57 | 1.11 | 1.7 | 60ACN/40MEOH/0.3AA/0.2TEA |
| A4 | 1-(4-Borophenyl)-ethylamine | CF6—RN | 5.11 | 1.15 | 1.5 | 75ACN/25MEOH/0.3AA/0.2TEA |
| | | CF6—DMP | 4.21 | 1.14 | 1.3 | 75ACN/25MEOH/0.3AA/0.2TEA |
| | | CF6—TB | 2.47 | 1.13 | 1.4 | 60ACN/40MEOH/0.3AA/0.2TEA |
| A5 | (±)-1,1-Diphenyl-2-aminopropane | CF6—RN | 3.88 | 1.11 | 1.7 | 85ACN/15MEOH/0.3AA/0.2TEA |
| | | CF6—DMP | 4.41 | 1.11 | 1.3 | 90ACN/10MEOH/0.3AA/0.2TEA |
| A6 | 1,2-Diphenylethylamine | CF6—RN | 2.46 | 1.17 | 1.8 | 75ACN/25MEOH/0.3AA/0.2TEA |
| | | CF6—DMP | 2.17 | 1.14 | 1.5 | 75ACN/25MEOH/0.3AA/0.2TEA |
| | | CF6—TB | 1.39 | 1.18 | 1.7 | 60ACN/40MEOH/0.3AA/0.2TEA |
| A7 | 1-(1-Naphthyl)-ethylamine | CF6—RN | 4.25 | 1.15 | 1.7 | 70ACN/30MEOH/0.3AA/0.2TEA |
| | | CF6—DMP | 4.19 | 1.14 | 1.4 | 75ACN/25MEOH/0.3AA/0.2TEA |
| | | CF6—TB | 2.37 | 1.12 | 1.6 | 60ACN/40MEOH/0.3AA/0.2TEA |

TABLE 5-continued

Examples of chromatic separations using columns bonded with CSPs of the present invention.

| No. | Compound name | CSP* | $k_1'$ | α | Rs | Mobile phase |
|---|---|---|---|---|---|---|
| A8 | DL-Tryptophan benzyl ester | CF6—RN | 0.53 | 1.25 | 2.0 | 75ACN/25MEOH/0.3AA/0.2TEA |
| Class B: chiral acids | | | | | | |
| B1 | 2,3-Dibenzoyl-DL-tartaric acid | CF6—RN | 7.74 | 1.04 | 1.3 | 99.8 ACN/0.2MEOH/0.3AA/0.2TEA |
| B2 | Acetylmandelic acid | CF6—RN | 5.57 | 1.04 | 1.0 | 95heptane/5ETOH/0.1TFA |
| Class C: amino acid derivatives | | | | | | |
| C1 | N-(3,5-dinitrobenzoyl)-DL-leucine | CF6—RN | 1.89 | 1.43 | 5.3 | 70heptane/30ETOH/0.1TFA |
| | | CF6—DMP | 5.54 | 1.12 | 2.3 | 90heptane/10ETOH/0.1TFA |
| C2 | N-benzoyl-valine | CF6—RN | 10.16 | 1.04 | 1.1 | 95heptane/5ETOH/0.1TFA |
| C3 | Carbobenzyloxy-alanine | CF6—DCP | 6.49 | 1.05 | 1.3 | 95heptane/5ETOH/0.1TFA |
| Class D: alcohols | | | | | | |
| D1 | Benzoin | CF6—DMP | 5.91 | 1.07 | 1.5 | 99heptane/1IPA/0.1TFA |
| | | CF6—RN | 9.27 | 1.05 | 1.5 | 99.5heptane/0.5IPA/0.1TFA |
| D2 | 5,5',6,6',7,7',8,8'-Octahydro(1,1'-binaphthalene)-2,2'-diol | CF6—RN | 5.34 | 1.11 | 1.9 | 98heptane/2ETOH/0.1TFA |
| | | CF6—DMP | 5.47 | 1.18 | 2.8 | 99heptane/1IPA/0.1TFA |
| D3 | 1,1'-Bi-2-naphthol | CF6—DCP | 2.31 | 1.27 | 2.5 | 90heptane/10ETOH/0.1TFA |
| | | CF7—DMP | 2.91 | 1.23 | 2.8 | 90heptane/10ETOH/0.1TFA |
| Class E: heterocyclic compounds | | | | | | |
| E1 | Althiazide | CF6—RN | 2.9 | 1.15 | 1.7 | 50heptane/50ETOH |
| E2 | 3-(α-Acetonyl-4-chlorobenzyl)-4-hydroxycoumarin | CF6—DMP | 5.35 | 1.17 | 2.0 | 90heptane/10IPA/0.1TFA |
| | | CF7—DMP | 11.00 | 1.23 | 2.8 | 95heptane/5ETOH/0.1TFA |
| Class F: pharmaceutical compounds | | | | | | |
| F1-anti-inflama-tories | Bendroflumethiazide | CF6—RN | 5.50 | 1.16 | 2.5 | 70heptane/30ETOH/0.1TFA |
| F2-anaesthetics | Tocainide | CF6—RN | 8.15 | 1.10 | 1.6 | 70heptane/30ETOH/0.1TFA |

Table 5 Abbreviations:
$k_1$ = retention factor
α = selectivity
Rs = resolution

DMP
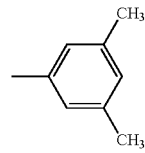

RN
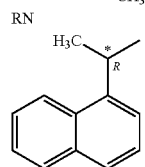

TB
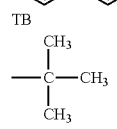

DCP
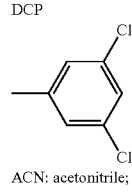

ACN: acetonitrile;
ETOH: ethanol;

TABLE 5-continued

Examples of chromatic separations using columns bonded with CSPs of the present invention.

| No. | Compound name | CSP* | $k_1'$ | α | Rs | Mobile phase |
|---|---|---|---|---|---|---|

IPA: isopropanol;
TFA: trifluoroacetic acid;
AA: acetic acid;
TEA: triethylamine;
CF6: cyclofructan composed of 6 fructofuranose units;
CF7: cyclofructan composed of 7 fructofuranose units

TABLE 6

Examples of chromatic separations of primary amines using columns bonded with CSPs of the present invention.

| # | Compound name | CSP[a] | $k_1$ | α | Rs | Mobile phase[b] |
|---|---|---|---|---|---|---|
| 1 | trans-1-Amino-2-indanol | IP | 2.85 | 1.31 | 3.9 | 60A40M0.3AA0.2T |
| | | ME | 2.44 | 1.28 | 3.5 | 60A40M0.3AA0.2T |
| | | RN-L | 1.43 | 1.23 | 1.6 | 60A40M0.3AA0.2T |
| 2 | cis-1-Amino-2-indanol | IP | 2.69 | 1.12 | 1.6 | 60A40M0.3AA0.2T |
| | | ME | 2.47 | 1.10 | 1.5 | 60A40M0.3AA0.2T |
| | | RN-L | 3.00 | 1.07 | 0.8 | 75A25M0.3AA0.2T |
| 3 | Normetanephrine hydrochloride | IP | 5.83 | 1.16 | 2.6 | 60A40M0.3AA0.2T |
| | | RN-L | 2.84 | 1.15 | 1.6 | 60A40M0.3AA0.2T |
| | | ME | 5.24 | 1.14 | 2.0 | 60A40M0.3AA0.2T |
| 4 | DL-Octopamine hydrochloride | IP | 6.09 | 1.14 | 2.1 | 60A40M0.3AA0.2T |
| | | ME | 5.46 | 1.12 | 1.8 | 60A40M0.3AA0.2T |
| | | RN-L | 2.74 | 1.10 | 1.5 | 60A40M0.3AA0.2T |
| 5 | Phenylpropanolamine hydrochloride | IP | 3.64 | 1.13 | 2.2 | 60A40M0.3AA0.2T |
| | | RN-L | 1.81 | 1.13 | 1.6 | 60A40M0.3AA0.2T |
| | | ME | 3.17 | 1.11 | 1.9 | 60A40M0.3AA0.2T |
| 6 | 1-Aminoindan | IP | 3.90 | 1.17 | 3.1 | 60A40M0.3AA0.3T |
| | | RN-L | 3.21 | 1.17 | 2.1 | 60A40M0.3AA0.2T |
| | | ME | 3.37 | 1.15 | 2.7 | 60A40M0.3AA0.2T |
| 7 | 1,1-Diphenyl-2-aminopropane | IP | 1.12 | 1.09 | 1.5 | 60A40M0.3AA0.2T |
| | | RN-L | 3.31 | 1.07 | 1.5 | 85A15M0.3AA0.2T |
| | | ME | 1.94 | 1.07 | 1.3 | 75A25M0.3AA0.2T |
| 8 | 2-Amino-1-(4-nitrophenyl)-1,3-propanediol | ME | 2.40 | 1.18 | 1.9 | 60A40M0.3AA0.2T |
| | | IP | 2.16 | 1.15 | 2.3 | 60A40M0.3AA0.2T |
| | | RN-L | 6.74 | 1.14 | 1.7 | 85A15M0.3AA0.2T |
| 9 | α-Methylbenzylamine | ME | 3.07 | 1.17 | 1.5 | 60A40M0.3AA0.2T |
| | | IP | 2.77 | 1.15 | 1.5 | 60A40M0.3AA0.2T |
| | | RN-L | 8.12 | 1.09 | 0.8 | 85A15M0.3AA0.2T |
| 10 | DL-Tryptophanol | IP | 3.39 | 1.15 | 2.7 | 60A40M0.3AA0.2T |
| | | ME | 3.03 | 1.12 | 1.7 | 60A40M0.3AA0.2T |
| | | RN-L | 4.66 | 1.12 | 1.4 | 75A25M0.3AA0.2T |
| 11 | 1,2,2-Triphenylethylamine | IP | 1.14 | 1.16 | 1.6 | 75A25M0.3AA0.2T |
| | | ME | 0.48 | 1.07 | 0.6 | 75A25M0.3AA0.2T |

[a]Abbreviations of CSPs: ME = methyl carbamate-CF6 CSP; IP = isopropyl carbamate-CF6 CSP; RN-L = R-naphthylethyl carbamate-CF6 CSP with a low degree of derivitization.
[b]Abbreviations of mobile phases: A = acetonitrile; M = methanol; AA = acetic acid; T = triethylamine.

TABLE 7

Examples of chromatic separations of various chemical species using columns bonded with CSPs of the present invention.

| # | Compound name | CSP[a] | $k_1$ | α | Rs | Mobile phase[b] |
|---|---|---|---|---|---|---|
| | Acids | | | | | |
| 1 | O-Acetylmandelic acid | IP | 11.00 | 1.04 | 1.2 | 98H2E0.1TFA |
| | | SMP | 9.86 | 1.04 | 0.9 | 98H2E0.1TFA |
| 2 | 2,3-Dibenzoyl-DL-tartaric acid | IP | 5.93 | 1.08 | 1.0 | 99A1M0.3AA0.2T |
| | | RN | 7.74 | 1.04 | 1.2 | 99.8A0.2M0.3AA0.2T |
| 3 | Ketorolac | IP | 8.30 | 1.03 | 0.9 | 95H5E0.1TFA |
| | | SMP | 4.77 | 1.03 | 0.6 | 90H10E0.1TFA |
| | | RN | 4.65 | 1.03 | 0.6 | 90H10E0.1TFA |
| 4 | Phenethylsulfamic acid | IP | 3.24 | 1.14 | 2.6 | 60A40M0.3AA0.2T |
| | | SMP | 3.18 | 1.13 | 0.8 | 70H30E0.1TFA |
| | | RN | 5.90 | 1.10 | 1.3 | 80A20M0.3AA0.2T |
| | | DMP | 2.03 | 1.10 | 0.6 | 70H30E/0.1TFA |

TABLE 7-continued

Examples of chromatic separations of various chemical species using columns bonded with CSPs of the present invention.

| # | Compound name | CSP[a] | $k_1$ | α | Rs | Mobile phase[b] |
|---|---|---|---|---|---|---|
| 5 | 1-Methyl-6,7-dihydroxy-1,2,3,4-tetrahydroisoquinoline hydrobromide | RN | 8.87 | 1.16 | 1.6 | 70H30E0.1TFA |
|  |  | SMP | 7.19 | 1.14 | 2.2 | 70H30E0.1TFA |
|  |  | IP | 2.74 | 1.11 | 1.8 | 60A40M0.3AA0.2T |
|  |  | DMP | 4.12 | 1.07 | 1.2 | 70H30E0.1TFA |
| Secondary and tertiary amines | | | | | | |
| 1 | Bis-[(R/S)-1-phenylethyl]amine HCl | RN | 4.04 | 1.16 | 2.5 | 90H10E0.1TFA |
|  |  | SMP | 7.07 | 1.13 | 1.5 | 98H2E0.1TFA |
| 2 | Bendroflumethiazide | RN | 5.50 | 1.16 | 2.3 | 70H30E0.1TFA |
|  |  | SMP | 4.27 | 1.03 | 0.5 | 70H30E0.1TFA |
| 3 | Tröger's base | DMP | 0.95 | 1.59 | 5.7 | 70H30E |
|  |  | RN | 0.96 | 1.53 | 4.2 | 70H30E |
|  |  | DCP | 1.25 | 1.28 | 2.0 | 80H20E |
|  |  | SMP | 0.94 | 1.19 | 1.5 | 80H20E |
|  |  | IP | 0.62 | 1.11 | 0.9 | 80H20E |
| 4 | Orphenadrine citrate salt | DCP | 8.28 | 1.51 | 3.0 | 80H20E |
| 5 | Diperodon hydrochloride | DCP | 2.89 | 1.21 | 1.2 | 80H20E |
|  |  | SMP | 10.36 | 1.06 | 0.7 | 70H30E0.1TFA |
| Amino acid derivatives | | | | | | |
| 1 | N-(3,5-dinitrobenzoyl)-DL-leucine | RN | 0.80 | 1.91 | 4.4 | 50H50E0.1TFA |
|  |  | DMP | 5.54 | 1.12 | 2.3 | 90H10E0.1TFA |
|  |  | SMP | 1.85 | 1.11 | 1.5 | 80H20E0.1TFA |
|  |  | DCP | 7.45 | 1.06 | 0.6 | 80H20E0.1TFA |
| 2 | N-(3,5-Dinitrobenzoyl)-DL-phenylglycine | RN | 7.22 | 1.12 | 1.8 | 70H30E0.1TFA |
|  |  | DMP | 11.01 | 1.08 | 1.5 | 90H10E0.1TFA |
|  |  | SMP | 10.80 | 1.05 | 1.1 | 90H10E0.1TFA |
| 3 | Carbobenzyloxy-alanine | SMP | 3.83 | 1.10 | 1.6 | 90H10I0.1TFA |
|  |  | DCP | 6.49 | 1.06 | 1.3 | 95H5E0.1TFA |
| 4 | N-Benzoyl-DL-phenylalanine β-naphthyl ester | SMP | 4.49 | 1.19 | 3.2 | 90H10E0.1TFA |
|  |  | DMP | 4.00 | 1.10 | 1.7 | 90H10I0.1TFA |
|  |  | IP | 6.19 | 1.08 | 1.5 | 95H5E0.1TFA |
|  |  | RN | 10.25 | 1.06 | 0.6 | 95H5E0.1TFA |
|  |  | DCP | 3.63 | 1.05 | 0.7 | 90H10I0.1TFA |
| 5 | 3,5-Dinitrobenzoyl-tryptophan methyl ester | RN | 3.99 | 1.17 | 2.2 | 50H50E0.1TFA |
|  |  | SMP | 2.76 | 1.10 | 1.5 | 70H30E0.1TFA |
|  |  | DMP | 5.19 | 1.09 | 1.5 | 80H20E0.1TFA |
| 6 | N-2,4-Dinitrophenyl-DL-norleucine | DMP | 5.54 | 1.10 | 1.7 | 95H5I0.1TFA |
|  |  | RN | 10.91 | 1.07 | 1.3 | 95H5E0.1TFA |
| 7 | Dansyl-norleucine cyclohexylammonium salt | SMP | 6.95 | 1.07 | 1.4 | 90H10E0.1TFA |
|  |  | DMP | 15.05 | 1.05 | 1.2 | 95H5E0.1TFA |
|  |  | IP | 6.93 | 1.04 | 0.8 | 90H10E0.1TFA |
| Alcohols | | | | | | |
| 1 | α-Methyl-9-anthracenemethanol | RN | 5.05 | 1.08 | 1.7 | 98H2I0.1TFA |
|  |  | DMP | 7.61 | 1.03 | 0.7 | 99H1I0.1TFA |
|  |  | SMP | 5.18 | 1.02 | 0.5 | 98H2E0.1TFA |
| 2 | Benzoin | DMP | 5.91 | 1.07 | 1.5 | 99H1I0.1TFA |
|  |  | SMP | 4.89 | 1.05 | 1.3 | 98H2E0.1TFA |
|  |  | RN | 6.22 | 1.04 | 0.8 | 98H2E0.1TFA |
| 3 | N,N'-Dibenzyl-tartramide | DMP | 18.03 | 1.10 | 1.5 | 95H5I0.1TFA |
|  |  | DCP | 3.34 | 1.10 | 1.2 | 80H20E0.1TFA |
|  |  | RN | 11.30 | 1.06 | 1.3 | 90H10E0.1TFA |
|  |  | SMP | 9.26 | 1.05 | 0.8 | 90H10E0.1TFA |
| 4 | furoin | IP | 9.91 | 1.03 | 1.3 | 95H5E0.1TFA |
|  |  | DMP | 9.98 | 1.03 | 0.6 | 98H2E0.1TFA |
|  |  | SMP | 5.64 | 1.02 | 0.5 | 90H10E/0.1TFA |
| 5 | Cromakalim | DMP | 16.00 | 1.05 | 1.5 | 95H5E0.1TFA |
|  |  | DCP | 8.69 | 1.05 | 1.1 | 90H10E0.1TFA |
|  |  | RN | 8.84 | 1.02 | 0.4 | 90H10E0.1TFA |
| Others | | | | | | |
| 1 | 1,1'-Bi(2-naphthyl diacetate) | IP | 0.40 | 1.35 | 2.9 | 70H30E |
|  |  | DMP | 0.74 | 1.21 | 1.7 | 70H30E |
|  |  | SMP | 0.77 | 1.17 | 1.9 | 70H30E |
|  |  | RN | 1.79 | 1.11 | 1.6 | 90H10E0.1TFA |
|  |  | DCP | 1.15 | 1.08 | 1.1 | 90H10E0.1TFA |
| 2 | 5,5',6,6',7,7',8,8'-Octahydro(1,1'-binaphthalene)-2,2'diol | DMP | 5.47 | 1.18 | 2.8 | 99H1I0.1TFA |
|  |  | RN | 5.34 | 1.11 | 1.9 | 98H2E0.1TFA |
|  |  | SMP | 4.47 | 1.09 | 1.5 | 98H2E0.1TFA |

TABLE 7-continued

Examples of chromatic separations of various chemical species using columns bonded with CSPs of the present invention.

| # | Compound name | CSP[a] | $k_1$ | α | Rs | Mobile phase[b] |
|---|---|---|---|---|---|---|
| 3 | 2,2'-Diamino-1,1'-binaphthalene | DMP | 1.43 | 1.45 | 5.3 | 70H30E |
|   |   | DCP | 1.77 | 1.22 | 2.0 | 80H20E |
|   |   | SMP | 1.91 | 1.20 | 3.1 | 70H30E |
|   |   | RN | 2.31 | 1.18 | 2.8 | 70H30E |
|   |   | IP | 2.15 | 1.16 | 3.0 | 80H20E |
| 4 | 6,6'-Dibromo-1,1'-bi-2-naphthol | DMP | 0.74 | 1.58 | 4.7 | 70H30E |
|   |   | DCP | 2.13 | 1.24 | 5.0 | 90H10E |
|   |   | SMP | 0.93 | 1.19 | 2.1 | 70H30E |
|   |   | RN | 1.17 | 1.15 | 1.5 | 70H30E |
|   |   | IP | 3.63 | 1.07 | 1.5 | 90H10E |
| 5 | Althiazide | RN | 2.83 | 1.16 | 1.9 | 50H50E0.1TFA |
|   |   | DMP | 8.80 | 1.04 | 0.7 | 80H20E0.1TFA |
|   |   | IP | 8.29 | 1.02 | 0.8 | 70H30E0.1TFA |
|   |   | SMP | 7.10 | 1.02 | 0.5 | 70H30E/0.1TFA |
| 6 | 1,1'-Bi-2-naphthol bis(trifluoromethanesulfonate) | SMP | 3.84 | 1.17 | 2.0 | 100H |
|   |   | IP | 1.17 | 1.08 | 1.5 | 100H |
|   |   | RN | 6.13 | 1.08 | 1.3 | 100H |
| 7 | cis-4,5-Diphenyl-2-oxazolidinone | DMP | 5.41 | 1.09 | 1.6 | 90H10I0.1TFA |
|   |   | RN | 6.82 | 1.04 | 0.8 | 90H10I0.1TFA |
| 8 | 2,3-Dihydro-7a-methyl-3-phenylpyrrolo[2,1-b]oxazol-5(7aH)-one | RN | 3.20 | 1.12 | 1.9 | 85H15I0.1TFA |
|   |   | DMP | 5.13 | 1.05 | 1.1 | 98H2E0.1TFA |
|   |   | SMP | 2.46 | 1.03 | 0.7 | 98H2E0.1TFA |
|   |   | DCP | 2.67 | 1.02 | 0.6 | 90H10E0.1TFA |
| 9 | Ethyl 11-cyano-9,10-dihydro-endo-9,10-ethanoanthracene-11-carboxylate | SMP | 1.44 | 1.13 | 2.0 | 90H10I0.1TFA |
|   |   | RN | 3.21 | 1.08 | 1.5 | 98H2E0.1TFA |
|   |   | IP | 1.42 | 1.08 | 1.5 | 95H5E0.1TFA |
|   |   | DMP | 2.07 | 1.03 | 0.5 | 98H2E0.1TFA |
| 10 | Lormetazepam | SMP | 3.87 | 1.08 | 1.5 | 80H20E0.1TFA |
|   |   | IP | 8.46 | 1.06 | 1.5 | 90H10E0.1TFA |
|   |   | RN | 5.02 | 1.04 | 0.7 | 80H20E0.1TFA |
| 11 | 3a,4,5,6-Tetrahydro-succininido[3,4-b]acenaphthen-10-one | SMP | 2.36 | 1.13 | 2.2 | 70H30E0.1TFA |
|   |   | IP | 2.14 | 1.12 | 1.9 | 70H30E0.1TFA |
|   |   | RN | 3.25 | 1.10 | 1.5 | 70H30E0.1TFA |
|   |   | DMP | 7.35 | 1.08 | 1.5 | 90H10E0.1TFA |
| 12 | 3-(alpha-Acetonyl-4-chlorobenzyl)-4-hydroxycoumarin | DMP | 5.35 | 1.17 | 2.0 | 90H10I0.1TFA |
|   |   | SMP | 5.16 | 1.14 | 2.2 | 90H10E0.1TFA |
|   |   | RN | 15.94 | 1.10 | 1.6 | 95H5E0.1TFA |
|   |   | DCP | 4.65 | 1.10 | 1.4 | 90H10E0.1TFA |
|   |   | IP | 4.61 | 1.09 | 1.5 | 90H10E0.1TFA |
| 13 | Warfarin | DMP | 9.87 | 1.10 | 1.6 | 95H5I0.1TFA |
|   |   | SMP | 7.19 | 1.08 | 0.9 | 90H10I0.1TFA |
|   |   | DCP | 4.98 | 1.07 | 0.8 | 90H10E0.1TFA |
|   |   | RN | 11.94 | 1.05 | 1.2 | 95H5E0.1TFA |
|   |   | IP | 4.60 | 1.02 | 0.5 | 90H10E0.1TFA |
| 14 | Fipronil | SMP | 16.03 | 1.09 | 2.0 | 98H2E0.1TFA |
|   |   | IP | 2.83 | 1.08 | 1.5 | 90H10E0.1TFA |
|   |   | RN | 12.02 | 1.07 | 1.5 | 97H3E0.1TFA |
|   |   | DCP | 0.55 | 1.03 | 0.4 | 80H20E |
| 15 | trans-Stilbene oxide | IP | 0.62 | 1.10 | 1.3 | 100H |
|   |   | SMP | 2.02 | 1.09 | 1.5 | 100HEP |
|   |   | RN | 2.75 | 1.07 | 1.0 | 100HEP |
| 16 | Thalidomide | SMP | 5.89 | 1.10 | 1.9 | 70H30E0.1TFA |
|   |   | DMP | 8.03 | 1.08 | 1.5 | 80H20E0.1TFA |
|   |   | DCP | 10.69 | 1.05 | 1.0 | 80H20E |
|   |   | RN | 7.85 | 1.04 | 0.7 | 70H30E0.1TFA |
| 17 | 3,5-Dinitrobenzoyl-2-aminoheptane | RN | 1.68 | 1.15 | 2.2 | 80H20E0.1TFA |
| 18 | 3,5-Dinitro-N-(1-phenylethyl)-benzamide | RN | 1.24 | 1.92 | 8.2 | 50H50E0.1TFA |
|   |   | SMP | 0.93 | 1.14 | 1.5 | 70H30E0.1TFA |

[a]Abbreviations of CSPs: DMP = dimethylphenyl carbamate-CF6 CSP; DCP = dichlorophenyl carbamate-CF6 CSP; RN = R-naphthylethyl carbamate-CF6 CSP; SMP = S-methylbenzyl carbamate-CF6 CSP; IP = isopropyl carbamate-CF6 CSP; ME = methyl carbamate-CF6 CSP.
[b]Abbreviations of mobile phases: H = heptane; I = isopropanol; E = ethanol; A = acetonitrile; M = methanol; AA = acetic acid; T = triethylamine; TFA = trifluoroacetic acid.

TABLE 8

Examples of chromatic separations of racemic primary amine-containing compounds using a column bonded with a CSP including IP—CF6.

| | Compound name | Structure | $k_1$ | α | Rs | Mobile phase[a] |
|---|---|---|---|---|---|---|
| Group A: Amino alcohols | | | | | | |
| 1 | (±)-α-(1-Aminoethyl)-4-hydroxybenzyl alcohol hydrochloride | 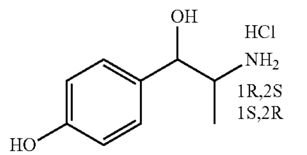 | 1.95 | 1.09 | 1.6 | 50A50M0.3AA0.2T |
| 2 | Normetanephrine hydrochloride | 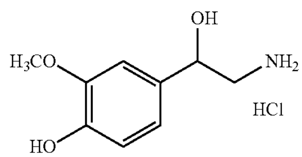 [SMILES: COc1cc(C(O)CN)ccc1O ; Cl] | 1.27 | 1.17 | 2.2 | 30A70M0.3AA0.2T |
| 3 | Norepinephrine L-bitartrate hydrate | 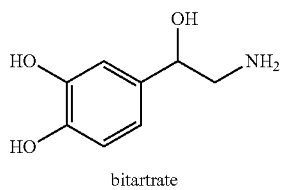 [SMILES: NCC(O)c1ccc(O)c(O)c1] | 7.28 | 1.13 | 1.9 | 60A40M0.3AA0.2T |
| 4 | Octopamine hydrochloride | 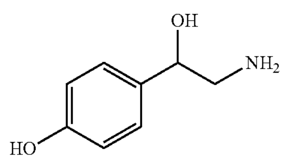 [SMILES: NCC(O)c1ccc(O)cc1] | 1.24 | 1.15 | 1.9 | 30A70M0.3AA0.2T |
| 5 | Phenylpropanolamine hydrochloride | 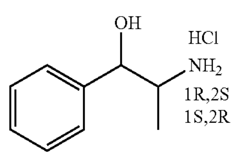 | 1.44 | 1.10 | 1.7 | 40A60M0.3AA0.2T |
| 6 | 2-Phenylglycinol | 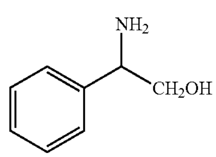 | 1.49 | 1.08 | 1.5 | 50A50M0.3AA0.2T |
| 7 | 2-Amino-3-phenyl-1-propanol | 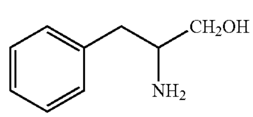 [SMILES: NC(CO)Cc1ccccc1] | 0.86 | 1.15 | 1.8 | 30A70M0.3AA0.2T |
| 8 | 4-Chlorophenyl alaninol | 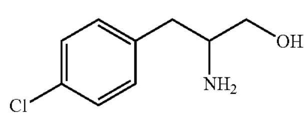 [SMILES: NC(CO)Cc1ccc(Cl)cc1] | 0.90 | 1.14 | 1.7 | 30A70M0.3AA0.2T |
| 9 | trans-1-Amino-2-indanol | 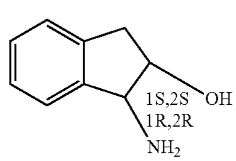 [SMILES: NC1c2ccccc2CC1O] | 0.92 | 1.29 | 3.5 | 30A70M0.3AA0.2T |

TABLE 8-continued

*Examples of chromatic separations of racemic primary amine-containing compounds using a column bonded with a CSP including IP—CF6.*

| | Compound name | Structure | $k_1$ | α | Rs | Mobile phase[a] |
|---|---|---|---|---|---|---|
| 10 | cis-1-Amino-2-indanol | 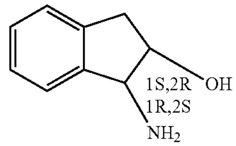 | 1.14 | 1.13 | 1.7 | 40A60M0.3AA0.2T |
| 11 | 2-Amino-1-phenylethanol | 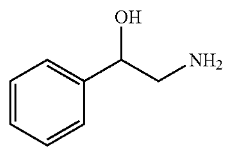 | 1.26 | 1.17 | 1.8 | 30A70M0.3AA0.2T |
| 12 | 2-Amino-1,2-diphenylethanol | 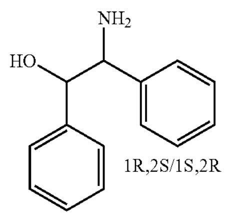 [SMILES: NC(c1ccccc1)C(O)c1ccccc1] | 0.49 | 1.27 | 2.5 | 30A70M0.3AA0.2T |
| 13 | 2-Amino-1-phenyl-1,3-propanediol | 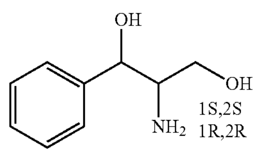 [SMILES: NC(CO)C(O)c1ccccc1] | 3.41 | 1.10 | 1.8 | 60A40M0.3AA0.2T0C. |
| 14 | 2-Amino-1-(4-nitrophenyl)-1,3-propanediol | 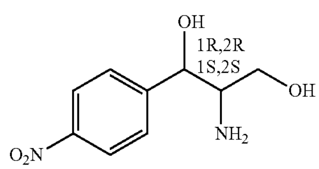 [SMILES: NC(CO)C(O)c1ccc([N+](=O)[O-])cc1] | 1.20 | 1.14 | 1.9 | 50A50M0.3AA0.2T |
| 15 | Tyrosinol hydrochloride | 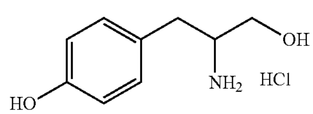 [SMILES: NC(CO)Cc1ccc(O)cc1 ; Cl] | 1.00 | 1.12 | 1.5 | 30A70M0.3AA0.2T |
| 16 | Tryptophanol | 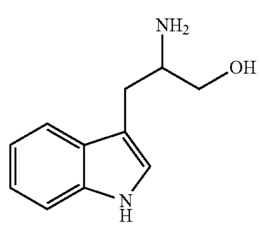 [SMILES: NC(CO)Cc1c[nH]c2ccccc12] | 0.80 | 1.16 | 1.9 | 30A70M0.3AA0.2T |
| 17 | Norphenylephrine hydrochloride | 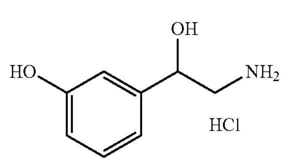 [SMILES: NCC(O)c1cccc(O)c1 ; Cl] | 1.22 | 1.15 | 1.8 | 30A70M0.3AA0.2T |
| 18 | Histidinol dihydrochloride | 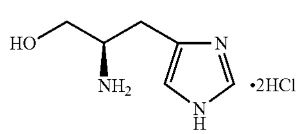 | 20.59 | 1.12 | 1.5 | 60A40M0.3AA0.2T0C. |

TABLE 8-continued

Examples of chromatic separations of racemic primary amine-containing compounds using a column bonded with a CSP including IP—CF6.

| | Compound name | Structure | $k_1$ | α | Rs | Mobile phase[a] |
|---|---|---|---|---|---|---|
| 19 | (R,R/S,S) 2-Amino-1,2-diphenylethanol | 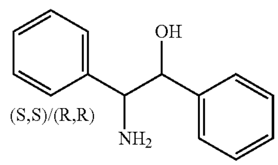 [SMILES: NC(c1ccccc1)C(O)c1ccccc1] | 2.34 | 1.06 | 1.0 | 60A40M0.3AA0.2T0C. |
| 20 | 3-Amino-2-methyl-3-phenyl-butan-2-ol | 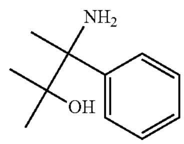 | 1.42 | 1.13 | 2.1 | 60A40M0.3AA0.2T |
| 21 | 2-Amino-1-pentanol | 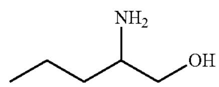 | 4.32 | 1.09 | 1.5 | 70A30M1.2AA0.8T[b] |
| 22 | 2-Amino-1-hexanol | 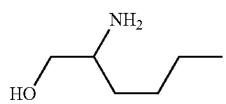 | 6.08 | 1.09 | 1.5 | 70A30M0.3AA0.2T[c] |
| 23 | 3-Amino-1,2-propanediol | 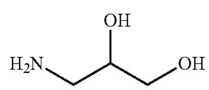 | 1.57 | 1.06 | 0.8 | 30A70M0.3AA0.2T[c] |
| 24 | 2-Amino-1-propanol | 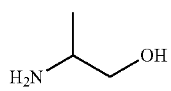 | 3.91 | 1.11 | 1.5 | 60A40M0.3AA0.2T[c] |
| 25 | 2-Amino-1-butanol | 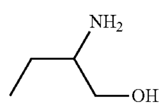 | 2.63 | 1.05 | 0.6 | 60A40M0.3AA0.2T[c] |
| 26 | Trans-2-amino-cyclohexanol | 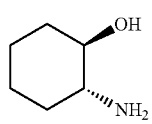 | 6.58 | 1.11 | 1.5 | 80A20M1.2AA0.8T[b] |
| 27 | Cis-2-amino-cyclohexanol | 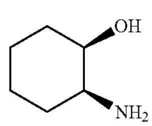 | 6.03 | 1.03 | 0.5 | 80A20M1.2AA0.8T[c] |

Group B: Amino acid esters

| | | | | | | |
|---|---|---|---|---|---|---|
| 1 | Phenylalanine methyl ester hydrochloride | | 9.93 | 1.13 | 2.4 | 70H30E0.1TFA |
| 2 | 2-Phenylglycine methyl ester hydrochloride | | 13.66 | 1.06 | 1.0 | 70H30E0.1TFA |

TABLE 8-continued

Examples of chromatic separations of racemic primary amine-containing compounds using a column bonded with a CSP including IP—CF6.

| | Compound name | Structure | $k_1$ | α | Rs | Mobile phase[a] |
|---|---|---|---|---|---|---|
| 3 | Tryptophan methyl ester hydrochloride | 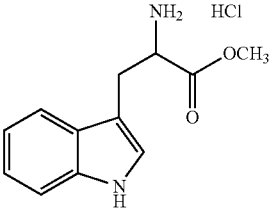 [SMILES: Cl ; COC(=O)C(N)Cc1c[nH]c2ccccc12] | 3.05 | 1.23 | 1.5 | 60H30E0.1TFA |
| 4 | Tryptophan benzyl ester | 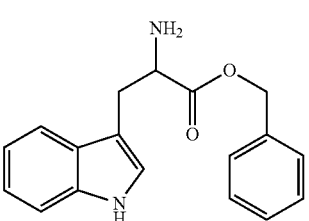 | 9.47 | 1.17 | 2.6 | 70H30E0.1TFA |
| 5 | Alaproclate hydrochloride | 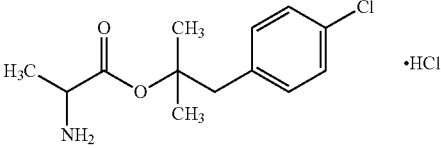 [SMILES: CC(N)C(=O)OC(C)(C)Cc1ccc(Cl)cc1 ; Cl] | 8.43 | 1.10 | 1.5 | 70H30E0.1TFA |
| 6 | 4-Chloro-DL-phenylalanine methyl ester hydrochloride | 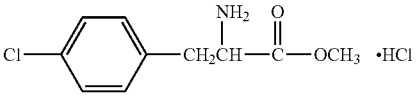 | 10.46 | 1.08 | 1.5 | 70H30E0.1TFA |
| 7 | Tryptophan butyl ester hydrochloride | 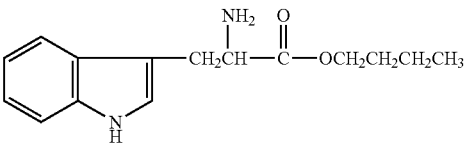 | 7.39 | 1.16 | 1.6 | 70H30E0.1TFA |
| 8 | Amlodipine | 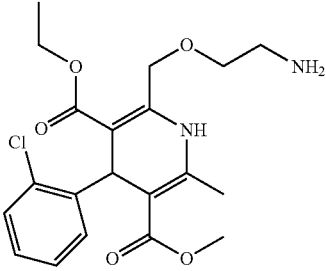 [SMILES: CCOC(=O)C1=C(COCCN)NC(C)=C(C(=O)OC)C1c1ccccc1Cl] | 5.22 | 1.11 | 1.8 | 60A40M0.3AA0.2T0C. |
| 9 | Phenylalanine benzyl ester hydrochloride | 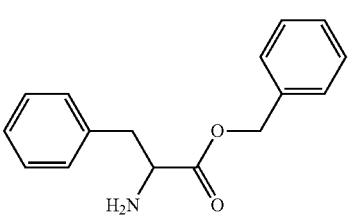 [SMILES: NC(Cc1ccccc1)C(=O)OCc1ccccc1] | 8.88 | 1.06 | 0.8 | 70H30E0.1TFA |
| 10 | Tyrosine tert-butyl ester | 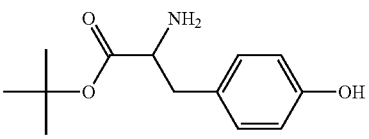 [SMILES: CC(C)(C)OC(=O)C(N)Cc1ccc(O)cc1] | 18.37 | 1.14 | 1.7 | 80H20E0.1TFA |

TABLE 8-continued

Examples of chromatic separations of racemic primary amine-containing compounds using a column bonded with a CSP including IP—CF6.

| | Compound name | Structure | $k_1$ | α | Rs | Mobile phase[a] |
|---|---|---|---|---|---|---|
| 11 | Tyrosine benzylester | 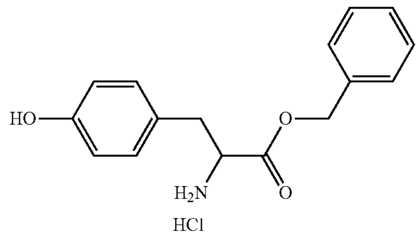 [SMILES: NC(Cc1ccc(O)cc1)C(=O)OCc1ccccc1 ; Cl] | 11.49 | 1.13 | 0.9 | 70H30E0.1TFA |
| 12 | Phenylalanine tert-butyl ester hydrochloride | 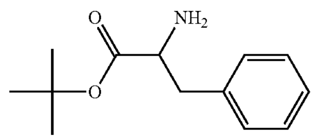 [SMILES: CC(C)(C)OC(=O)C(N)Cc1ccccc1] | 0.61 | 1.04 | 0.4 | 95A5M0.3AA0.2T |
| 13 | tert-Butyl-tyrosine allyl ester hydrochloride | 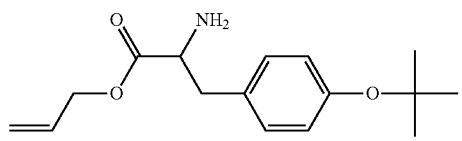 [SMILES: C=CCOC(=O)C(N)Cc1ccc(OC(C)(C)C)cc1] | 15.40 | 1.09 | 1.5 | 80H20E0.1TFA |
| 14 | Tyrosine methyl ester hydrochloride | 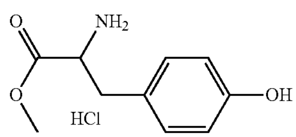 | 14.41 | 1.13 | 1.1 | 70H30E0.1TFA |
| 15 | Methyl 3-phenyl-3-amino-propionate hydrochloride | 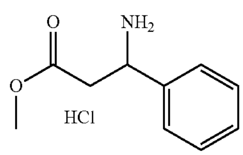 | 1.14 | 1.12 | 1.7 | 60A40M0.3AA0.2T |
| 16 | Phenylglycine tert-butyl ester hydrochloride | 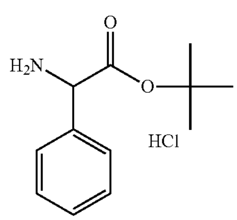 | 13.98 | 1.04 | 0.7 | 80H20E0.1TFA |
| 17 | DL-Leucine benzyl ester | 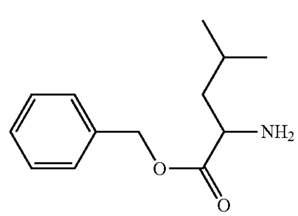 [SMILES: CC(C)CC(N)C(=O)OCc1ccccc1] | 26.59 | 1.12 | 1.8 | 80H20E0.1TFA0C. |
| 18 | Alanine methyl ester hydrochloride | 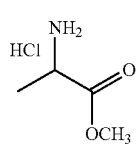 | 2.70 | 1.04 | 0.7 | 60A40M0.3AA0.2T[b] |

TABLE 8-continued

Examples of chromatic separations of racemic primary amine-containing compounds using a column bonded with a CSP including IP—CF6.

| | Compound name | Structure | $k_1$ | α | Rs | Mobile phase[a] |
|---|---|---|---|---|---|---|
| Group C: Amino amides | | | | | | |
| 1 | DL-Methionine β-Naphthylamide | 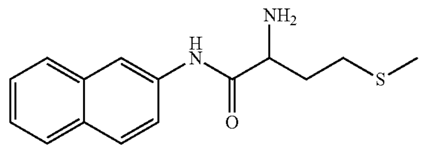 [SMILES: CSCCC(N)C(=O)Nc1ccc2ccccc2c1] | 9.40 | 1.23 | 3.4 | 70H30E0.1TFA |
| 2 | Midodrine hydrochloride | 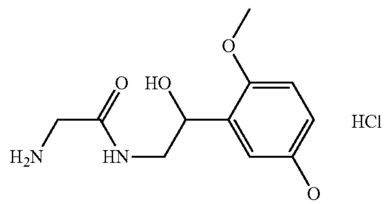 [SMILES: COc1ccc(O)cc1C(O)CNC(=O)CN ; Cl] | 5.32 | 1.03 | 0.7 | 60A40M0.3AA0.2T |
| 3 | Alanine-β-naphthylamide hydrochloride | 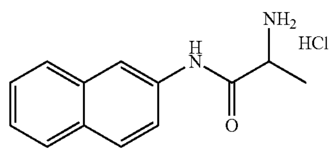 [SMILES: CC(N)C(=O)Nc1ccc2ccccc2c1 ; Cl] | 4.09 | 1.02 | 0.6 | 75A25M0.3AA0.2T |
| 4 | Tryptophanamide hydrochloride | 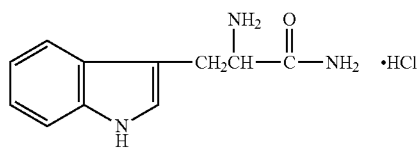 | 8.27 | 1.12 | 2.1 | 75A25M0.3AA0.2TOC. |
| 5 | Tocainide | 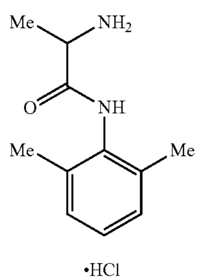 [SMILES: Cc1cccc(C)c1NC(=O)C(C)N ; Cl] | 4.07 | 1.08 | 1.7 | 75A25M0.3AA0.2T |
| 6 | Phenylglycinamide hydrochloride | 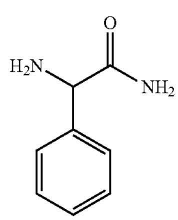 [SMILES: NC(=O)C(N)c1ccccc1] | 3.86 | 1.02 | 0.5 | 75A25M0.3AA0.2T |
| 7 | Phenylalanine hydroxamate | 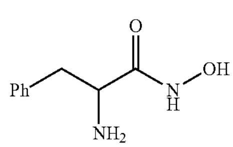 [SMILES: NC(Cc1ccccc1)C(=O)NO] | 6.67 | 1.15 | 0.8 | 60H40E0.1TFA |
| 8 | 3-Aminohexahydro-2-Azepinone | 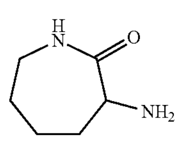 | 2.01 | 1.48 | 2.5 | 50A50M0.3AA0.2T[c] |

TABLE 8-continued

Examples of chromatic separations of racemic primary amine-containing compounds using a column bonded with a CSP including IP—CF6.

| | Compound name | Structure | $k_1$ | α | Rs | Mobile phase[a] |
|---|---|---|---|---|---|---|
| Group D: Amino acids | | | | | | |
| 1 | 3-Amino-3-phenylpropionic acid | 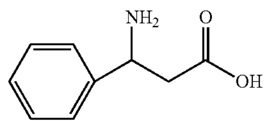 [SMILES: NC(CC(=O)O)c1ccccc1] | 6.41 | 1.08 | 1.1 | 60A40M0.3AA0.2T0C. |
| 2 | 4-Nitro-DL-phenylalanine | 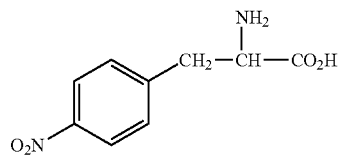 [SMILES: NC(Cc1ccc([N+](=O)[O-])cc1)C(=O)O] | 15.35 | 1.14 | 1.5 | 75A25M0.3AA0.2T0C.[f] |
| 3 | p-Fluorophenylalanine | 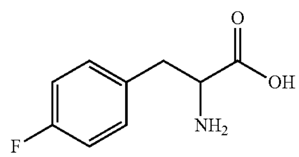 [SMILES: NC(Cc1ccc(F)cc1)C(=O)O] | 11.17 | 1.15 | 1.5 | 75A25M0.3AA0.2T0C. |
| 4 | Kynurenine | 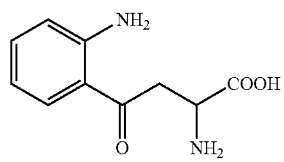 [SMILES: Nc1ccccc1C(=O)CC(N)C(=O)O] | 9.80 | 1.03 | 0.7 | 75A25M0.3AA0.2T |
| 5 | 5-Methyl-tryptophan | 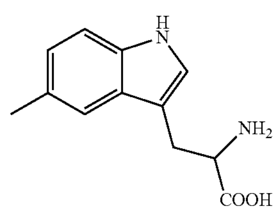 [SMILES: Cc1ccc2[nH]cc(CC(N)C(=O)O)c2c1] | 9.17 | 1.14 | 1.5 | 75A25M0.3AA0.2T0C. |
| 6 | 6-Methyl-tryptophan | 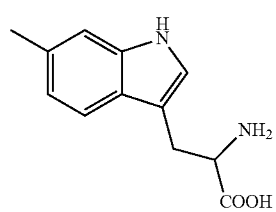 [SMILES: Cc1ccc2c(CC(N)C(=O)O)c[nH]c2c1] | 9.87 | 1.18 | 1.5 | 75A25M0.3AA0.2T0C. |
| 7 | α-Amino-2-thienylacetic acid | 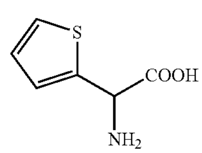 | 10.28 | 1.04 | 0.7 | 75A25M0.3AA0.2T |
| 8 | 3,4-Dihydroxy-phenylalanine | 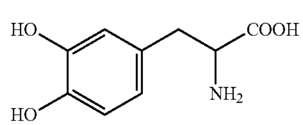 [SMILES: NC(Cc1ccc(O)c(O)c1)C(=O)O] | 2.89 | 1.11 | 1.5 | 60A40M0.3AA0.2T0C. |
| 9 | Baclofen | 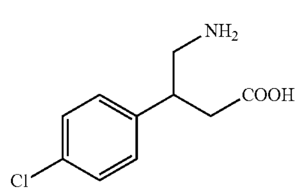 [SMILES: NCC(CC(=O)O)c1ccc(Cl)cc1] | 22.59 | 1.04 | 0.7 | 75A25M0.3AA0.2T |

TABLE 8-continued

Examples of chromatic separations of racemic primary amine-containing compounds using a column bonded with a CSP including IP—CF6.

| | Compound name | Structure | $k_1$ | α | Rs | Mobile phase[a] |
|---|---|---|---|---|---|---|
| 10 | Thyroxine | 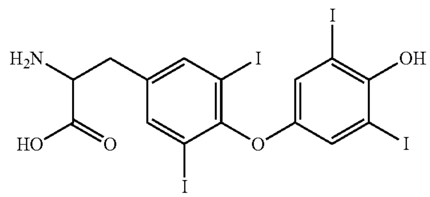 [SMILES: NC(Cc1cc(I)c(Oc2cc(I)c(O)c(I)c2)c(I)c1)C(=O)O] | 8.56 | 1.02 | 0.8 | 75A25M0.3AA0.2T |
| 11 | Phenylalanine | 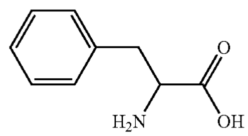 [SMILES: NC(Cc1ccccc1)C(=O)O] | 11.94 | 1.13 | 1.5 | 75A25M0.3AA0.2T0C. |
| 12 | 3-(1-Naphthyl)alanine | 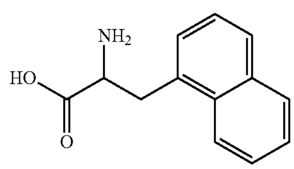 [SMILES: NC(Cc1cccc2ccccc12)C(=O)O] | 9.83 | 1.19 | 1.8 | 75A25M0.3AA0.2T0C. |
| 13 | 2-Amino-2-phenylbutyric acid | 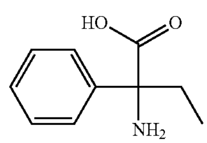 | 1.87 | 1.15 | 1.8 | 60A40M0.3AA0.5T |
| 14 | Arginine | 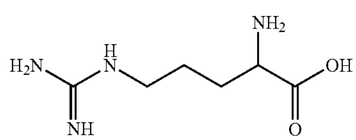 [SMILES: N=C(N)NCCCC(N)C(=O)O] | 4.86 | 1.15 | 0.7 | 50H50E0.1TFA |

Group E: Others

| | | | | | | |
|---|---|---|---|---|---|---|
| 1 | 1-Aminoindan | | 1.03 | 1.16 | 2.3 | 30A70M0.3AA0.2T |
| 2 | p-Chloroamphetamine HCl | | 5.54 | 1.02 | 0.7 | 60A40M0.3AA0.2T |
| 3 | trans-2-Phenylcyclopropyl-amine | | 8.15 | 1.06 | 1.5 | 60A40M0.3AA0.2T0C. |
| 4 | 1,2,3,4-Tetrahydro-1-naphthylamine | | 0.72 | 1.17 | 1.6 | 30A70M0.3AA0.2T |

TABLE 8-continued

Examples of chromatic separations of racemic primary amine-containing compounds using a column bonded with a CSP including IP—CF6.

| | Compound name | Structure | $k_1$ | α | Rs | Mobile phase[a] |
|---|---|---|---|---|---|---|
| 5 | 1-(1-Naphthyl)ethylamine | 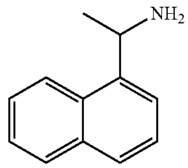 | 0.86 | 1.24 | 2.9 | 30A70M0.3AA0.2T |
| 6 | 1-(2-naphthyl)ethylamine | 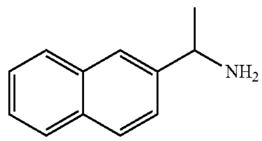 | 0.90 | 1.18 | 2.5 | 30A70M0.3AA0.2T |
| 7 | 1-(4-Borophenyl)-ethylamine | 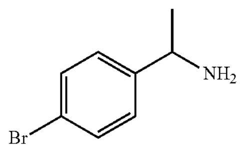 | 1.03 | 1.18 | 2.4 | 30A70M0.3AA0.2T |
| 8 | 2-Amino-3-methyl-1,1-diphenylbutane | 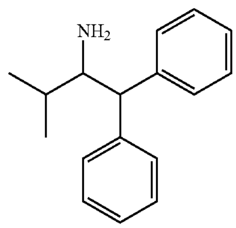 [SMILES: CC(C)C(N)C(c1ccccc1)c1ccccc1] | 10.98 | 1.10 | 1.7 | 90H10E0.1TFA0C. |
| 9 | 2-Amino-4-methyl-1,1-diphenylpentane | 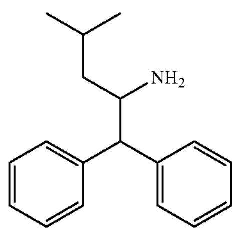 [SMILES: CC(C)CC(N)C(c1ccccc1)c1ccccc1] | 8.43 | 1.08 | 1.5 | 90H10E0.1TFA0C. |
| 10 | 1-Benzyl-2,2-diphenylethylamine | 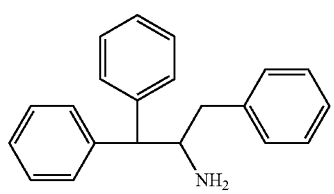 [SMILES: NC(Cc1ccccc1)C(c1ccccc1)c1ccccc1] | 3.25 | 1.09 | 1.5 | 80H20E0.1TFA |
| 11 | 1,1-Diphenyl-2-aminopropane | 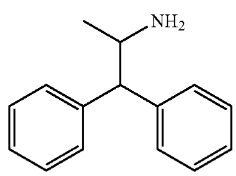 [SMILES: CC(N)C(c1ccccc1)c1ccccc1] | 1.39 | 1.10 | 1.8 | 60A40M0.3AA0.2T |
| 12 | 1,1-Diphenyl-1-fluoro-2-aminopropane | 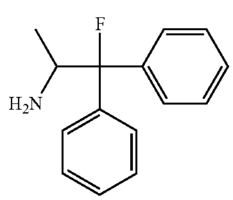 [SMILES: CC(N)C(F)(c1ccccc1)c1ccccc1] | 11.63 | 1.07 | 1.5 | 90H10I0.1TFA |

TABLE 8-continued

Examples of chromatic separations of racemic primary amine-containing compounds using a column bonded with a CSP including IP—CF6.

| | Compound name | Structure | $k_1$ | α | Rs | Mobile phase[a] |
|---|---|---|---|---|---|---|
| 13 | 1,2,2-Triphenylethylamine | 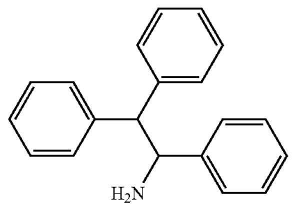 [SMILES: NC(c1ccccc1)C(c1ccccc1)c1ccccc1] | 0.65 | 1.22 | 2.2 | 75A25M0.3AA0.2T |
| 14 | N-p-Tosyl-1,2-diphenylethyl-enediamine | (1R,2R / 1S,2S) | 1.66 | 1.48 | 1.6 | 60H40E0.1TFA |
| 15 | α-Methylbenzylamine | 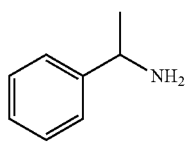 | 0.86 | 1.17 | 1.8 | 30A70M0.3AA02T |
| 16 | β-Methylphenethylamine | 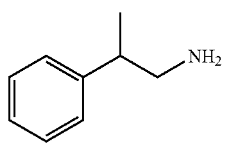 | 8.86 | 1.03 | 0.6 | 75A25M0.3AA0.2T |
| 17 | 2-Phenylglycinonitrile hydrochloride | 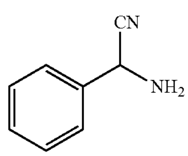 | 8.98 | 1.09 | 1.7 | 70H30E0.1TFA |
| 18 | 1,2-Diphenylethylamine | 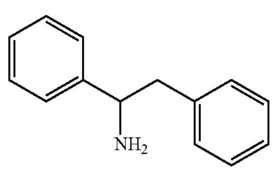 [SMILES: NC(Cc1ccccc1)c1ccccc1] | 2.20 | 1.19 | 2.0 | 60A40M0.3AA0.2T |
| 19 | 1,2-Diphenylethylenediamine | (1S,2S / 1R,2R) | 5.48 | 1.14 | 1.5 | 75A25M0.3AA0.2T0C[f] |
| 20 | Amphetamine sulfate salt | ·H₂SO₄ | 4.45 | 1.03 | 0.7 | 60A40M0.3AA0.2T |
| 21 | α-Methyl-4-nitrobenzylamine hydrochloride | ·HCl | 1.26 | 1.13 | 1.9 | 30A70M0.3AA0.2T |

TABLE 8-continued

Examples of chromatic separations of racemic primary amine-containing compounds using a column bonded with a CSP including IP—CF6.

| | Compound name | Structure | $k_1$ | α | Rs | Mobile phase[a] |
|---|---|---|---|---|---|---|
| 22 | 4-Fluoro-α-methylbenzyl-amine | 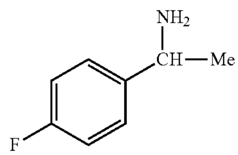 | 1.43 | 1.21 | 1.6 | 30A70M0.3AA0.2T0C. |
| 23 | 2,4-Dichloro-α-phenethyl-amine | 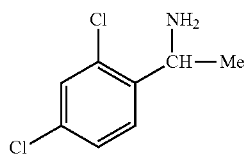 [SMILES: CC(N)c1ccc(Cl)cc1Cl] | 0.82 | 1.32 | 2.6 | 30A70M0.3AA0.2T |
| 24 | 1-(4-Methylphenyl)-ethylamine | 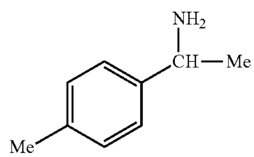 | 1.24 | 1.22 | 1.7 | 30A70M0.3AA0.2T0C. |
| 25 | 1-(1,1'-Biphenyl-4-yl)-ethylamine | 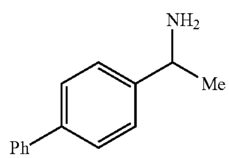 [SMILES: CC(N)c1ccc(-c2ccccc2)cc1] | 0.97 | 1.17 | 2.2 | 30A70M0.3AA0.2T |
| 26 | α-Ethylbenzylamine | 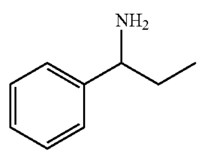 | 0.94 | 1.19 | 2.8 | 30A70M0.3AA0.2T |
| 27 | 4-Methoxy-α-methylbenzyl-amine | 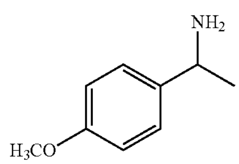 | 1.14 | 1.11 | 1.5 | 30A70M0.3AA0.3T |
| 28 | 1-(4-Chlorophenyl)ethyl-amine | 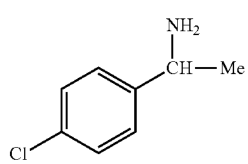 | 1.30 | 1.15 | 1.9 | 30A70M0.3AA0.4T |
| 29 | 1-(2-Methoxyphenyl)-ethanamine hydrochloride | 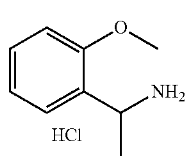 | 0.84 | 1.17 | 2.4 | 30A70M0.3AA0.5T |
| 30 | Amino(1,3-benzodioxol-5-yl)-acetonitrile | 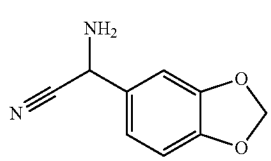 [SMILES: N#CC(N)c1ccc2c(c1)OCO2] | 2.79 | 1.09 | 1.0 | 60H40E0.1TFA |

TABLE 8-continued

Examples of chromatic separations of racemic primary amine-containing compounds using a column bonded with a CSP including IP—CF6.

| | Compound name | Structure | $k_1$ | α | Rs | Mobile phase[a] |
|---|---|---|---|---|---|---|
| 31 | 6-Methoxy-1,2,3,4-tetra-hydro-1-naphthalenylamine | 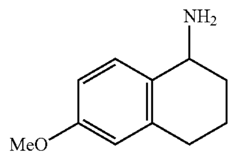 [SMILES: COc1ccc2c(c1)CCCC2N] | 0.97 | 1.18 | 2.4 | 30A70M0.3AA0.5T |
| 32 | 4-Chlorobenzhydrylamine hydrochloride | 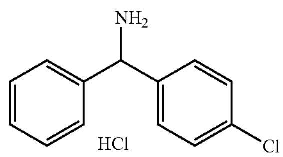 [SMILES: NC(c1ccccc1)c1ccc(Cl)cc1 ; Cl] | 2.29 | 1.35 | 1.5 | 60H40E0.1TFA |
| 33 | 1-Methyl-1-phenyl-propyl-amine | 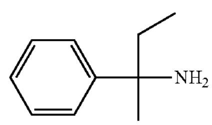 | 0.92 | 1.18 | 2.5 | 30A70M0.3AA0.5T |
| 34 | 2-Chloro-indan-1-ylamine hydrochloride[e] | 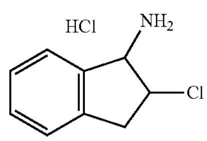 [SMILES: NC1c2ccccc2CC1Cl ; Cl] | 0.58 | 1.33 | 3.6 | 30A70M0.3AA0.5T |
| | | | 2.89 | 1.07 | 1.5 | 60A40M0.3AA0.5T |
| 35 | 4-Methyl-alpha-phenylphen-ethylamine | 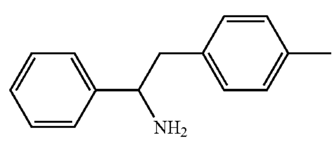 | 0.77 | 1.25 | 3.0 | 30A70M0.3AA0.5T |
| 36 | 4-(Amino-p-tolyl-methyl)-phenol | 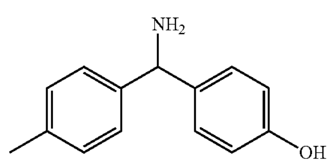 [SMILES: Cc1ccc(C(N)c2ccc(O)cc2)cc1] | 6.31 | 1.16 | 1.8 | 60H40E0.1TFA |
| 37 | DL-Homocysteine thiolactone hydrochloride | 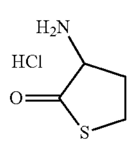 | 13.25 | 1.14 | 1.1 | 60H40E0.1TFA |
| 38 | Cyclohexylethylamine | 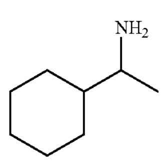 | 6.22 | 1.11 | 1.7 | 70A30M0.3AA0.2T[c] |
| 39 | endo-2-Amino norbornane hydrochloride | 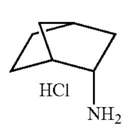 | 0.97 | 1.29 | 1.9 | 30A70M0.3AA0.2T[d] |
| 40 | exo-2-Amino norbornane | 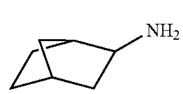 | 3.69 | 1.10 | 1.5 | 70A30M1.2AA0.8T[b] |

TABLE 8-continued

Examples of chromatic separations of racemic primary amine-containing compounds using a column bonded with a CSP including IP—CF6.

| | Compound name | Structure | $k_1$ | α | Rs | Mobile phase[a] |
|---|---|---|---|---|---|---|
| 41 | 3-Aminoquinuclidine dihydrochloride | 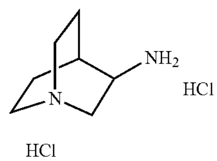 | 5.05 | 1.10 | 1.2 | 80A20M0.1TFA0.1T[c] |
| 42 | 2,2'-Diamino-1,1'-binaphthalene | 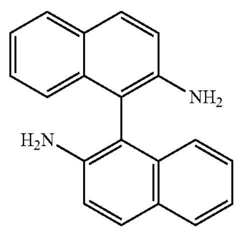 [SMILES: Nc1ccc2ccccc2c1-c1c(N)ccc2ccccc12] | 2.15 | 1.16 | 3.0 | 80H20E |
| 43 | Fipronil | 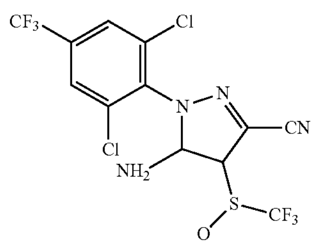 | 2.83 | 1.08 | 1.5 | 90H 10E0.1TFA |
| 44 | Aminoglutethimide | 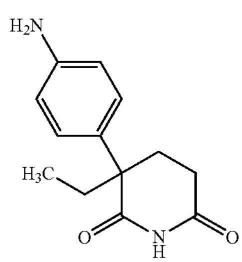 [SMILES: CCC1(c2ccc(N)cc2)CCC(=O)NC1=O] | 2.41 | 1.06 | 0.9 | 60H40E0.1TFA |

[a]Abbreviations:

A = acetonitrile;

M = methanol;

AA = acetic acid;

T = triethylamine;

H = heptane;

E = ethanol;

TFA = trifluoroacetic acid;

0C = the column temperature is set at 0° C.

[b]Detected with the refractive index detector; the column flow rate was 0.5 mL/min.

[c]Detected with the refractive index detector; the column flow rate was 1 mL/min.

[d]Detected with post-column fluorescence derivatization.

[e]This analyte consisted of two pairs of enantiomers.

[f]The flow rate was 0.5 mL/min.

TABLE 9

Examples of chromatic separations of racemic primary amine-containing compounds using a column bonded with a CSP including RN-CF6.

| | Compound name | Structure | $k_1$ | α | $R_S$ | Mobile phase[b] |
|---|---|---|---|---|---|---|
| 1 | 2-Amino-1,1-diphenyl-1-propanol[a] | 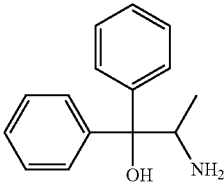 [SMILES: CC(N)C(O)(c1ccccc1)c1ccccc1] | 5.23 | 1.11 | 1.5 | 80H20E0.1TFA |
| 2 | 2-Amino-3-methyl-1,1-diphenyl-1-butanol[a] | 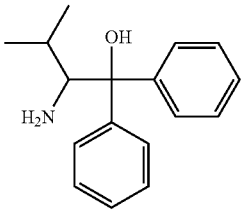 [SMILES: CC(C)C(N)C(O)(c1ccccc1)c1ccccc1] | 9.00 | 1.06 | 1.5 | 90H10E0.1TFA[c] |
| 3 | 2-Amino-1,1,3-triphenyl-1-propanol[a] | 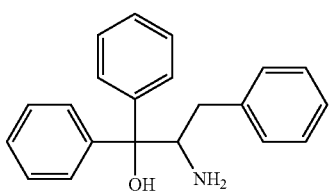 [SMILES: NC(Cc1ccccc1)C(O)(c1ccccc1)c1ccccc1] | 3.40 | 1.10 | 1.5 | 80H20E0.1TFA |
| 4 | DL-Tyrosine methyl ester hydrochloride | 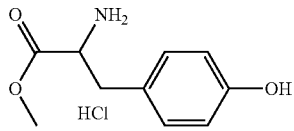 | 5.04 | 1.11 | 1.7 | 70H30E0.1TFA |
| 5 | 2-Phenylglycine methyl ester hydrochloride | 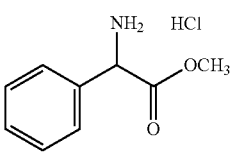 [SMILES: COC(=O)C(N)c1ccccc1 ; Cl] | 11.31 | 1.06 | 1.5 | 80H20E0.1TFA[c] |
| 6 | Tryptophan benzyl ester | 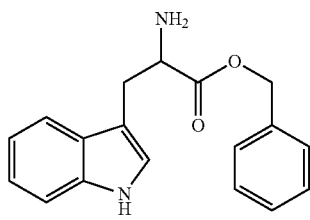 [SMILES: NC(Cc1c[nH]c2ccccc12)C(=O)OCc1ccccc1] | 11.30 | 1.07 | 1.8 | 80H20E0.1TFA[c] |
| 7 | Phenylalanine benzyl ester hydrochloride | 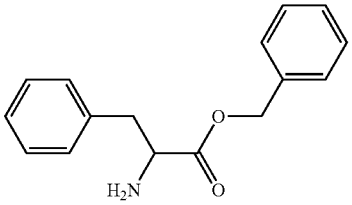 | 7.53 | 1.07 | 1.0 | 80H20E0.1TFA |
| 8 | Chlorophenylalanine ethyl ester hydrochloride[a] | 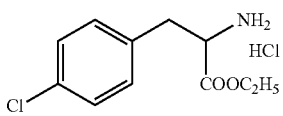 | 16.14 | 1.04 | 0.7 | 90H10E0.1TFA |

TABLE 9-continued

Examples of chromatic separations of racemic primary amine-containing compounds using a column bonded with a CSP including RN-CF6.

| | Compound name | Structure | $k_1$ | α | $R_S$ | Mobile phase[b] |
|---|---|---|---|---|---|---|
| 9 | DL-alanine-β-naphthylamide hydrochloride | 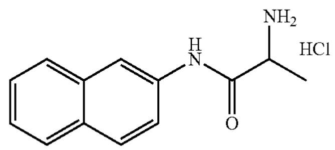 [SMILES: CC(N)C(=O)Nc1ccc2ccccc2c1 ; Cl] | 10.03 | 1.10 | 1.5 | 80H20E0.1TFA |
| 10 | 6-Methyl-DL-tryptophan | 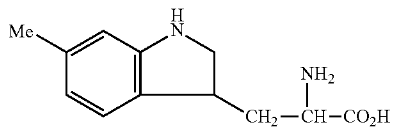 [SMILES: Cc1ccc2c(c1)NCC2CC(N)C(=O)O] | 13.96 | 1.16 | 1.6 | 80H20E0.1TFA |
| 11 | DL-Thyroxine | 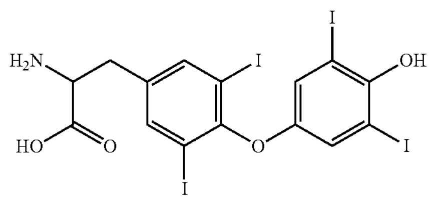 [SMILES: NC(Cc1cc(I)c(Oc2cc(I)c(O)c(I)c2)c(I)c1)C(=O)O] | 1.07 | 1.34 | 1.6 | 60H40E0.1TFA |
| 12 | 2-Aminomethyl-1,4-benzodioxane[a] | 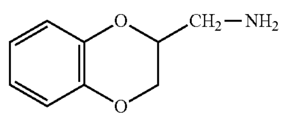 [SMILES: NCC1COc2ccccc2O1] | 5.28 | 1.05 | 0.7 | 60H40E0.1TFA |
| 13 | 1-Methyl-3-phenylpropyl-amine[a] | 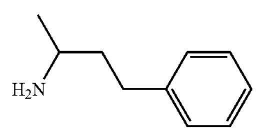 | 9.76 | 1.05 | 0.4 | 85H15E0.1TFA |

[a]Eantiomers of the analyte were not separated by the IP-CF6 CSP.
[b]Abbreviations: H = heptanes; E = ethanol; TFA = trifluoroacetic acid.
[c]The flow rate was 0.5 mL/min.

Desirable characteristics that can be exhibited by various but not necessarily all embodiments of the present invention can include, but are not limited to, the following: the provision of a wide array of derivatized cyclofructans, including polymeric cyclofructans; the provision of exceptional chiral selectors which can be "tuned" to separate enantiomers of different types of molecules as well as other chemical species which are not enantiomers; the provision of CSPs that effectively separate various chemical species in a variety of organic solvents, supercritical $CO_2$, and aqueous solvents; and the provision of analytical and preparative scale chromatographic methods for separating a variety of chemical species.

Various embodiments of the invention have been described in fulfillment of the various objectives of the invention. It should be recognized that these embodiments are merely illustrative of the principles of the present invention. Numerous modifications and adaptations thereof will be readily apparent to those of skill in the art without departing from the spirit and scope of the invention.

We claim:

1. A chiral stationary phase comprising:
   a solid support; and
   a derivatized cyclofructan residue of formula I:

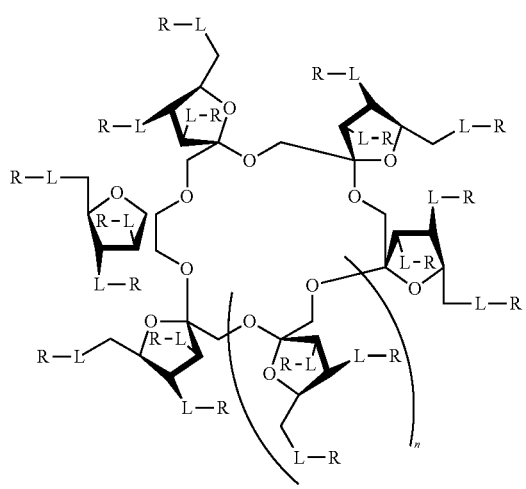

wherein:
n is 1-3;
each L is, independently,
    O—C(═O), or
    O—C(═O)—$NR^2$,
each R is, independently, H,
(C₁-C₂₀)alkyl optionally substituted with 1-3 R¹,
(C₃-C₂₀)cycloalkyl optionally substituted with 1-3 R¹,
(C₅-C₅₀)aryl optionally substituted with 1-3 R¹,
heteroaryl optionally substituted with 1-3 R¹,
(C₁-C₂₀)alkoxy(C₁-C₂₀)alkyl,
H₂C=CH— (when L is O—C(=O)),
H₂C=C(CH₃)— (when L is O—C(=O)),
alkylenyl-N=C=O;
arylenyl-N=C=O;
(C₅-C₅₀)aryl(C₁-C₂₀)alkyl optionally substituted with 1-3 R¹, or
saccharide residue lacking a hydroxyl group (when L is O), or
comprises a covalent bond to said solid support;
R¹ is, independently, (C₁-C₁₀)alkyl optionally substituted with 1-3 R⁶, halo, hydroxy, —NR³R⁴, —COOR², —COR², nitro, trihaloalkyl, or —Si(OR²)₃;
R² is, independently, H or (C₁-C₁₀)alkyl;
R³ is, independently, H or (C₁-C₁₀)alkyl;
R⁴ is, independently, H or (C₁-C₁₀)alkyl;
R⁵ is, independently, (C₁-C₂₀)alkyl optionally substituted with 1-3 R¹, (C₅-C₅₀)aryl optionally substituted with 1-3 R¹, or heteroaryl optionally substituted with 1-3R¹;
R⁶ is, independently, halo, hydroxy, —NR³R⁴, —COOR², —COR², nitro, trihaloalkyl, or —Si(OR²)₃;
wherein one to five R groups comprise covalent bonds to the solid support; and
wherein the average degree of derivatization ranges from about 2 to about 7.

2. A composition of claim 1,
wherein said solid support is a silica gel support.

3. A composition of claim 1,
wherein n is 1.

4. A composition of claim 1,
wherein n is 2.

5. A composition of claim 1,
wherein n is 3.

6. A composition of claim 1,
wherein at least one L is O—C(=O).

7. A composition of claim 1,
wherein at least one L is O—C(=O)—NR₂.

8. A composition of claim 1,
wherein each R is, independently, H, methyl, ethyl, n-propyl, isopropyl, n-butyl, t-butyl, cyclohexyl, phenyl, tolyl, trichlorophenyl, chlorophenyl, bromophenyl, iodophenyl, hydroxyethyl, hydroxypropyl, dichlorophenyl, benzyl, chlorotolyl, naphthylethyl, nitrophenyl, dinitrophenyl, trinitrophenyl, trifluoromethyl, dinitro, 3,5-dimethylphenyl, or adamantyl.

9. A composition of claim 1,
wherein each R is, independently, isopropyl, tert-butyl, xylyl, dichlorophenyl, naphthylethyl, or 3,5-dimethylphenyl.

10. A composition of claim 1,
wherein each R¹ is, independently, hydroxypropyl, hydroxyethyl, methyl, trichloromethyl, trifluoromethyl, chloro, bromo, or iodo.

11. A composition, comprising:
a solid support; and
at least one polymer, wherein said polymer comprises at least one residue of a derivatized cyclofructan of formula I:

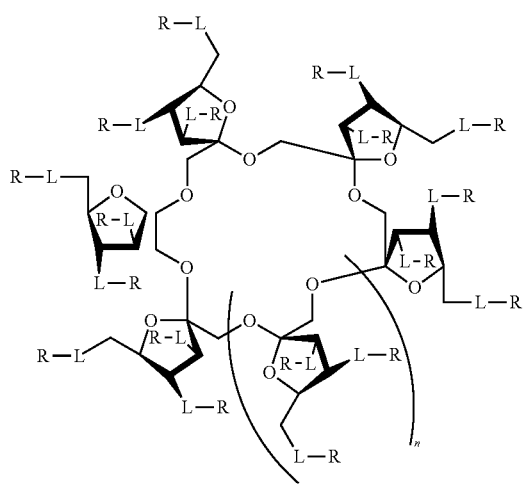

wherein:
each n is, independently, 1-3;
each L is, independently,
    O—C(=O), or
    O—C(=O)—NR²;
each R is, independently,
Y,
Z,
H,
(C₁-C₂₀)alkyl optionally substituted with 1-3 R¹,
(C₃-C₂₀)cycloalkyl optionally substituted with 1-3 R¹,
(C₅-C₅₀)aryl optionally substituted with 1-3 R¹,
heteroaryl optionally substituted with 1-3 R¹,
(C₁-C₂₀)alkoxy(C₁-C₂₀)alkyl,
H₂C=CH— (when L is O—C(=O)),
H₂C=C(CH₃)— (when L is O—C(=O)),
alkylenyl-N=C=O;
arylenyl-N=C=O;
(C₅-C₅₀)aryl(C₁-C₂₀)alkyl optionally substituted with 1-3 R¹, or
saccharide residue lacking a hydroxyl group (when L is O),
R¹ is, independently, (C₁-C₁₀)alkyl optionally substituted with 1-3 R⁶, halo, hydroxy, —NR³R⁴, —COOR², —COR², nitro, trihaloalkyl, or —Si(OR²)₃;
R² is, independently, H or (C₁-C₁₀)alkyl;
R³ is, independently, H or (C₁-C₁₀)alkyl;
R⁴ is, independently, H or (C₁-C₁₀)alkyl;
R⁵ is, independently, (C₁-C₂₀)alkyl optionally substituted with 1-3 R¹, (C₅-C₅₀)aryl optionally substituted with 1-3 R¹, or heteroaryl optionally substituted with 1-3 R¹;
R⁶ is, independently, halo, hydroxy, —NR³R⁴, —COOR², —COR², nitro, trihaloalkyl, or —Si(OR²)₃; and
Y comprises a covalent bond to a different monomer residue; and
Z comprises a covalent bond to said solid support; and
wherein zero to five R groups comprise covalent bonds to the solid support; and
wherein the average degree of derivatization ranges from about 2 to about 7.

12. A composition of claim 11,
wherein said polymer forms a coating on said solid support.

13. A composition of claim 11,
wherein said polymer is covalently bonded to said solid support.

14. A composition of claim 11,
wherein said residue of a derivatized cyclofructan of formula I forms a pendant group on said polymer.

15. A composition of claim 11,
wherein said residue of a derivatized cyclofructan of formula I forms a portion of the backbone of said polymer.

16. A chiral stationary phase, comprising:
a solid support; and
a derivatized cyclofructan residue of formula I:

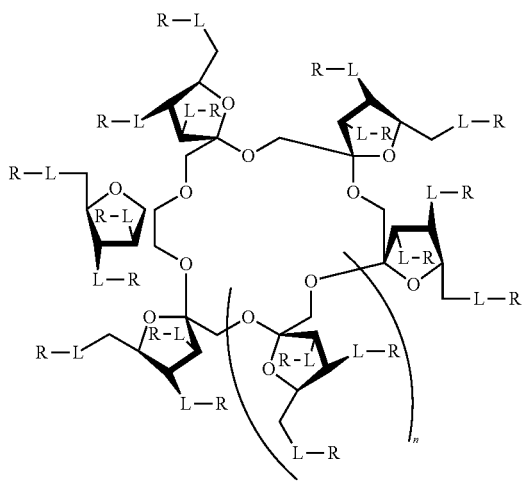

wherein:

n is 1-3;

each L is, independently,

O—C(=O) or O—C(=O)—NR$^2$;

each R is, independently, isopropyl, 3,5-dimethylphenyl, R-naphthylethyl carbamate, dichlorophenyl, cyclopentyl, cyclohexyl, and methylchlorophenyl;

wherein one to five R groups comprise covalent bonds to the solid support; and wherein the average degree of derivatization ranges from about 2 to 24.

17. A chiral stationary phase of claim 16,
wherein said solid support is a silica gel support.

18. A composition of claim 16,
wherein at least one L is O—C(=O).

19. A composition of claim 16,
wherein at least one L is O—C(=O)—NR$^2$.

* * * * *